United States Patent
Miyazawa et al.

[11] Patent Number: 6,143,198
[45] Date of Patent: *Nov. 7, 2000

[54] LIQUID CRYSTALLINE COMPOUNDS HAVING EXO-METHYLENE SITE AND LIQUID CRYSTAL COMPOSITIONS COMPRISING THE SAME

[75] Inventors: Kazutoshi Miyazawa; Shuichi Matsui; Yasuko Sekiguchi; Etsuo Nakagawa, all of Chiba, Japan

[73] Assignee: Chisso Corporation, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/952,681

[22] PCT Filed: May 24, 1996

[86] PCT No.: PCT/JP96/01397

§ 371 Date: Nov. 25, 1997

§ 102(e) Date: Nov. 25, 1997

[87] PCT Pub. No.: WO96/37451

PCT Pub. Date: Nov. 28, 1996

[30] Foreign Application Priority Data

May 25, 1995 [JP] Japan ................................. 7-150890

[51] Int. Cl.[7] .......................... C09K 19/34; C09K 19/32; C09K 19/30; C09K 19/12
[52] U.S. Cl. ................ 252/299.61; 252/299.62; 252/299.63; 252/299.66; 252/299.67; 544/298; 546/339; 549/369; 570/12; 570/144; 568/626
[58] Field of Search ......... 252/299.61, 299.62, 252/299.63; 544/298; 568/626; 546/339; 549/369; 570/128, 144

[56] References Cited

U.S. PATENT DOCUMENTS

| | | | |
|---|---|---|---|
| 4,629,581 | 12/1986 | Petrzilka et al. | 252/299.63 |
| 4,801,734 | 1/1989 | Kock et al. | 560/73 |
| 5,164,111 | 11/1992 | Dorsch et al. | 252/299.01 |
| 5,458,805 | 10/1995 | Wachtler et al. | 252/299.61 |
| 5,518,652 | 5/1996 | Parri et al. | 252/299.01 |
| 5,609,791 | 3/1997 | Fujita et al. | 252/299.63 |
| 5,653,911 | 8/1997 | Kondo et al. | 252/299.01 |
| 5,662,828 | 9/1997 | Tsubata et al. | 252/299.61 |
| 5,709,911 | 1/1998 | Onishi et al. | 428/1 |

FOREIGN PATENT DOCUMENTS

| | | |
|---|---|---|
| 0 168 683 A3 | 1/1986 | European Pat. Off. |
| 0 563 982 A3 | 10/1993 | European Pat. Off. |
| 0 647 696 A1 | 4/1995 | European Pat. Off. |
| 4025550 A1 | 2/1991 | Germany. |

OTHER PUBLICATIONS

Schadt et al., "Polar Alkenyls: Physical Properties and Correlations with Molecular Structure of New Nematic Liquid Crystals", Mol. Cryst. Liq. Cryst., 1985, vol. 122, pp. 241–260.

*Primary Examiner*—C. H. Kelly
*Attorney, Agent, or Firm*—Wenderoth, Lind & Ponack, L.L.P.

[57] ABSTRACT

A liquid crystalline compound represented by the general formula (1)

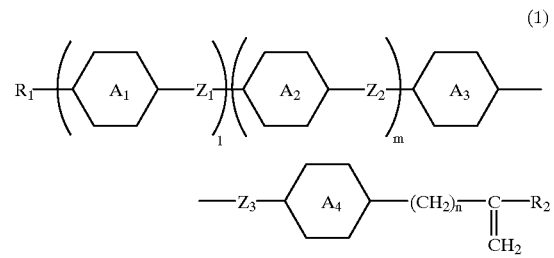

wherein $R_1$ represents an alkyl or alkoxy group having 1 to 10 carbon atoms, a cyano group, a halogen atom, or an alkyl or alkoxy halide group having 1 to 4 carbon atoms; $R_2$ represents an alkyl group having 1 to 10 carbon atoms; rings $A_1$, $A_2$, $A_3$, and $A_4$ each independently represent a 1,4-phenylene or 1,4-cyclohexylene group; $Z_1$, $Z_2$, and $Z_3$ each independently represent a covalint bond, —$CH_2CH_2$—, —CH=CH—, —C≡C— or —COO—; 1 and m are 0 pr 1; and n is 0 to 10.

17 Claims, No Drawings

LIQUID CRYSTALLINE COMPOUNDS HAVING EXO-METHYLENE SITE AND LIQUID CRYSTAL COMPOSITIONS COMPRISING THE SAME

This application is a 371 of International Application No. PCT/JP96/01397 filed May 24, 1996.

TECHNICAL FIELD

The present invention relates to novel liquid crystalline compounds, which can develop various properties suitable for use as electro-optical display materials, and liquid crystal compositions, having various favorable properties, using the novel liquid crystalline compounds.

BACKGROUND ART

Liquid crystal display devices are used in watches and clocks, electric calculators, various types of measuring equipment, panels for automobiles, word processors, electronic message pads, printers, computers, televisions, etc. The liquid crystal displays take advantage of optical anisotropy and anisotropy of dielectric constant which liquid crystalline compounds possess. Known display systems for this purpose include twisted nematic (TN), super-twisted nematic (STN), dynamic scattering (DS), guest-host (G-H), DAP, ferroelectric liquid crystal (FLC) display systems. Drive systems, for these display systems, known in the art include static drive, time-sharing drive, active-matrix drive, and double-channel drive systems.

Various properties are required of the liquid crystal materials depending upon display systems and drive systems. However, 1) a wide temperature range of liquid crystal phase and 2) low viscosity are important properties required in common to all the systems. Properties necessary for meeting the requirement 1) include a high upper limit temperature of the nematic phase and a melting point low enough to prevent phase separation such as crystallization in a low temperature region.

The properties of liquid crystalline compounds used in these various liquid crystal display devices vary depending upon applications of the liquid crystal display devices. However, good stability against external environment factors, such as moisture, air, heat, and light, are required of the all the liquid crystalline compounds used for these purposes. Further, these liquid crystalline compounds are required to exhibit a liquid crystal phase in an as wide as possible temperature range around room temperature.

A liquid crystal composition for use in liquid crystal display devices comprises several to twenty-odd liquid crystalline compounds in order to develop optimal properties required of individual display devices. For this purpose, good compatibility with other liquid crystalline compounds, particularly good compatibility with other liquid crystalline compounds at a low temperature due to an ever-increasing demand for use of the display device under various environments, is required of the liquid crystalline compounds.

Liquid crystal compositions for use in the STN drive system are required to have steep threshold properties from the viewpoint of realizing a high image quality. The steepness is a function of the elastic constant ratio K33/K11, and it is known that the steepness of the threshold properties increases with increasing the elastic constant ratio of liquid crystalline compounds used in the liquid crystal composition (F. Leenhouts et al., Proceedings of the Japan Display, 388 (1986)).

The following compounds having an alkenyl site are known to have a large elastic constant ratio K33/K11: the following compounds (a) described in M. Schadt et al., Mol. Cryst. Liq. Cryst., 122 (1985) and Japanese Patent Laid-Open No. 83136/1986:

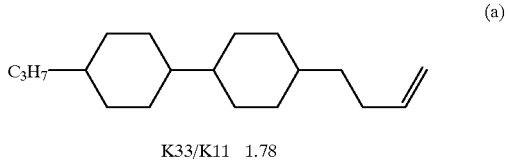

(a)

K33/K11 1.78 and the following compounds (b), containing a fluorine atoms, described in Japanese Patent Application No. 92740/1994:

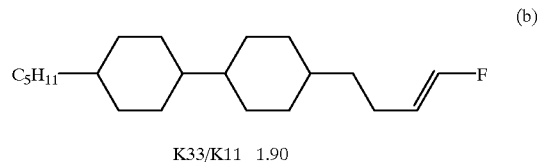

(b)

K33/K11 1.90

When the above alkenyl compounds were mixed in an amount of 15% by weight with a liquid crystal composition comprising
  24% of 4-(4-propylcyclohexyl)benzonitrile,
  36% of 4-(4-pentylcyclohexyl)benzonitrile,
  25% of 4-(4-heptylcyclohexyl)benzonitrile, and
  15% of 4-(4-pentylphenyl)benzonitrile,
and properties were measured, it was found that all the above compounds had a relatively large elastic constant ratio K33/K11 and all the liquid crystal compositions using these compounds had favorable steepness. The upper limit of the elastic constant ratio K33/K11 of a liquid crystalline compound having an alkenyl site on its side chain is that noted above. However, an ever-increasing demand for an improvement in display ability of liquid crystal display devices has led to a demand for compounds having more steep threshold properties. In other words, liquid crystalline compounds having a larger elastic constant ratio K33/K11 have been desired in the art. That is, the provision of a novel skeleton other than alkenyl compounds has been desired in the art.

Compounds (c) having a 1,3-butadienyl group, represented by the following structural formula, described in Japanese Patent Laid-Open No. 286873/1993 are also known to have a high elastic constant ratio K33/K11:

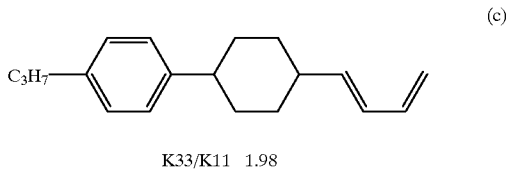

(c)

K33/K11 1.98

These compounds, however, do not have a satisfactorily high elastic constant ratio K33/K11 and, since the 1,3-butadienyl group has a conjugated diene site, chemically very unstable, making it impossible to use them in liquid crystal compositions for practical purpose.

That is, the development of liquid crystalline compounds, for STN, possessing a very large elastic constant ratio K33/K11, high chemical stability, and good compatibility with other liquid crystalline compounds has been desired in the art.

Liquid crystal compositions designed for active-matrix liquid crystal displays with an integrated non-linear element incorporated thereinto for switching individual pixels, particularly, for TFT, should have large positive anisotropy of dielectric constant and, in addition, very high specific resistance (high voltage retention), good UV stability, and high compatibility with other liquid crystalline compounds at a low temperature.

The active-matrix liquid crystal displays are suitable particularly for displays for televisions, advanced information displays for computers, and advanced information displays in automobiles and airplanes. However, when liquid crystalline compounds or liquid crystalline compositions not having very high specific resistance (high voltage retention) or good UV stability are used, the contrast decreases with a lowering in electrical resistance in the liquid crystal panel, posing a problem of "afterimage quenching."

High electrical resistance of the liquid crystal composition is a very important factor which determines the service life, particularly in the case of low-voltage drive. For this reason, very high specific resistance (high voltage retention) and good UV stability are very important properties required of liquid crystalline compounds used.

Further, in order to enable use of the liquid crystal composition in a wide temperature range, the liquid crystal composition should have a nematic phase particularly at a low temperature. Therefore, liquid crystal compositions free from the precipitation of a crystal or the development of a smectic phase and having a minimized temperature dependence of viscosity at a low temperature have been desired in the art. For this, that the liquid crystalline compound used has high compatibility with other liquid crystalline compounds at a low temperature is very important.

However, no conventional liquid crystalline compounds, for TFT, which have a combination of large positive anisotropy of dielectric constant, very high specific resistance (high voltage retention), good UV stability, high compatibility with other liquid crystalline compounds at a low temperature, are known in the art.

An object of the present invention is to provide a novel liquid crystalline compound having a large elastic constant ratio, excellent compatibility with other liquid crystalline compound(s) particularly at a low temperature, and chemical stability, or a liquid crystalline compound having a combination of a large positive anisotropy of dielectric constant, a very high specific resistance (a high voltage retention), good UV stability, and high compatibility with other liquid crystalline compound(s) at a low temperature, and a liquid crystal composition comprising the same.

DISCLOSURE OF INVENTION

The present inventors have extensive and intensive studies with a view to solving the above problems and, as a result, have found compounds having a novel structure and possessing better properties than the conventional liquid crystalline compounds.

Specifically, the present inventors have found compounds, with an exo-methylene site on their side chain, possessing better properties than the conventional liquid crystalline compounds, which has led to the completion of the present invention.

Thus, the first invention relates to a liquid crystalline compound represented by the general formula (1):

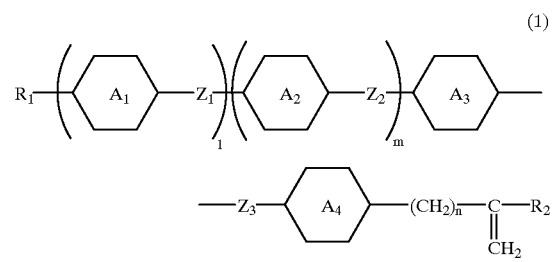

wherein $R_1$ represents an alkyl or alkoxy group having 1 to 10 carbon atoms, a cyano group, a halogen atom, or an alkyl or alkoxy halide group having 1 to 4 carbon atoms;

$R_2$ represents an alkyl group having 1 to 10 carbon atoms;

rings $A_1$, $A_2$, $A_3$, and $A_4$ each independently represent a 1,4-phenylene, 1,4-cyclohexylene, 1,4-cyclohexenylene, 1,3-dioxane-2,5-diyl, pyrimidine-2,5-diyl, pyridine-2,5-diyl, or bicyclo[1,1,1]pentanediyl group, provided that the rings may be substituted with one or more halogen atoms;

$Z_1$, $Z_2$, and $Z_3$ each independently represent a covalent bond, —$CH_2CH_2$—, —CH=CH—, —C≡C—, —COO—, —OCO—, —$CH_2O$—, —$OCH_2$— or —$(CH_2)_4$—;

1 and m are 0 or 1; and n is 0 to 10.

The second invention relates to a liquid crystalline compound represented by the general formula (1—1):

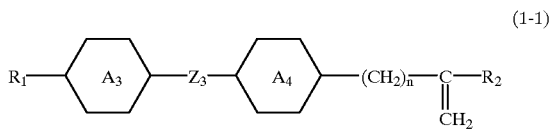

wherein $R_1$ represents an alkyl or alkoxy group having 1 to 10 carbon atoms, a cyano group, a halogen atom, or an alkyl or alkoxy halide group having 1 to 4 carbon atoms;

$R_2$ represents an alkyl group having 1 to 10 carbon atoms;

rings $A_3$ and $A_4$ each independently represent a 1,4-phenylene or 1,4-cyclohexylene, provided that the rings may be substituted with one or more halogen atoms;

$Z_3$ represents a covalent bond, —$CH_2CH_2$—, —CH=CH—, —C≡C—, —COO—, —OCO—, —$CH_2O$—, —$OCH_2$—, or —$(CH_2)_4$—; and n is 0 to 10.

The third invention relates to a liquid crystalline compound according to the second invention, wherein $Z_3$ represents a covalent bond, —$CH_2CH_2$—, —CH=CH— or —C≡C—.

The fourth invention relates to a liquid crystalline compound according to the second invention, wherein $R_1$ represents an alkyl group having 1 to 10 carbon atoms, rings $A_3$ and $A_4$ represent a 1,4-cyclohexylene group, $Z_3$ represents a covalent bond, —$CH_2CH_2$— or —CH=CH—and n is 0 to 10.

The fifth invention relates to a liquid crystalline compound represented by the general formula (1-2):

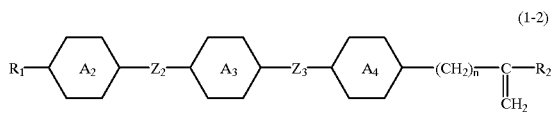

(1-2)

wherein $R_1$ represents an alkyl or alkoxy group having 1 to 10 carbon atoms, a cyano group, a halogen atom, or an alkyl or alkoxy halide group having 1 to 4 carbon atoms;

$R_2$ represents an alkyl group having 1 to 10 carbon atoms;

rings $A_2$, $A_3$ and $A_4$ each independently represent a 1,4-phenylene or 1,4-cyclohexylene group, provided that the rings may be substituted with one or more halogen atoms;

$Z_2$ and $Z_3$ each independently represent a covalent bond, $-CH_2CH_2-$, $-CH=CH-$, $-C\equiv C-$, $-COO-$, $-OCO-$, $-CH_2O-$, $-OCH_2-$ or $-(CH_2)_4-$; and n is 0 to 10.

The sixth invention relates to a liquid crystalline compound according to the fifth invention, wherein $Z_2$ and $Z_3$ each independently represent a covalent bond, $-CH_2CH_2-$, $-CH=CH-$, $-C\equiv C-$ or $-(CH_2)_4-$.

The seventh invention relates to a liquid crystalline compound according to the sixth invention, wherein $R_1$ represents a cyano group, a halogen atom, or an alkyl halide or alkoxy halide group having 1 to 4 carbon atoms and-ring $A_2$ represents a 1,4-phenylene group, provided that the ring may be substituted with one or more halogen atoms.

The eighth invention relates to a liquid crystalline compound according to the sixth invention, wherein $R_1$ represents an alkyl group having 1 to 10 carbon atoms, ring $A_2$ represents a 1,4-cyclohexylene group, provided that the ring may be substituted with one or more halogen atoms.

The ninth invention relates to a liquid crystalline compound according to the fifth invention, which is represented by the general formula (1-3):

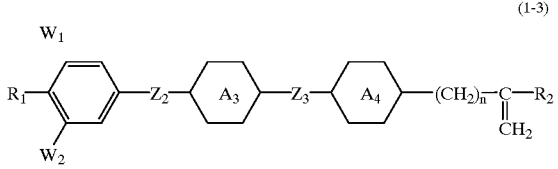

(1-3)

wherein $R_1$ represents a cyano group, a halogen atom, or an alkyl or alkoxy group having 1 to 4 carbon atoms;

$W_1$ and $W_2$ represent a fluorine or chlorine atom;

$Z_2$ and $Z_3$ each independently represent a covalent bond, $-CH_2CH_2-$ or $-(CH_2)_4-$; and n is 0 to 10.

The tenth invention relates to a liquid crystalline compound according to the ninth invention, wherein $R_1$ represents a cyano group, a fluorine or chlorine atom, a trifluoromethyl, trifluoromethoxy, difluoromethoxy, 1,1,2,2-tetrafluoroethoxy, 1,1,2,3,3,3-hexafluoropropoxy, 2,2-difluoroethoxy, or 2,2,2-trifluoroethoxy group and $Z_2$ and $Z_3$ each independently represent a covalent bond, $-CH_2CH_2-$ or $-(CH_2)_4-$.

The eleventh invention relates to a liquid crystal composition comprising at least one of which is a liquid crystalline compound represented by the general formula (1).

The twelfth invention relates to a liquid crystal composition comprising: a first component of at least one compound according to any one of the first to tenth inventions; and a second component of at least one member selected from the group consisting of compounds represented by the general formulae (2), (3), and (4):

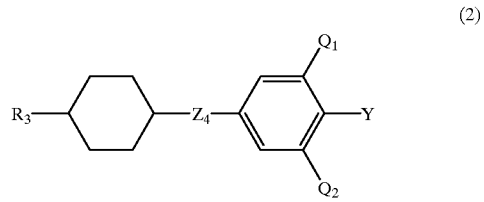

(2)

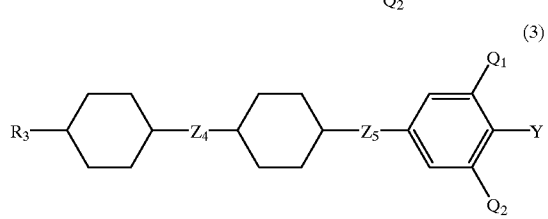

(3)

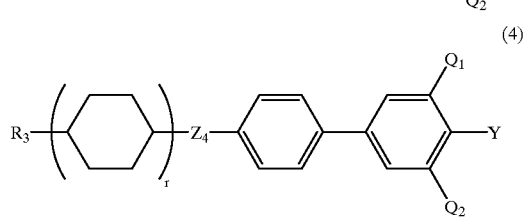

(4)

wherein $R_3$ represents an alkyl group having 1 to 10 carbon atoms, Y represents a fluorine or chlorine atom, $Q_1$ and $Q_2$ each independently represent a hydrogen or fluorine atom, r is 1 or 2, $Z_4$ and $Z_5$ each independently represent $-CH_2CH_2-$ or a covalent bond.

The thirteenth invention relates to a liquid crystal composition comprising: a first component of at least one compound according to any one of the first to tenth inventions; and a second component of at least one member selected from the group consisting of compounds represented by the general formulae (5), (6), (7), (8), and (9):

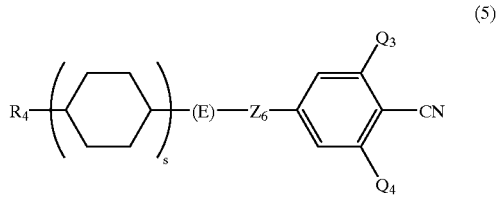

(5)

wherein $R_4$ represents an alkyl group having 1 to 10 carbon atoms or an alkenyl group having 2 to 10 carbon atoms, provided that although any methylene group ($-CH_2-$) may be replaced by an oxygen atom ($-O-$), two or more consecutive methylene groups are not simultaneously replaced by an oxygen atom, $Z_6$ represents $-CH_2CH_2-$, $-COO-$ or a covalent bond, $Q_3$ and $Q_4$ represent a hydrogen or fluorine atom H or F, E represents a cyclohexane, benzene, or 1,3-dioxane ring, and s is 0 or 1;

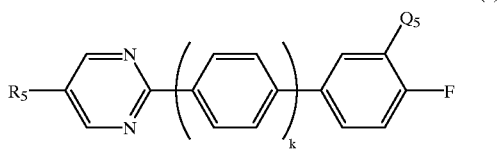

(6)

wherein $R_5$ represents an alkyl group having 1 to 10 carbon atoms, $Q_5$ represents a hydrogen or fluorine atom, and k is 0 or 1;

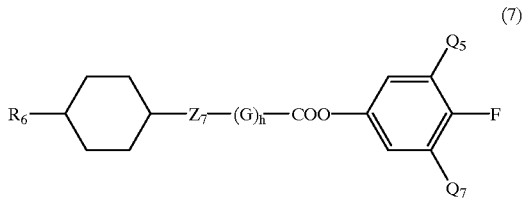

(7)

wherein $R_6$ represents an alkyl group having 1 to 10 carbon atoms, G represents a cyclohexane or benzene ring, $Q_6$ and $Q_7$ each independently represent a hydrogen or fluorine atom, $Z_7$ represents —COO— or a covalent bond, and h is 0 or 1;

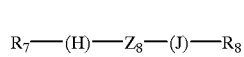

(8)

wherein $R_7$ and $R_8$ each independently represent an alkyl, alkyloxy, or alkyloxymethyl group having 1 to 10 carbon atoms, H represents a cyclohexane, pyrimidine or benzene ring, J represents a cyclohexane or benzene ring, and $Z_8$ represents —C≡C—, —COO—, —CH$_2$CH$_2$— or a covalent bond; and

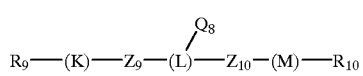

(9)

wherein $R_9$ represents an alkyl or alkoxyl group having 1 to 10 carbon atoms, $R_{10}$ represents an alkyl, alkyloxy, or alkoxymethyl group having 1 to 10 carbon atoms, K represents a cyclohexane or pyrimidine ring, L and M each independently represent a cyclohexane or benzene ring, $Z_9$ represents —COO—, —CH$_2$CH$_2$— or a covalent bond, $Z_{10}$ represents —C≡C—, —COO— or a covalent bond, and $Q_8$ represents a hydrogen or fluorine atom.

The fourteenth invention relates to a liquid crystal display device comprising a liquid crystal composition, the liquid crystal composition comprising at least one of which is a liquid crystalline compound represented by the general formula (1).

The fifteenth invention relates to a liquid crystal display device comprising a liquid crystal composition according to any one of the eleventh to fourteenth inventions.

The compounds, of the present invention, represented by the formula (1) features a large elastic constant ratio K33/K11, high specific resistance, high voltage retention, chemical stability, good UV stability, low viscosity, and good compatibility with other liquid crystalline compounds at a low temperature. Further, liquid crystal compositions using the compounds represented by the formula (1) have good steepness of threshold voltage and, hence, can be used to realize display devices which have high definition display quality and long service life and can be driven at a low temperature.

The compounds of the formula (1) according to the present invention have a particularly large elastic constant ratio K33/K11. In the prior art, compounds having a large elastic constant ratio have been limited to compounds having an alkenyl site on their side chain. No compounds having a skeleton other than that of the conventional compounds and, at the same time, possessing the above properties are utterly known in the art. Like the compounds of the formula (1) according to the present invention, compounds with an exo-methylene site incorporated on their side chain can develop a much larger elastic constant ratio than the conventional alkenyl derivatives.

Best Mode for Carrying Out the Invention

All the compounds of the present invention have favorable properties. The use of compounds represented by the formula (1) wherein $R_1$, $R_2$, rings $A_1$, $A_2$, $A_3$, $A_4$, $Z_1$, $Z_2$, and $Z_3$, l, m, and n have been properly selected enables the preparation of liquid crystal compositions having properties suitable for respective applications.

Specifically, in particular, a compound of three-ring system or a four-ring system may be used for the preparation of a composition which should have a liquid crystal temperature range on a high temperature side, while a compound of two-ring system or a three-ring system may be used for the preparation of a composition which is not required to have such a property.

When particularly large anisotropy of dielectric constant is necessary, a compound having positive anisotropy of dielectric constant (P type compound) is used as in the case of a conventional composition. In this case, a P type compound can be provided by selecting a halogen atom, a cyano group, or an alkyl halide group as $R_1$ in the formula (1). When larger anisotropy of dielectric constant is necessary, this can be achieved by introducing a halogen atom on a ring so as for dipoles to orient toward an identical direction.

When a compound having negative anisotropy of dielectric constant (N type compound) is desired, a group, of which the dipole moment is not large, for example, an alkyl or alkoxy group, may be introduced into $R_1$.

The anisotropy of refractive index also can be regulated, as desired, by selecting $R_1$, $R_2$, rings $A_1$, $A_2$, $A_3$, $A_4$, $Z_1$, $Z_2$, and $Z_3$, l, m, and n in the formula (1). Specifically, when large anisotropy of refractive index is necessary, a compound having a high 1,4-phenylene ring content may be used, while when small anisotropy of refractive index is necessary, a compound having a high trans-1,4-cyclohexylene content may be used.

The term "alkyl group" used includes straight-chain or branched alkyl groups having 1 to 10 carbon atoms. Among them, an alkyl group having 3 to 5 carbon atoms is particularly preferred from the viewpoint of low viscosity. Examples of preferred alkyl groups include methyl, ethyl, propyl, butyl, pentyl, hexyl, heptyl, octyl, isopropyl, isobutyl, isoamyl, isohexyl, 2-methylbutyl, 2-methylpentyl, and 3-methylpentyl groups, and the term "alkyl group" embraces racemic, S, and R forms.

The term "alkoxy group" used herein include straight-chain or branched alkoxy groups having 1 to 10 carbon atoms. Among them, an alkoxy group having 3 to 5 carbon atoms is preferred. Examples of preferred alkyl groups include methoxy, ethoxy, propoxy, butoxy, pentoxy, hexyloxy, heptyloxy, octyloxy, isopropoxy, isobutoxy, isoamyloxy, isohexyloxy, 2-methylbutoxy, 2-methylpentoxy, and 3-methylpentoxy groups, and the term "alkoxy group" embraces racemic, S, and R forms.

The term "alkyl halide group" used herein refers to an alkyl group, having 1 to 4 carbon atoms, with at least one fluorine atom and/or at least one chlorine atom bonded to a carbon atom(s). Among them, an alkyl groups subsitituted with fluorine atom(5) is preferred. Examples of preferred alkyl fluolide groups include monofluoromethyl, difluoromethyl, trifluoromethyl, 2-fluoroethyl, 2,2-difluoroethyl, 2,2,2-trifluoroethyl, 1,1,2,2-tetrafluoroethyl, perfluoroethyl, 3-fluoropropyl, 3,3-difluoropropyl, 3,3,3-trifluoropropyl, 2,2,3,3,3-pentafluoropropyl, 1,1,2,3,3,3-hexafluoropropyl, perfluoropropyl, 4-fluorobutyl, perfluorobutyl, and 5-fluoropentyl groups.

The term "alkoxy halide group" used herein refers to an alkoxy group, having 1 to 4 carbon atoms, with at least one fluorine atom and/or at least one chlorine atom bonded to a carbon atom(s). Examples of preferred alkoxy halide groups include monofluoromethoxy, difluoromethoxy, trifluoromethoxy, 2,2-difluoroethoxy, 2,2,2-trifluoroethoxy, 1,1,2,2-tetrafluoroethoxy, perfluoroethoxy, 3,3-difluoropropoxy, 3,3,3-trifluoropropoxy, 2,2,3,3,3-pentafluoropropoxy, 1,1,2,3,3,3-hexafluoropropoxy, perfluoropropoxy, and perfluorobutoxy groups.

Among the compounds of the formula (1) according to the present invention, a group of compounds represented by a group of general formulae (1-4) to (1-40) are preferred. $R_1$, $R_2$, rings $A_1$, $A_2$, $A_3$, and $A_4$, and n are as defined above.

(1-4)

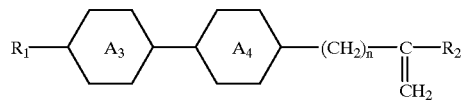

(1-5)

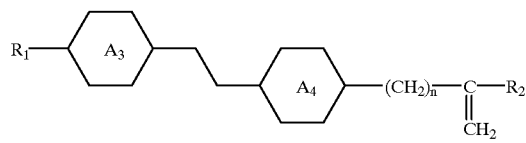

(1-6)

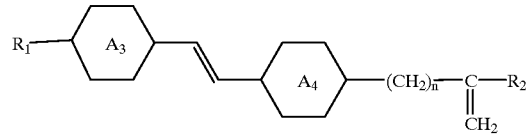

(1-7)

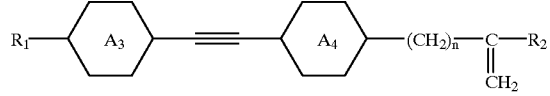

(1-8)

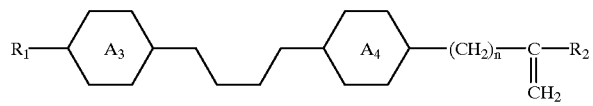

(1-9)

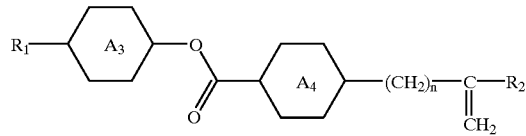

(1-10)

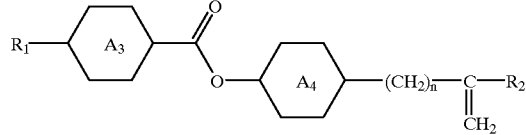

(1-11)

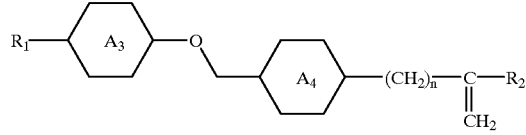

(1-12)
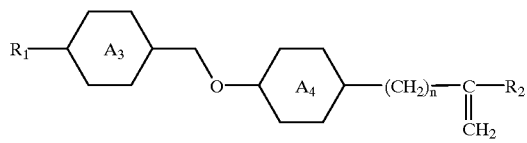
(1-13)
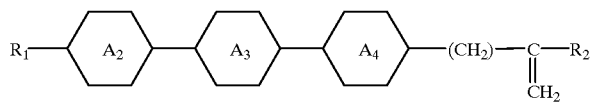
(1-14)
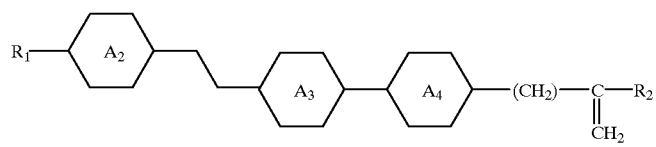
(1-15)
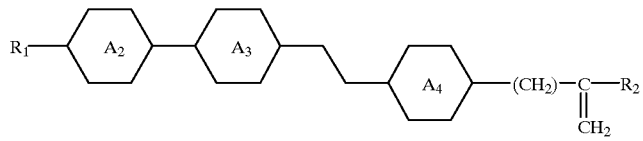
(1-16)
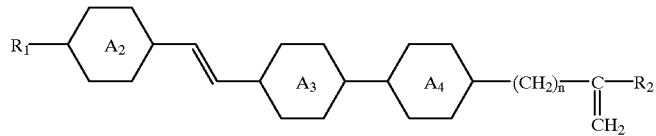
(1-17)
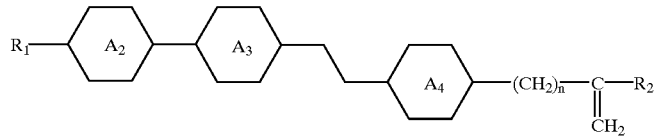
(1-18)
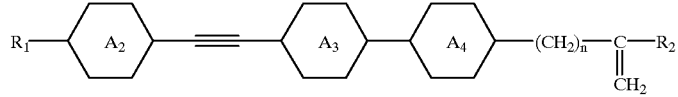
(1-19)
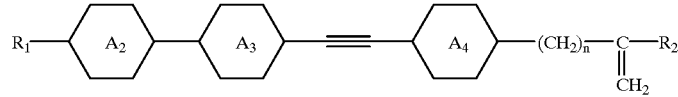
(1-20)
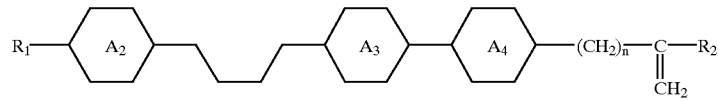
(1-21)
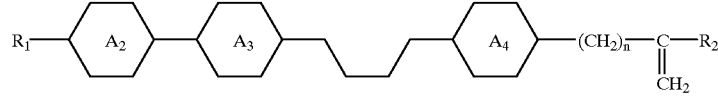

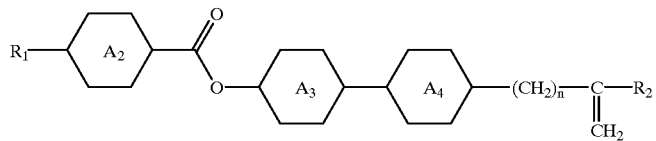
(1-22)
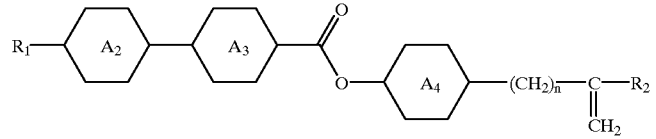
(1-23)
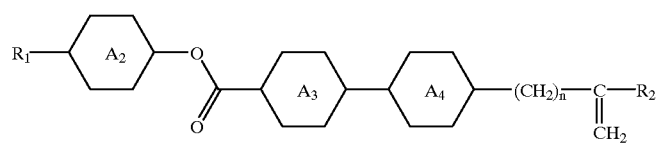
(1-24)
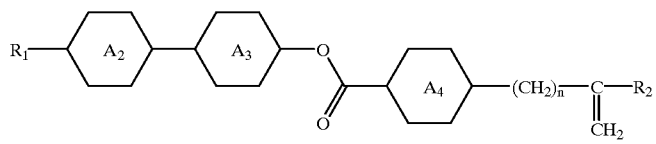
(1-25)
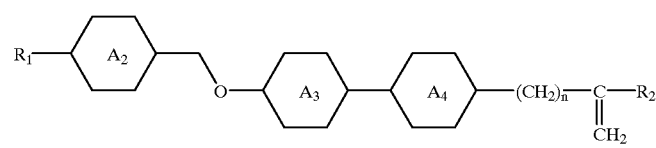
(1-26)
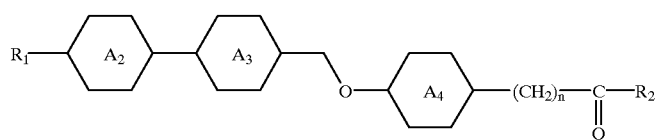
(1-27)
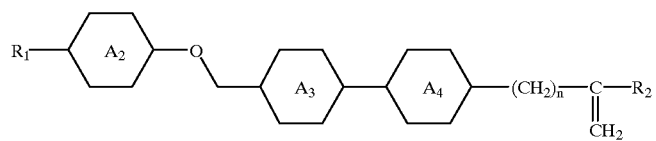
(1-28)
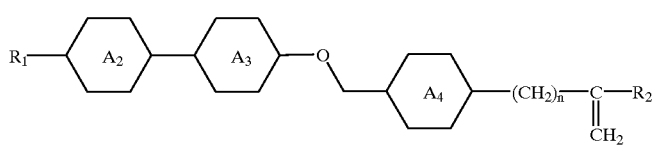
(1-29)
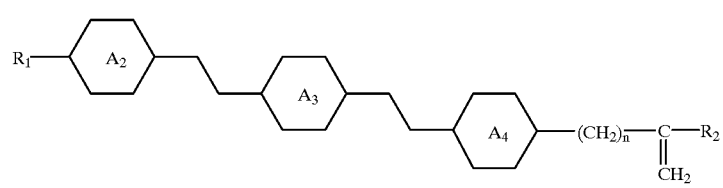
(1-30)

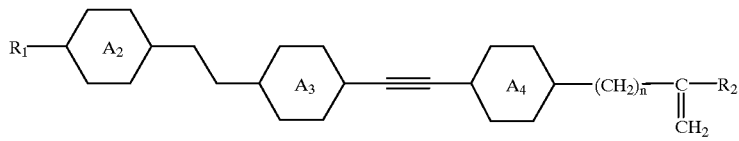
(1-31)
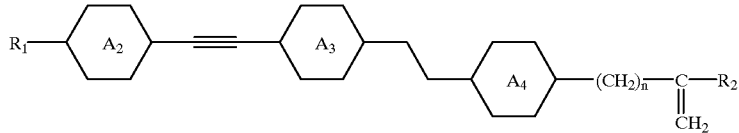
(1-32)
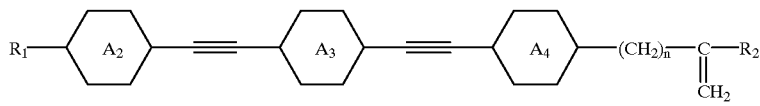
(1-33)
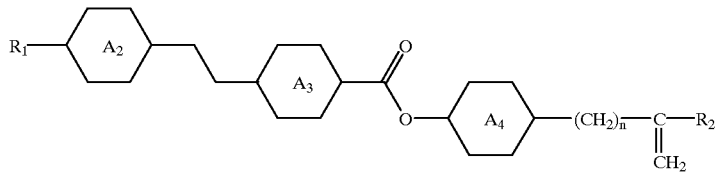
(1-34)
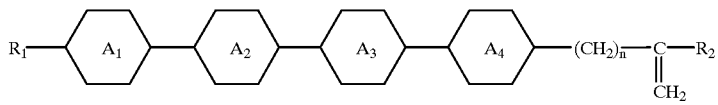
(1-35)
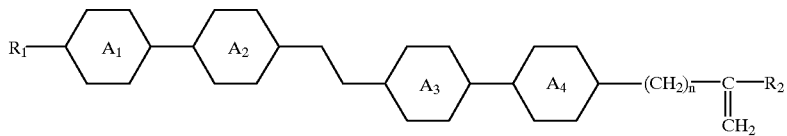
(1-36)
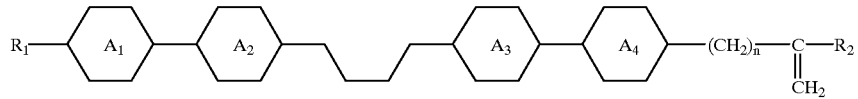
(1-37)
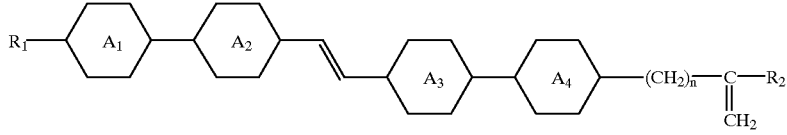
(1-38)
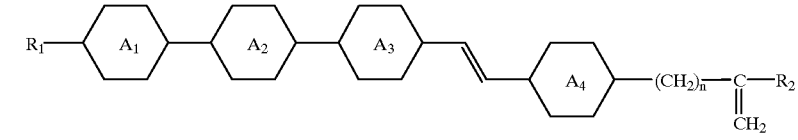
(1-39)

(1-40)
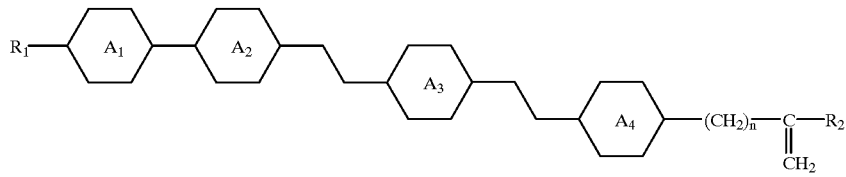
Among the compounds of the formula (1) according to the present invention, a group of compounds represented by a group of general formulae (1-41) to (1-136) are more preferred. $R_1$, $R_2$, and n are as defined above. $W_3$, $W_4$, $W_5$, $W_6$, $W_7$, $W_8$, $W_9$, and $W_{10}$ represent a fluorine or a chlorine atom.
(1-41)
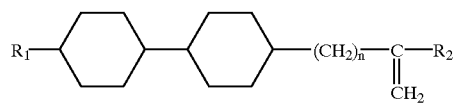
(1-42)
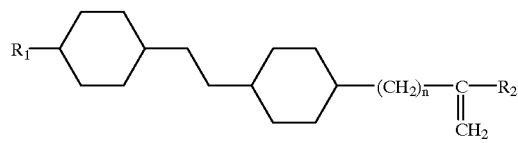
(1-43)
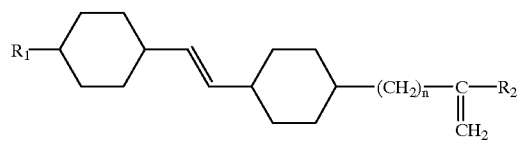
(1-44)
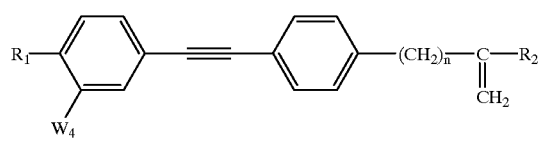
(1-45)
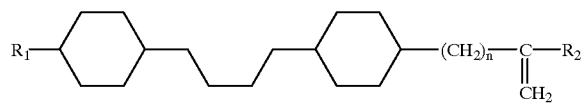
(1-46)
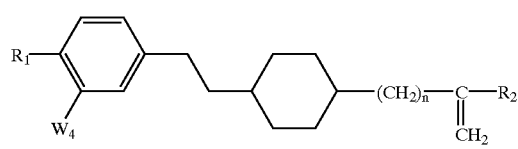
(1-47)
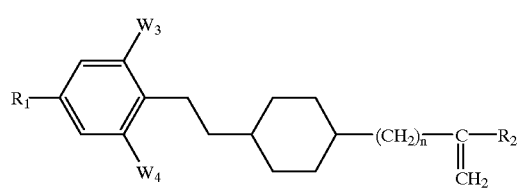

-continued
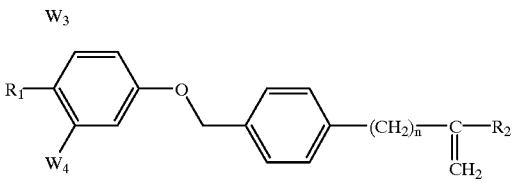
(1-48)
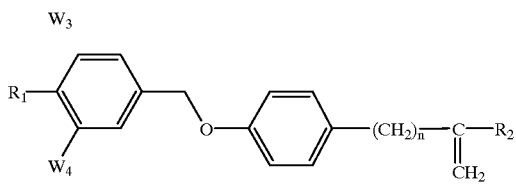
(1-49)
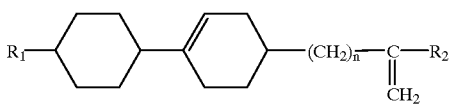
(1-50)
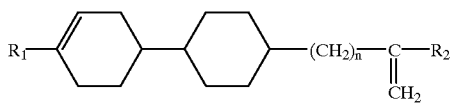
(1-51)
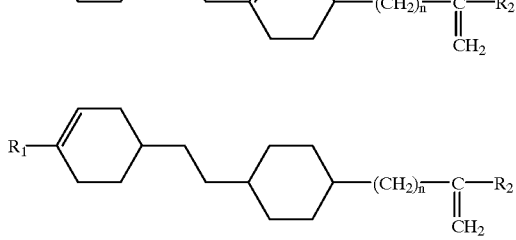
(1-52)
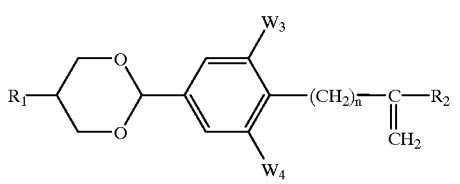
(1-53)
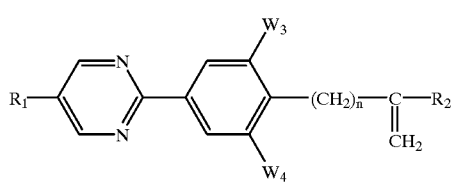
(1-54)
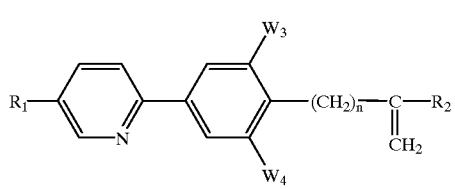
(1-55)

-continued
(1-57)
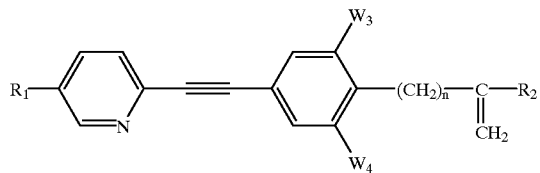
(1-58)
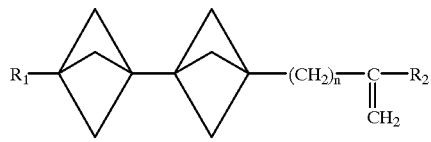
(1-59)
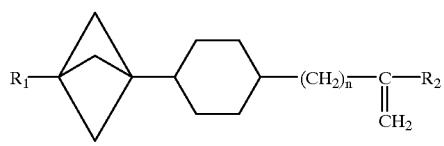
(1-60)
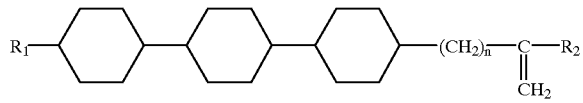
(1-61)
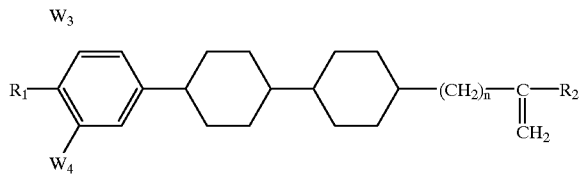
(1-62)
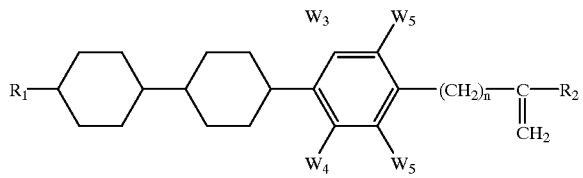
(1-63)
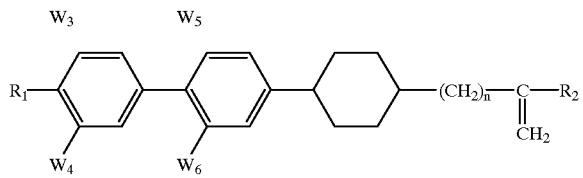
(1-64)
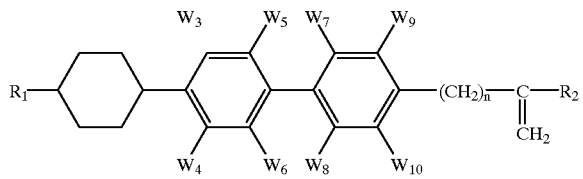
(1-65)
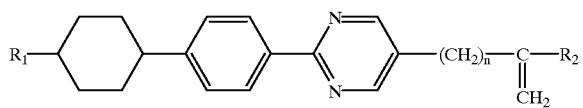

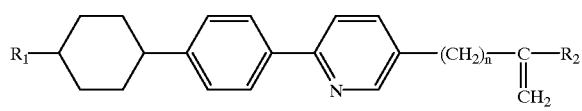
(1-66)
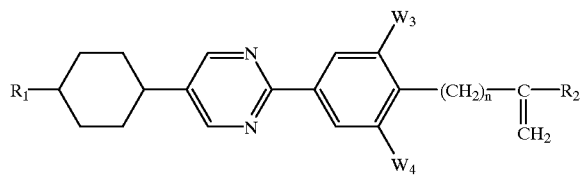
(1-67)
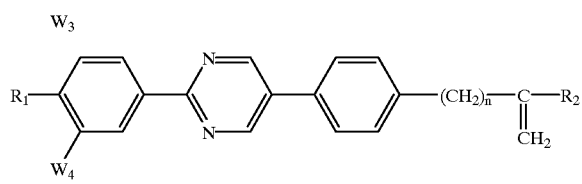
(1-68)
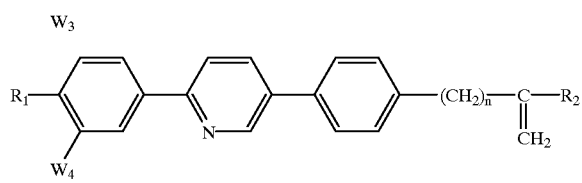
(1-69)
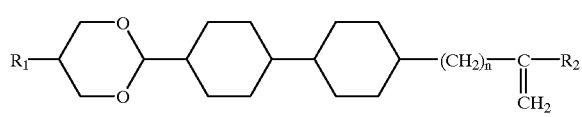
(1-70)
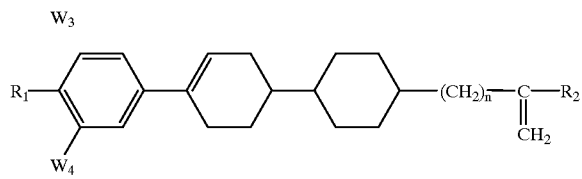
(1-71)
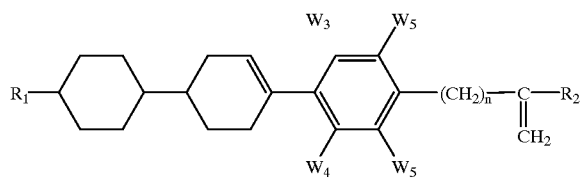
(1-72)
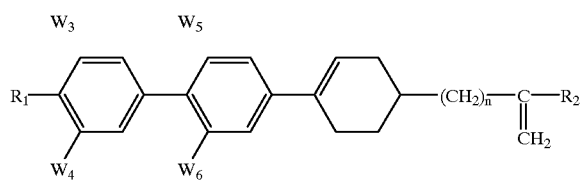
(1-73)

(1-74)
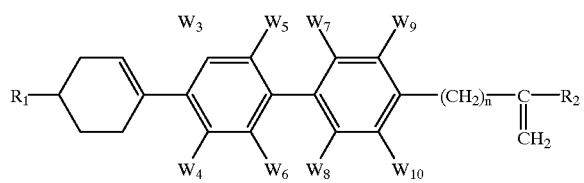
(1-75)
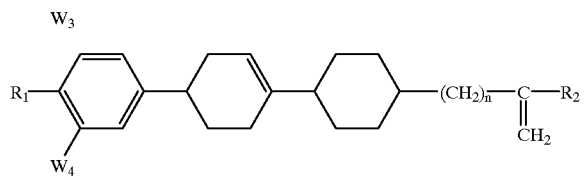
(1-76)
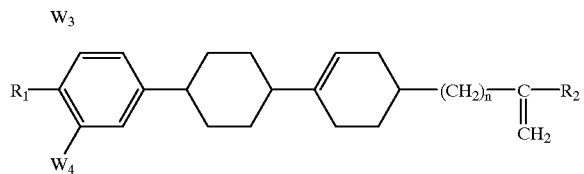
(1-77)
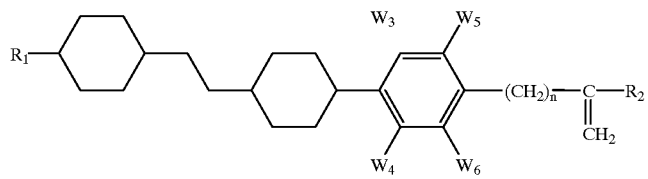
(1-78)
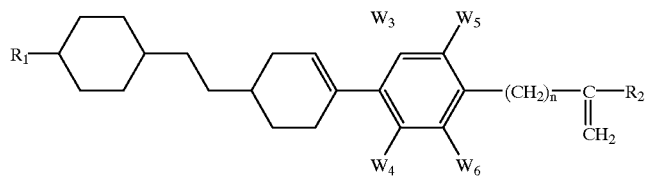
(1-79)
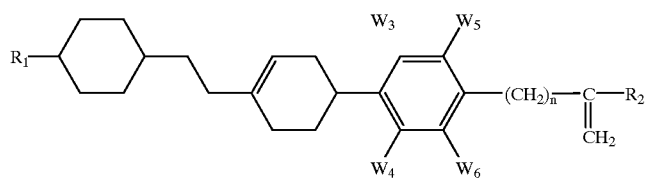
(1-80)
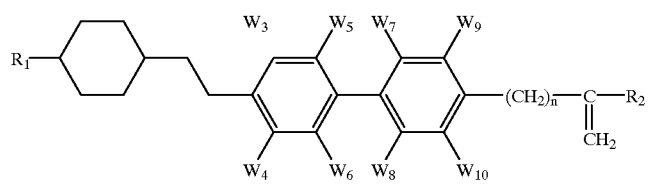
(1-81)
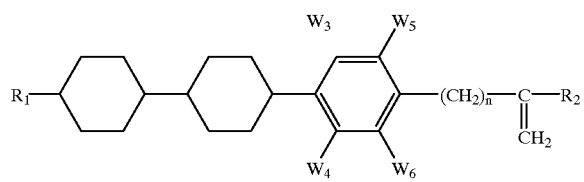

-continued
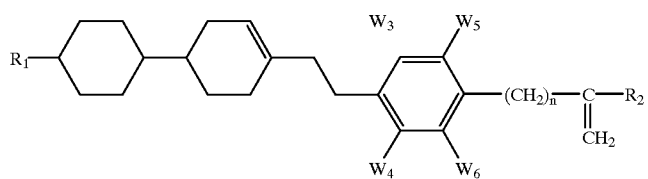
(1-82)
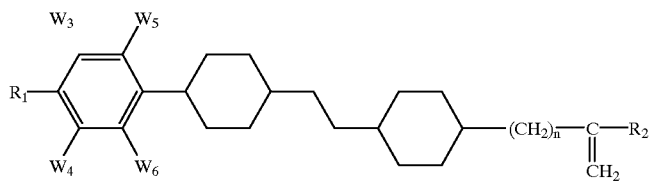
(1-83)
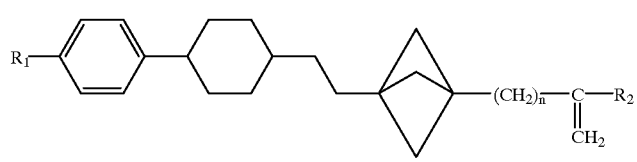
(1-84)
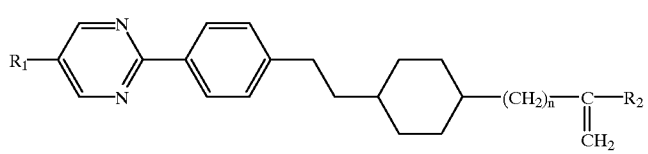
(1-85)
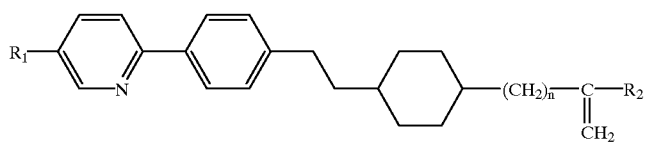
(1-86)
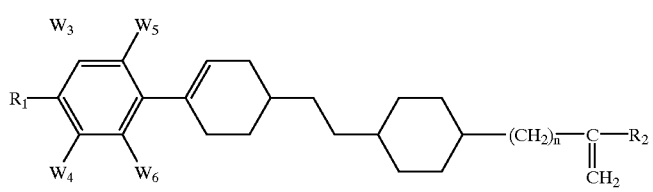
(1-87)
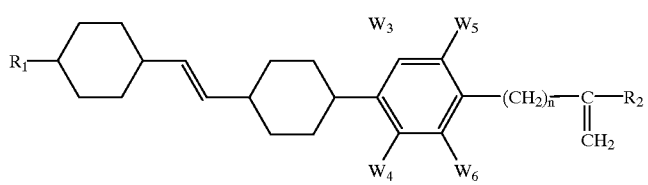
(1-88)
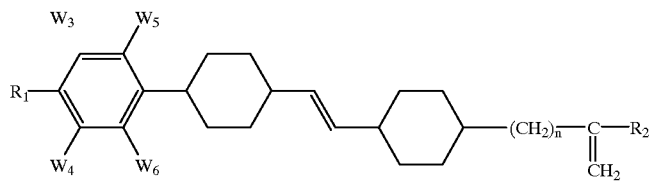
(1-89)

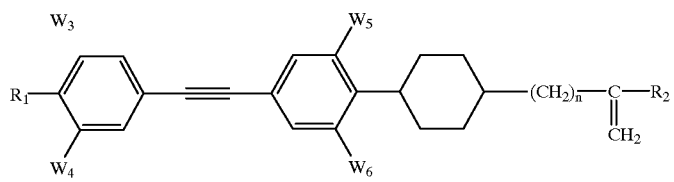
(1-90)
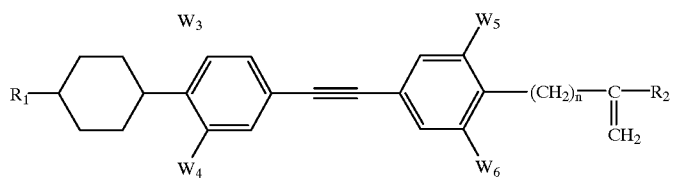
(1-91)
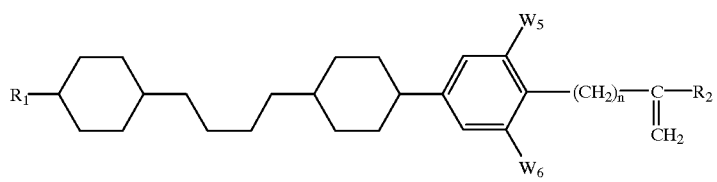
(1-92)
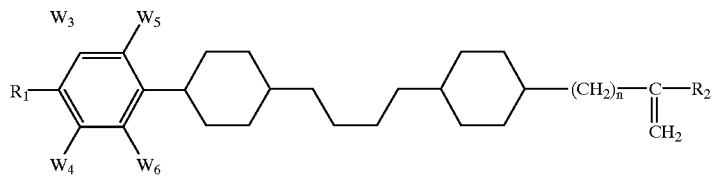
(1-93)
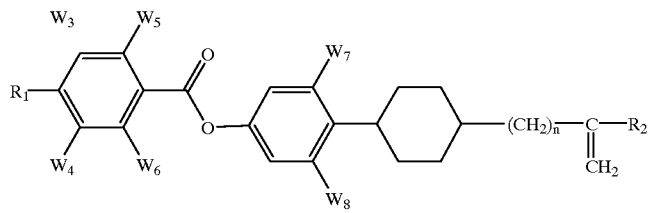
(1-94)
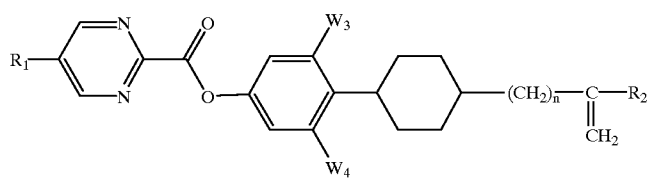
(1-95)
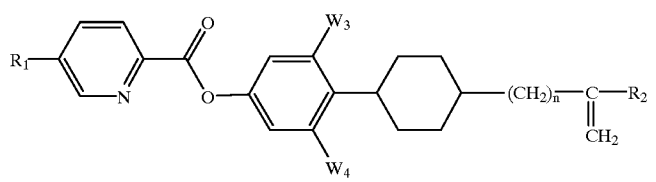
(1-96)
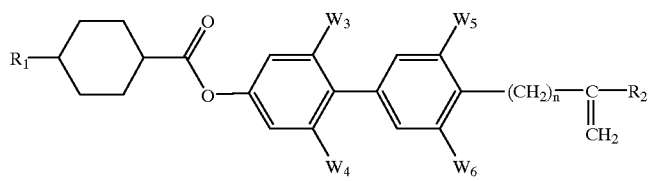
(1-97)

-continued
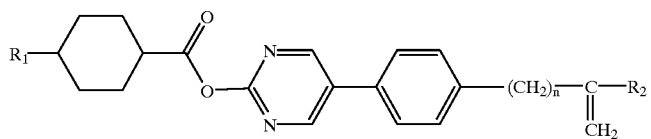
(1-98)
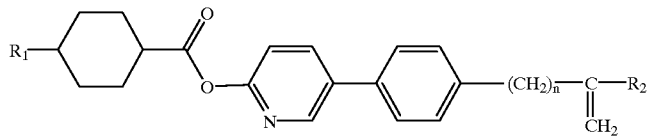
(1-99)
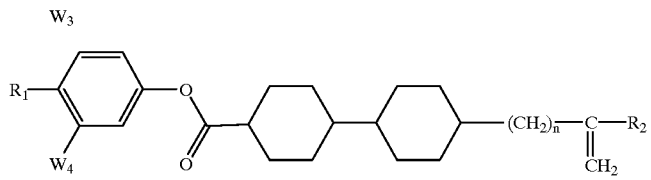
(1-100)
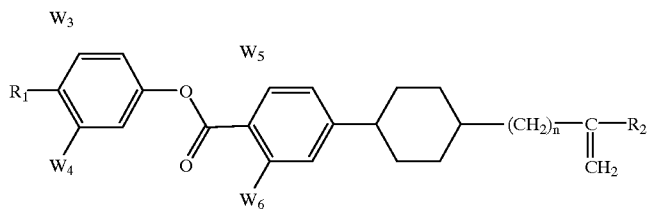
(1-101)
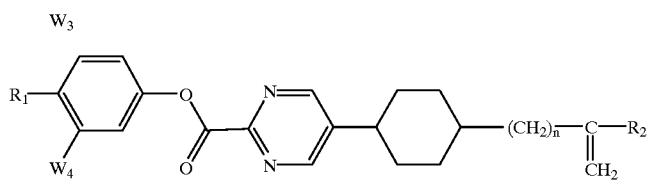
(1-102)
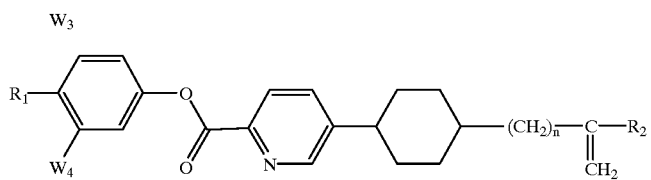
(1-103)
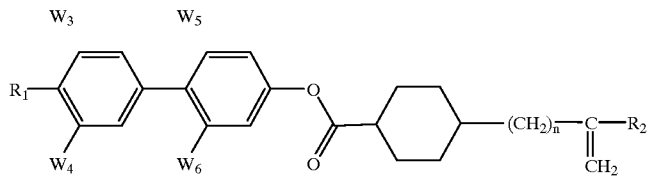
(1-104)
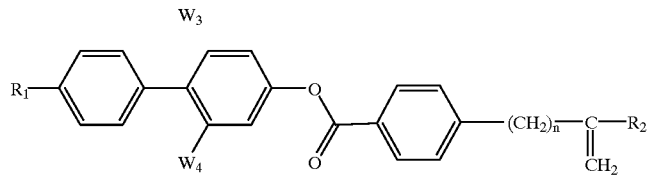
(1-105)

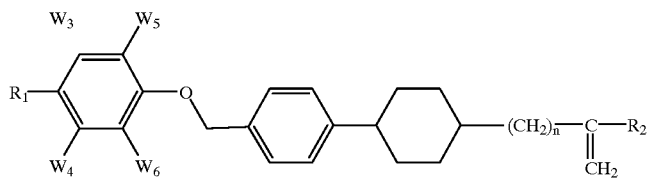
(1-106)
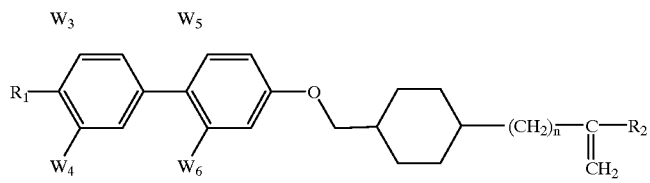
(1-107)
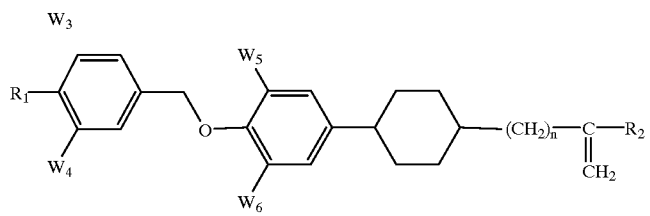
(1-108)
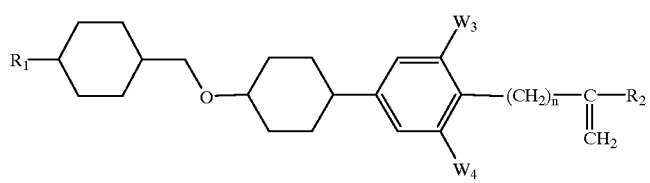
(1-109)
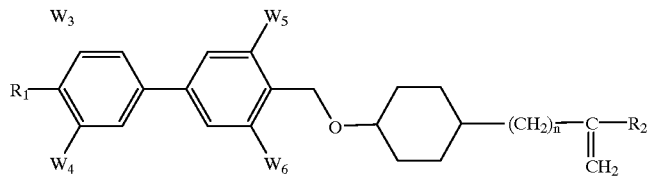
(1-110)
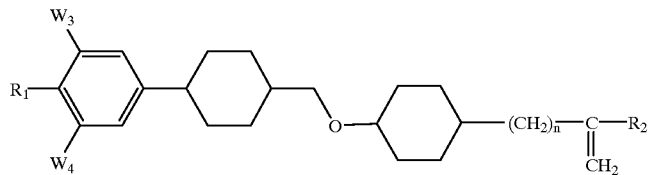
(1-111)
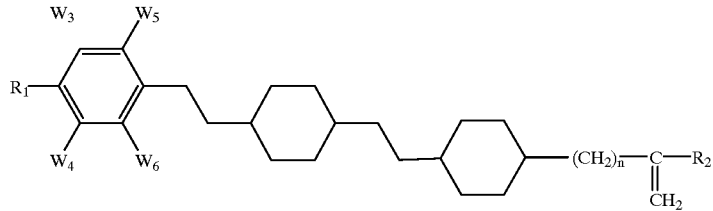
(1-112)

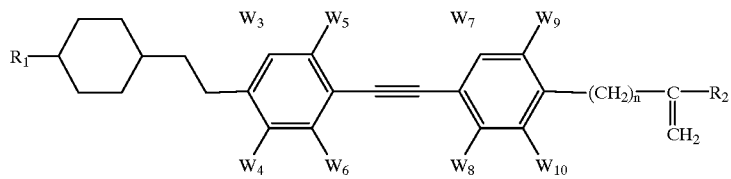
(1-113)
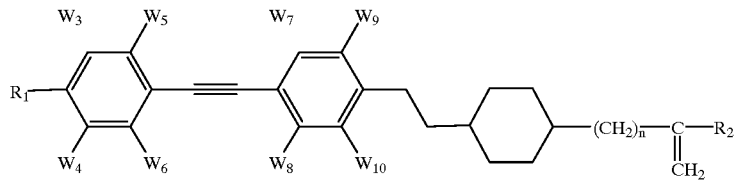
(1-114)
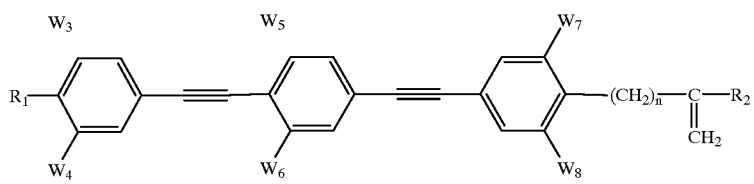
(1-115)
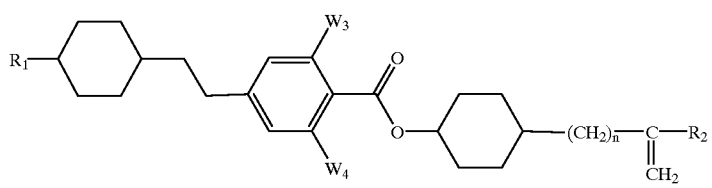
(1-116)
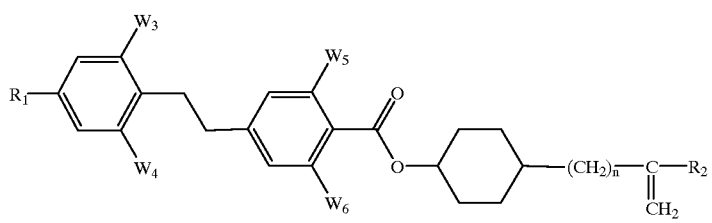
(1-117)
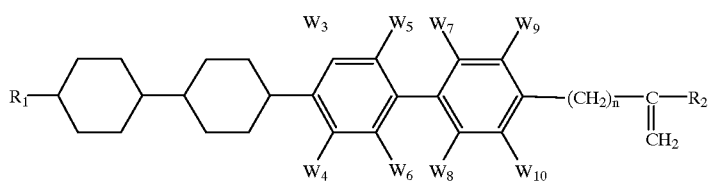
(1-118)
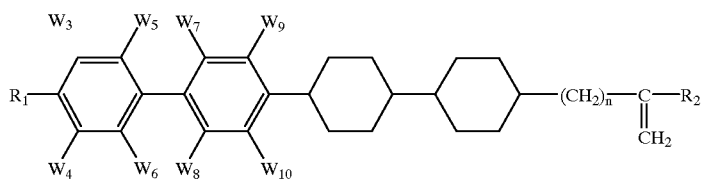
(1-119)

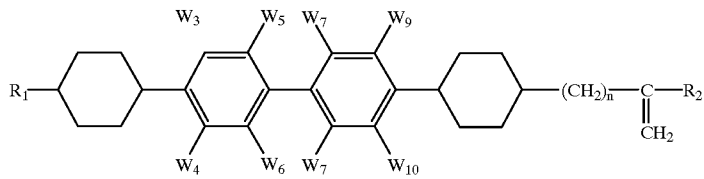
(1-120)
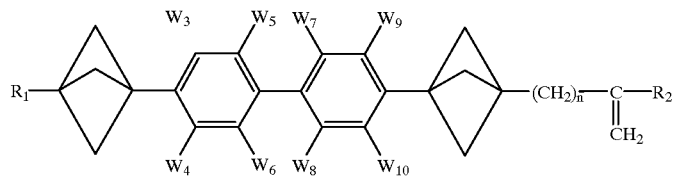
(1-121)
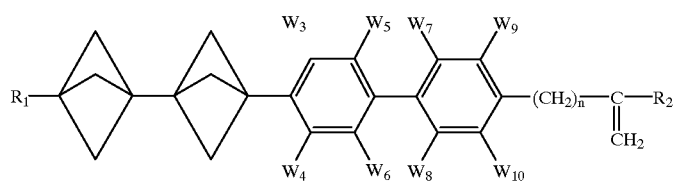
(1-122)
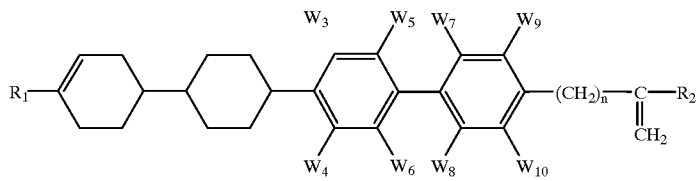
(1-123)
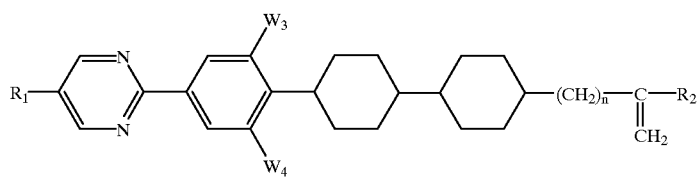
(1-124)
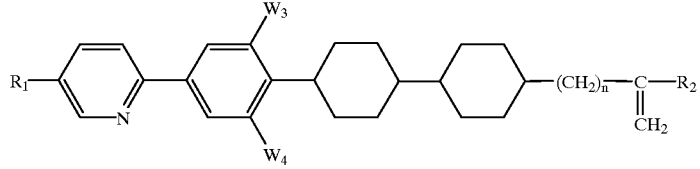
(1-125)
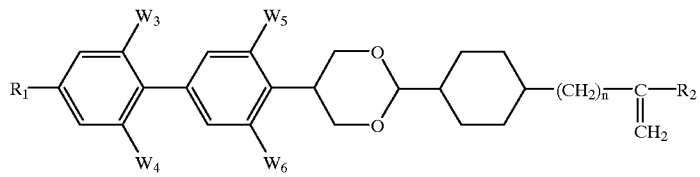
(1-126)
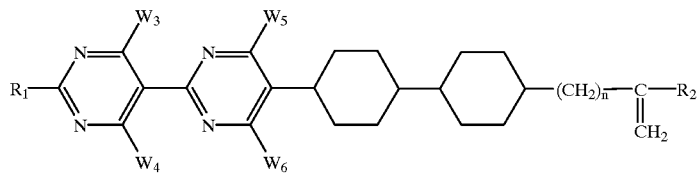
(1-127)

-continued
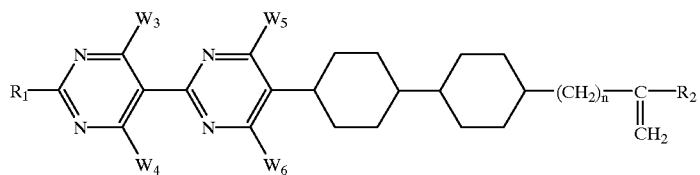
(1-128)
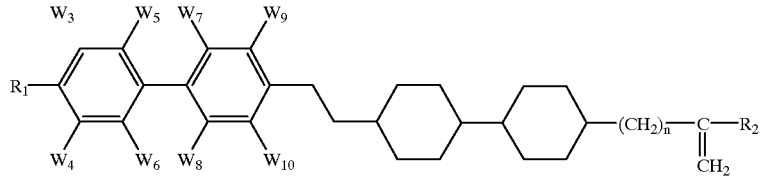
(1-129)
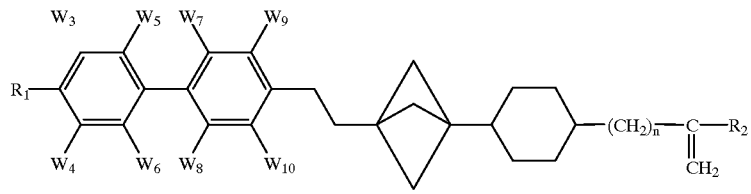
(1-130)
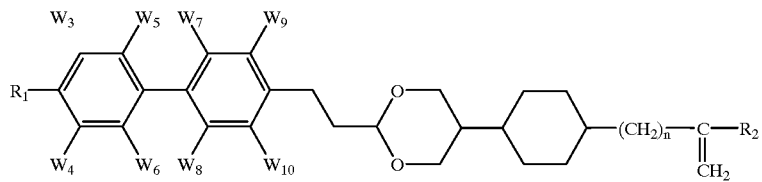
(1-131)
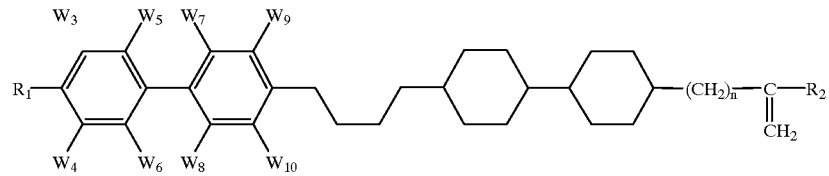
(1-132)
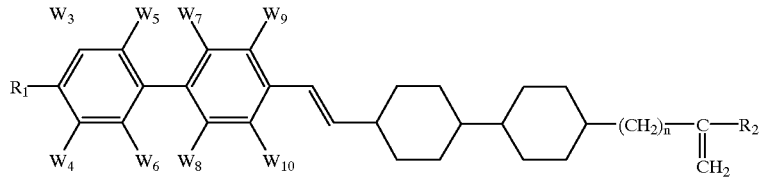
(1-133)
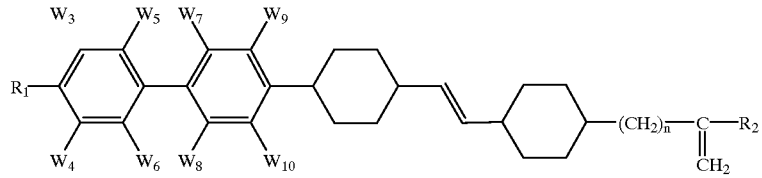
(1-134)

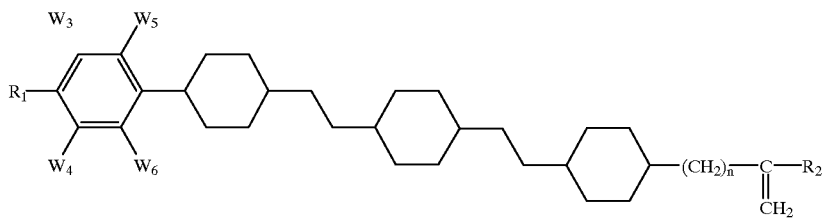

(1-135)

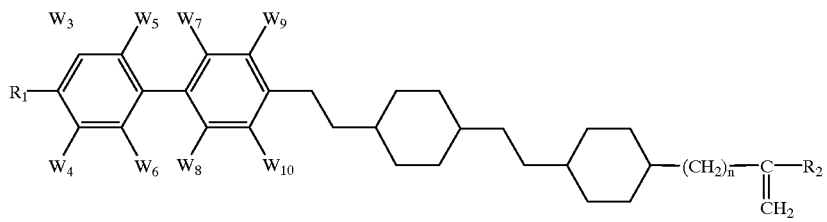

(1-136)

All the compounds having a side chain including an exo-methylene site "—$(CH_2)_n$—$C(=CH_2)$—$R_2$" have good properties so far as requirements specified in the general formula (1) are met. $R_2$ represents an alkyl group having 1 to 10 carbon atoms or a straight-chain or branched hydrocarbon residue.

Preferred examples of the side chain "—$(CH_2)_n$—$C(=CH_2)$—$R_2$" include:

1-methyl-1-ethenyl(isopropenyl), 1-ethyl-1-ethenyl, 1-propyl-1-ethenyl, 1-isopropyl-1-ethenyl, 1-butyl-1-ethenyl, 1-isobutyl-1-ethenyl, 1-pentyl-1-ethenyl, 1-isopentyl-1-ethenyl, 1-(2-methylbutyl)-1-ethenyl, 1-hexyl-1-ethenyl, 1-isohexyl-1-ethenyl, 1-(2-methylpentyl)-1-ethenyl, 1-(3-methylpentyl)-1-ethenyl, 1-heptyl-1-ethenyl, 1-octyl-1-ethenyl, 1-nonyl-1-ethenyl, 1-decyl-1-ethenyl, 2-methyl-2-propenyl, 2-ethyl-2-propenyl, 2-propyl-2-propenyl, 2-isopropyl-2-propenyl, 2-butyl-2-propenyl, 2-isobutyl-2-propenyl, 2-pentyl-2-propenyl, 2-isopentyl-2-propenyl, 2-(2-methylbutyl)-2-propenyl, 2-hexyl-2-propenyl, 2-isohexyl-2-propenyl, 2-(2-methylpentyl)-2-propenyl-2-(3-methylpentyl)-2-propenyl, 2-heptyl-2-propenyl, 2-octyl-2-propenyl, 2-nonyl-2-propenyl, 2-decyl-2-propenyl, 3-methyl-3-butenyl, 3-ethyl-3-butenyl, 3-propyl-3-butenyl, 3-isopropyl-3-butenyl, 3-butyl-3-butenyl, 3-isobutyl-3-butenyl, 3-pentyl-3-butenyl, 3-isopentyl-3-butenyl, 3-(2-methylbutyl)-3-butenyl, 3-hexyl-3-butenyl, 3-isohexyl-3-butenyl, 3-(2-methylpentyl)-3-butenyl, 3-(3-methylpentyl)-3-butenyl, 3-heptyl-3-butenyl, 3-octyl-3-butenyl, 3-nonyl-3-butenyl, 3-decyl-3-butenyl, 4-methyl-4-pentenyl, 4-ethyl-4-pentenyl, 4-propyl-4-pentenyl, 4-isopropyl-4-pentenyl, 4-butyl-4-pentenyl, 4-isobutyl-4-pentenyl, 4-pentyl-4-pentenyl, 4-isopentyl-4-pentenyl, 4-(2-methylbutyl)-4-pentenyl, 4-hexyl-4-pentenyl, 4-isohexyl-4-pentenyl, 4-(2-methylpentyl)-4-pentenyl, 4-(3-methylpentyl)-4-pentenyl, 4-heptyl-4-pentenyl, 4-octyl-4-pentenyl, 4-nonyl-4-pentenyl, 1-decyl-4-pentenyl, 5-methyl-5-hexenyl, 5-ethyl-5-hexenyl, 5-propyl-5-hexenyl, 5-isopropyl-5-hexenyl, 5-butyl-5-hexenyl, 5-isobutyl-5-hexenyl, 5-pentyl-5-hexenyl, 5-isopentyl-5-hexenyl, 5-(2-methylbutyl)-5-hexenyl, 5-hexyl-5-hexenyl, 5-isohexyl-5-hexenyl, 5-(2-methylpentyl)-5-hexenyl, 5-(3-methylpentyl)-5-hexenyl, 5-heptyl-5-hexenyl, 5-octyl-5-hexenyl, 5-nonyl-5-hexenyl, 5-decyl-5-hexenyl, 6-methyl-6-heptenyl, 6-ethyl-6-heptenyl, 6-propyl-6-heptenyl, 6-isopropyl-6-heptenyl, 6-butyl-6-heptenyl, 6-isobutyl-6-heptenyl, 6-pentyl-6-heptenyl, 6-isopentyl-6-heptenyl, 6-(2-methylbutyl)-6-heptenyl, 6-hexyl-6-heptenyl, 6-isohexyl-6-heptenyl, 6-(2-methylpentyl)-6-heptenyl, 6-(3-methylpentyl)-6-heptenyl, 6-heptyl-6-heptenyl, 6-octyl-6-heptenyl, 6-nonyl-6-heptenyl, 6-decyl-6-heptenyl, 7-methyl-7-octenyl, 7-ethyl-7-octenyl, 7-propyl-7-octenyl, 7-isopropyl-7-octenyl, 7-butyl-7-octenyl, 7-isobutyl-7-octenyl, 7-pentyl-7-octenyl, 7-isopentyl-7-octenyl, 7-(2-methylbutyl)-7-octenyl, 7-hexyl-7-octenyl, 7-isohexyl-7-octenyl, 7-(2-methylpentyl)-7-octenyl, 7-(3-methylpentyl)-7-octenyl, 7-heptyl-7-octenyl, 7-octyl-7-octenyl, 7-nonyl-7-octenyl, 7-decyl-7-octenyl, 8-methyl-8-nonenyl, 8-ethyl-8-nonenyl, 8-propyl-8-nonenyl, 8-isopropyl-8-nonenyl, 8-butyl-8-nonenyl, 8-isobutyl-8-nonenyl, 8-pentyl-8-nonenyl, 8-isopentyl-8-nonenyl, 8-(2-methylbutyl)-8-nonenyl, 8-hexyl-8-nonenyl, 8-isohexyl-8-nonenyl, 8-(2-methylpentyl)-8-nonenyl, 8-(3-methylpentyl)-8-nonenyl, 8-heptyl-8-nonenyl, 8-octyl-8-nonenyl, 8-nonyl-8-nonenyl, and 8-decyl-8-nonenyl groups.

Among them, the following groups are more preferred:

3-methyl-3-butenyl, 3-ethyl-3-butenyl, 3-propyl-3-butenyl, 3-butyl-3-butenyl, 3-pentyl-3-butenyl, 3-hexyl-3-butenyl, 3-heptyl-3-butenyl, 3-octyl-3-butenyl, 3-nonyl-3-butenyl, 3-decyl-3-butenyl, 4-methyl-4-pentenyl, 4-ethyl-4-pentenyl, 4-propyl-4-pentenyl, 4-butyl-4-pentenyl, 4-pentyl-4-pentenyl, 4-hexyl-4-pentenyl, 4-heptyl-4-pentenyl, 4-octyl-4-pentenyl, 4-nonyl-4-pentenyl, 4-decyl-4-pentenyl, 5-methyl-5-hexenyl, 5-ethyl-5-hexenyl, 5-butyl-5-hexenyl, 5-pentyl-5-hexenyl, 5-hexyl-5-hexenyl, 5-heptyl-5-hexenyl, 5-octyl-5-hexenyl, 5-nonyl-5-hexenyl, and 5-decyl-5-hexenyl groups.

Among the above groups, the following groups are more preferred from the viewpoints of low viscosity and high clearing point: 3-methyl-3-butenyl, 3-ethyl-3-butenyl, 3-propyl-3-butenyl, 3-butyl-3-butenyl, 3-pentyl-3-butenyl, 4-methyl-4-pentenyl, 4-ethyl-4-pentenyl, 4-propyl-4-pentenyl, 4-butyl-4-pentenyl, 5-methyl-5-hexenyl, 5-ethyl-5-hexenyl, and 5-butyl-5-hexenyl groups.

Preferably, the liquid crystal composition of the present invention comprises 0.1 to 99.9% by weight in total of at least one member selected from the compounds represented by the formula (1) from the viewpoint of developing good properties.

More preferably, the liquid crystal composition according to the present invention comprises a first component containing at least one member selected from the compounds of the formula (1) and, in addition, at least one member properly selected from a group of compounds represented by the general formulae (2) to (9) according the applications of the liquid crystal composition.

Preferred examples of compounds, used in the present invention, represented by the general formulae (2) to (4) include the following compounds.

(In the following formulae, $R_a$ represents an alkyl or alkoxy group.)

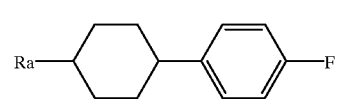
(2-1)

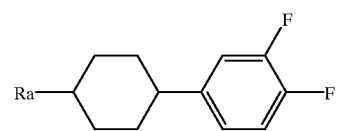
(2-2)

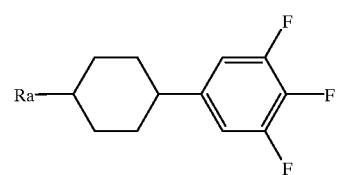
(2-3)

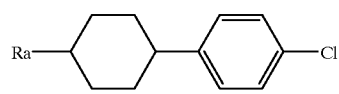
(2-4)

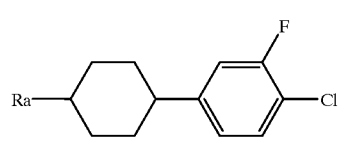
(2-5)

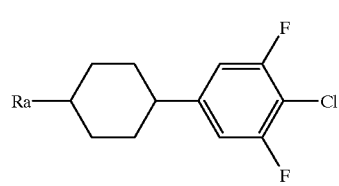
(2-6)

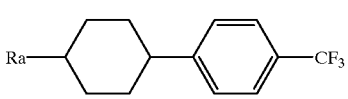
(2-7)

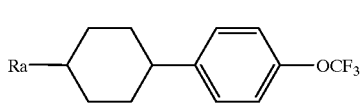
(2-8)

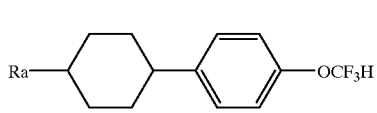
(2-9)

-continued

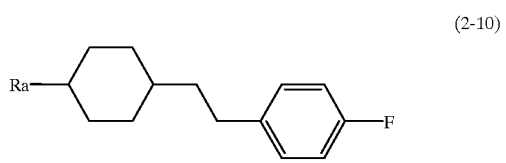
(2-10)

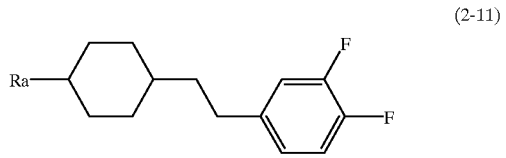
(2-11)

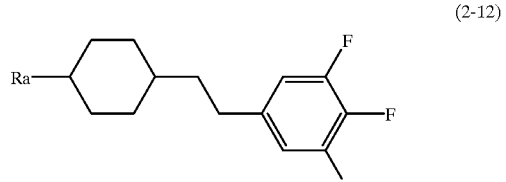
(2-12)

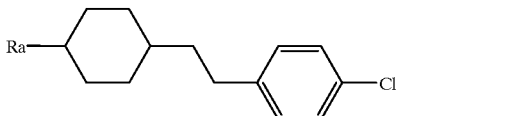
(2-13)

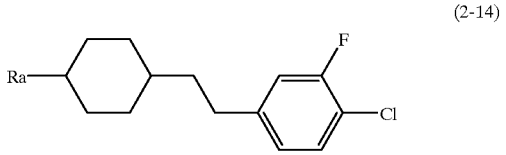
(2-14)

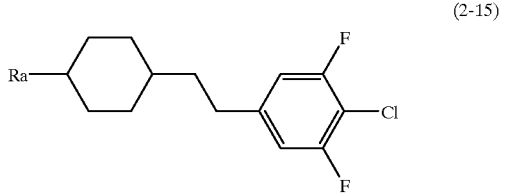
(2-15)

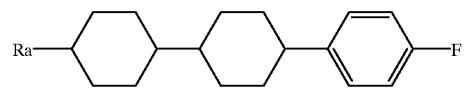
(3-1)

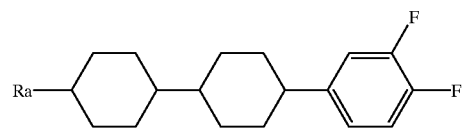
(3-2)

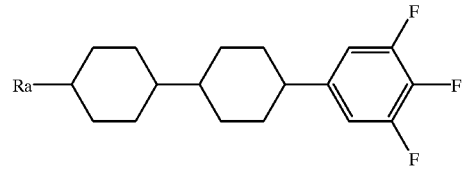
(3-3)

-continued
(3-4) 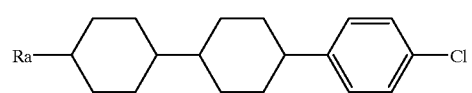
(3-5) 
(3-6) 
(3-7) 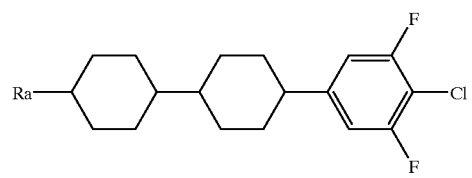
(3-8)
(3-9) 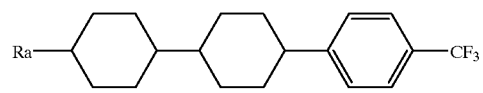
(3-10) 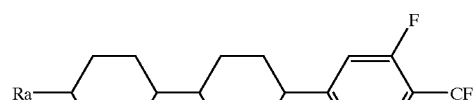
(3-11) 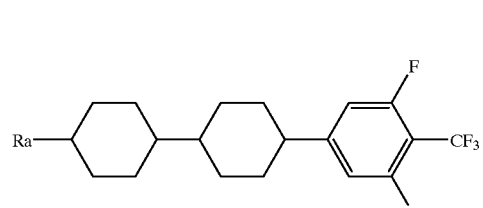
(3-12)
(3-13) 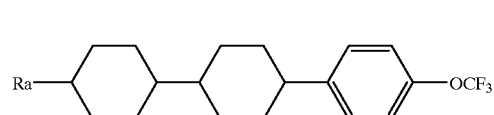
-continued
(3-14) 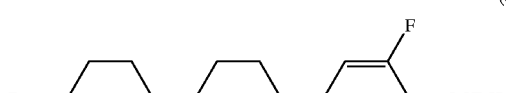
(3-15) 
(3-16) 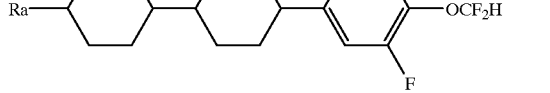
(3-17) 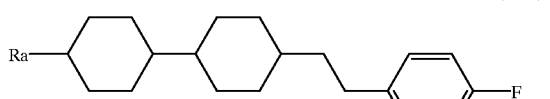
(3-18) 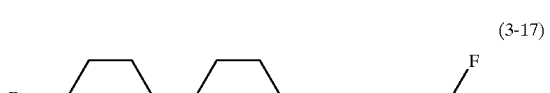
(3-19) 
(3-20) 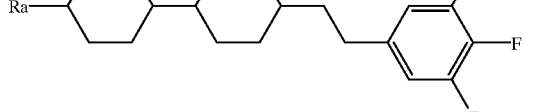
(3-21) 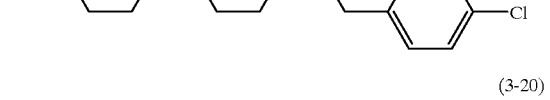
(3-22) 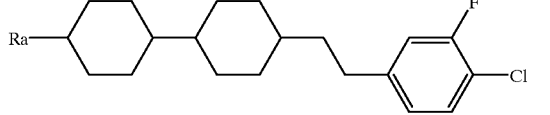

(3-23)
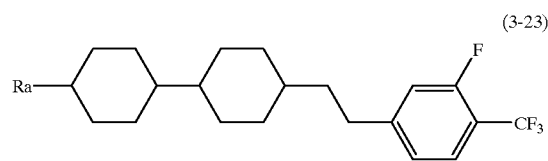
(3-24)
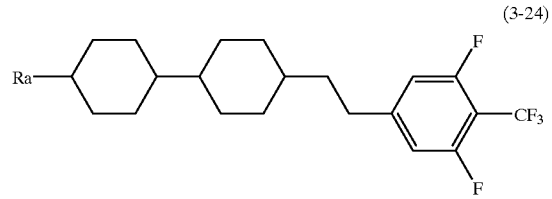
(3-25)
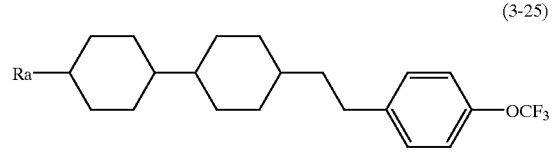
(3-26)
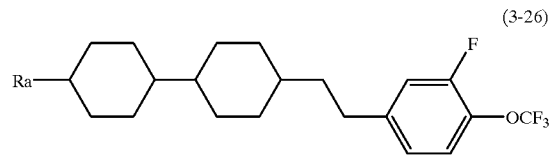
(3-27)
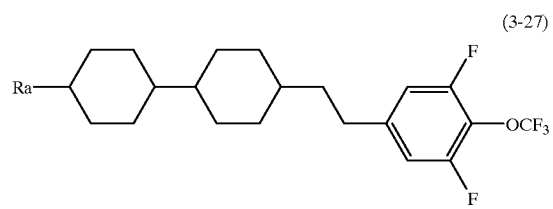
(3-28)
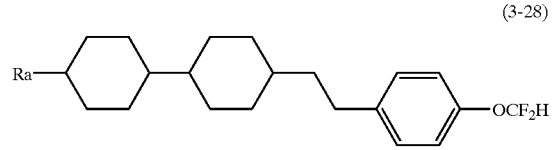
(3-29)
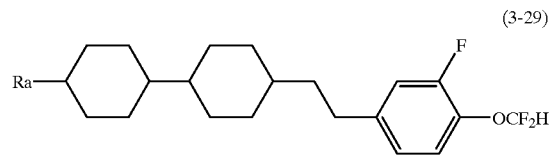
(3-30)
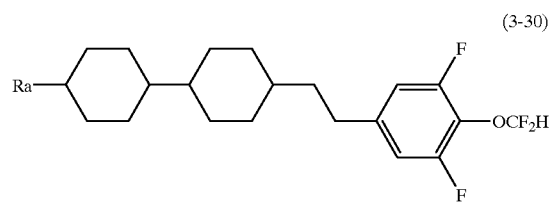
(3-31)
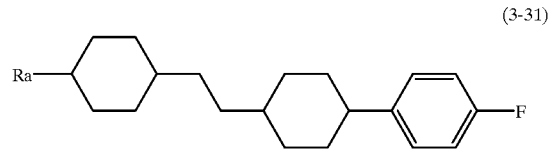
(3-32)
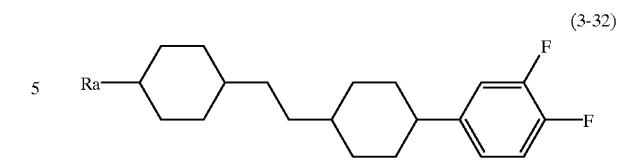
(3-33)
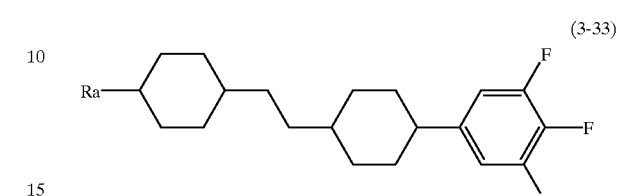
(3-34)
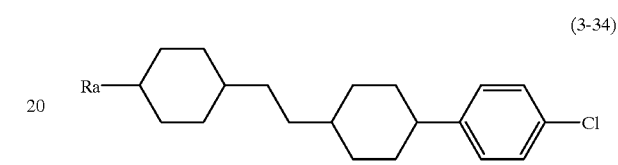
(3-35)
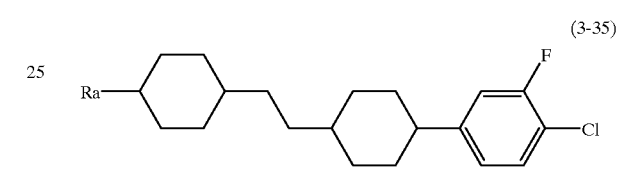
(3-36)
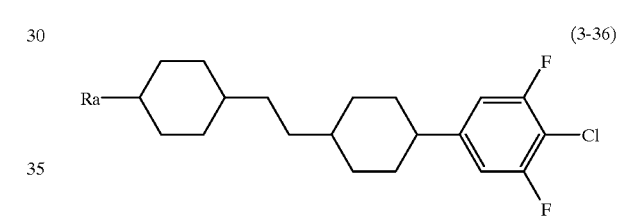
(3-37)
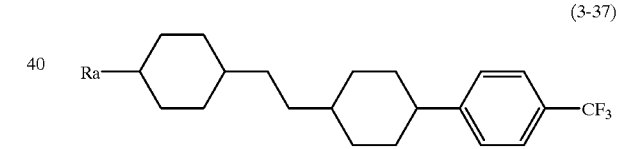
(3-38)
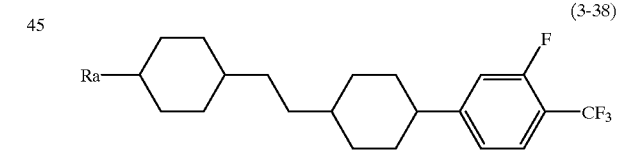
(3-39)
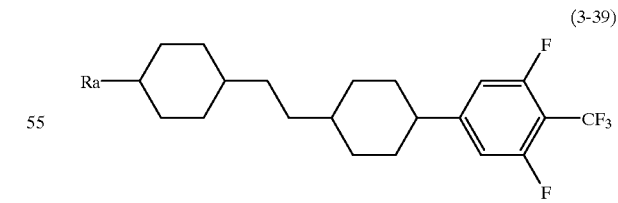
(3-40)
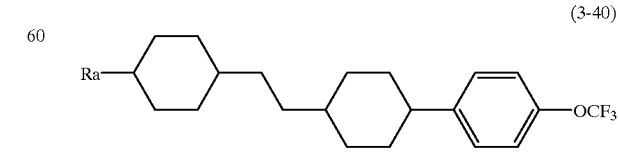

Chemical Structure Diagrams

Page contains chemical structures labeled (3-41) through (3-48) and (4-1) through (4-12), showing various liquid crystal compounds with Ra substituents on cyclohexane rings connected to aromatic rings with fluorine, chlorine, OCF₃, OCF₂H, and CF₃ substituents.

(4-13) 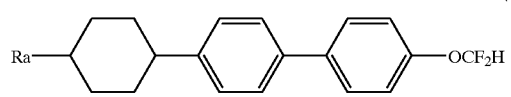
(4-14) 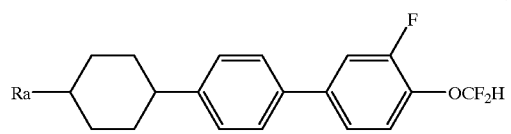
(4-15) 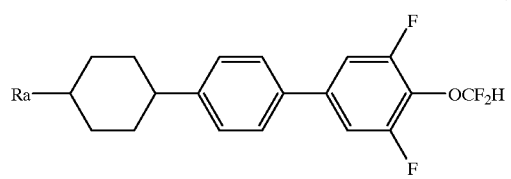
(4-16) 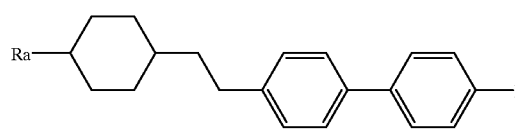
(4-17) 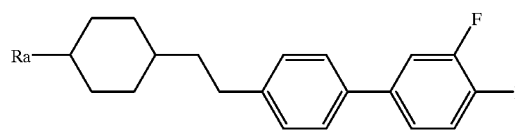
(4-18) 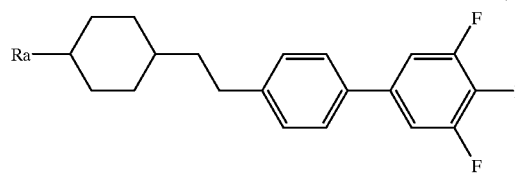
(4-19) 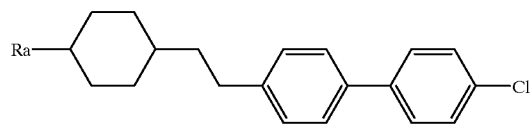
(4-20) 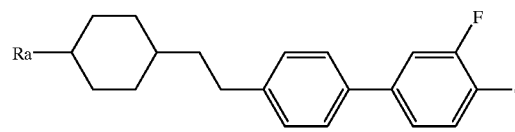
(4-21) 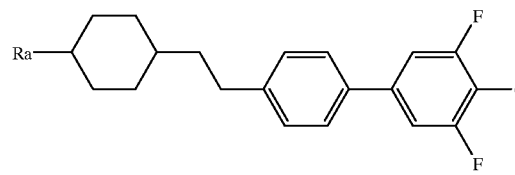
(4-22) 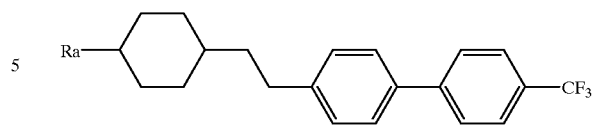
(4-23) 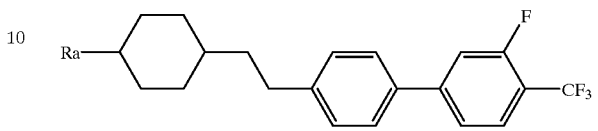
(4-24) 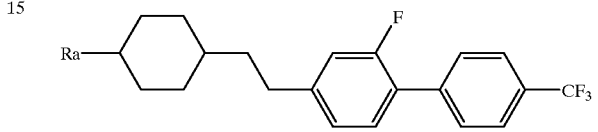
(4-25) 
(4-26) 
(4-27) 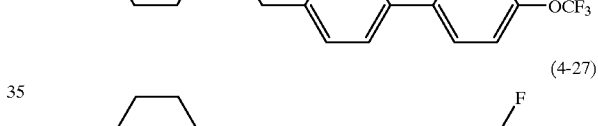
(4-28) 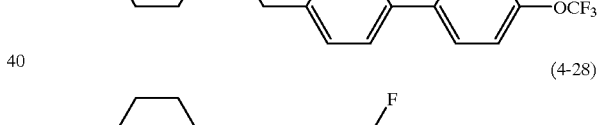
(4-29) 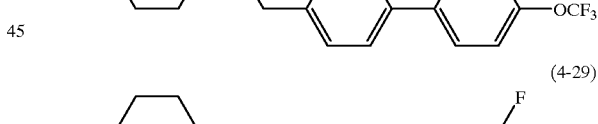
(4-30) 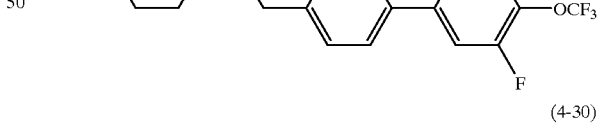
(4-31) 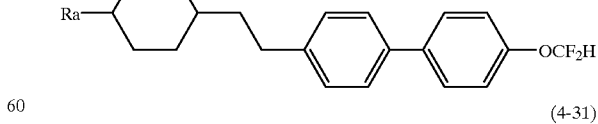

-continued (4-32) 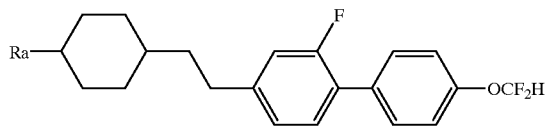

(4-33) 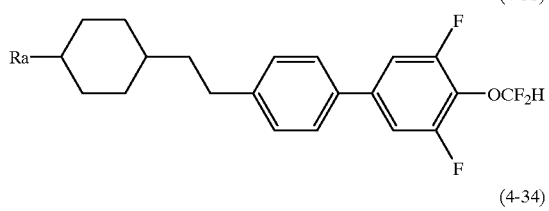

(4-34)

(4-35) 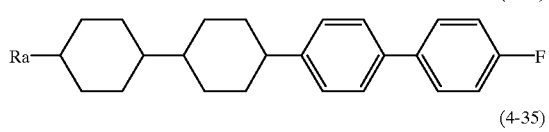

(4-36) 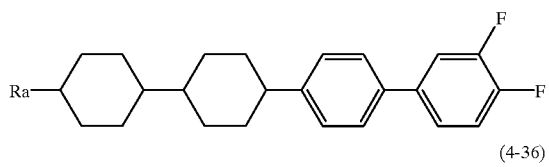

(4-37) 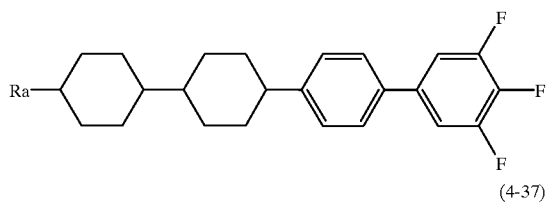

(4-38) 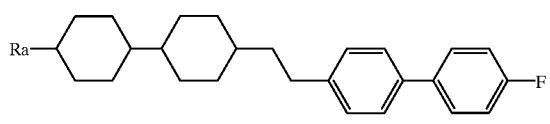

(4-39) 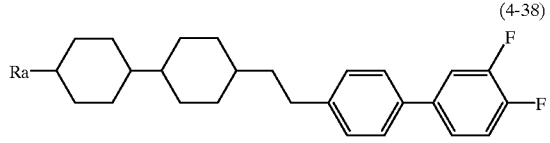

(4-40) 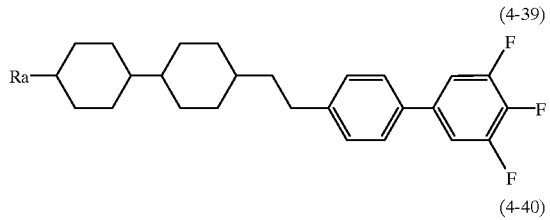

(4-41) 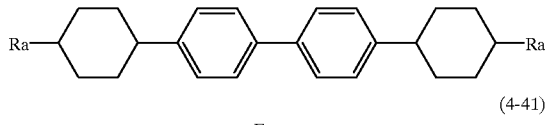

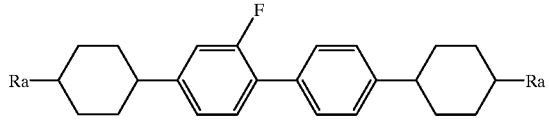

The compounds represented by the general formulae (2) to (4) have positive anisotropy of dielectric constant and possess excellent thermal stability and chemical stability and, hence, are indispensable to the preparation of liquid crystal compositions particularly for TFT (AM-LCD) where high voltage retention or high specific resistance are required.

The amount of the compounds represented by the general formulae (2) to (4), when used in the preparation of a liquid crystal composition for TFT, may be in the range of from 1 to 99% by weight based on the total weight of the liquid crystal composition. It is preferably in the range of from 10 to 97% by weight, more preferably in the range of from 40 to 95% by weight. In this case, the compounds represented by the general formulae (5) to (9) may constitute a part of the liquid crystal composition. The compounds represented by the general formulae (2) to (4) may be used also in the preparation of liquid crystal compositions for STN display system or conventional TN display systems.

Examples of preferred compounds represented by the general formulae (5) to (7) according to the present invention include the following compounds.

(In the following formulae, $R_b$, $R_c$, and $R_d$ represent an alkyl or alkenyl group and R' represents α,ω-alkylene.)

(5-1) 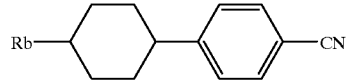

(5-2) 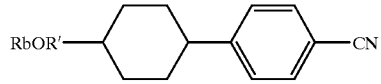

(5-3) 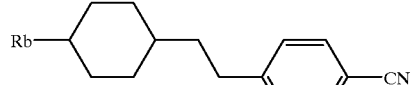

(5-4) 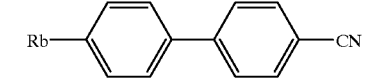

(5-5) 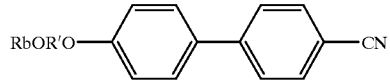

(5-6) 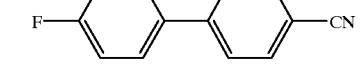

(5-7) 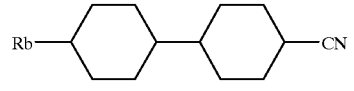

(5-8) 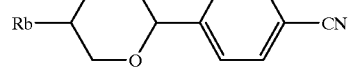

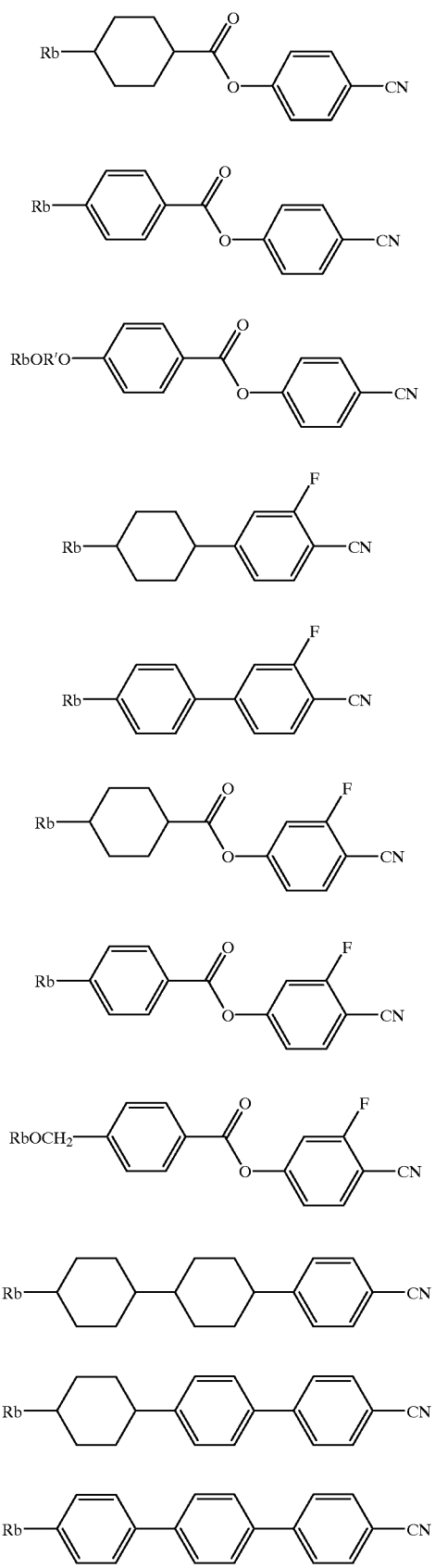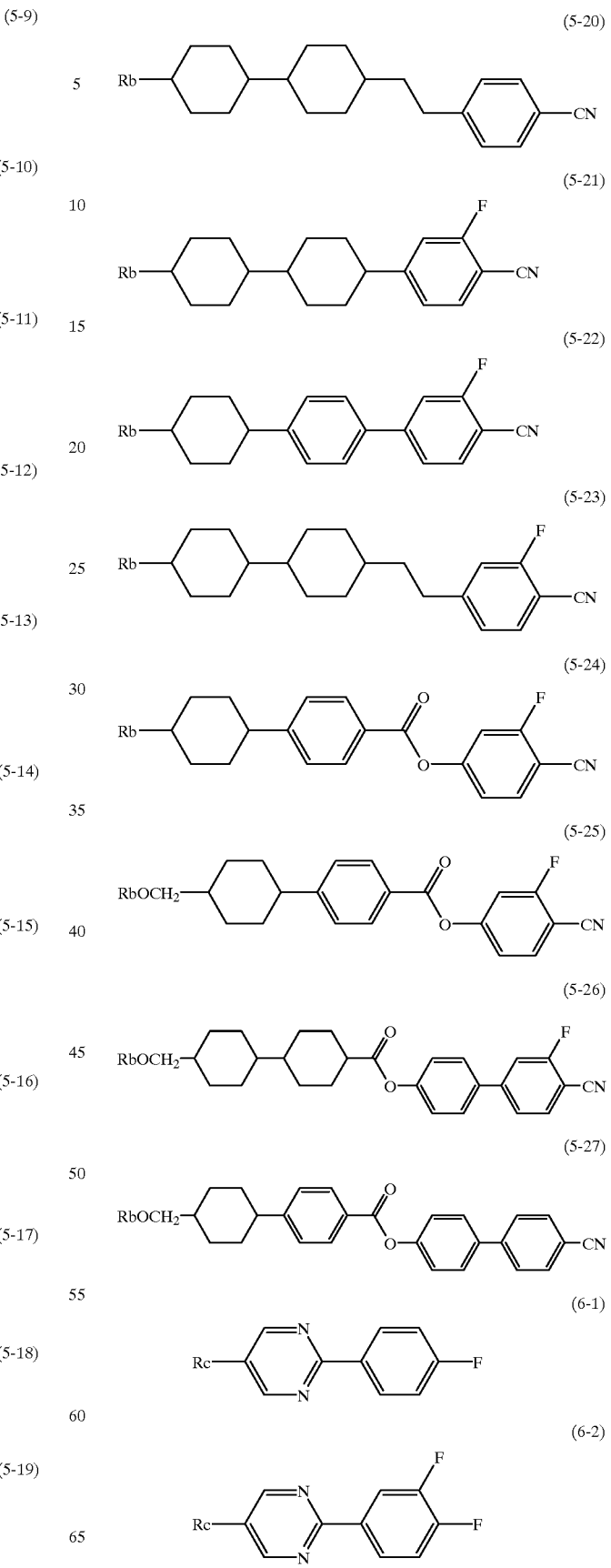

(6-3) 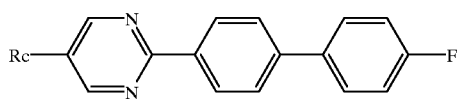

(7-1) 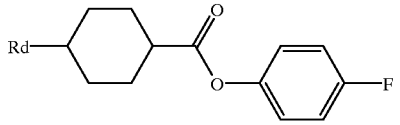

(7-2) 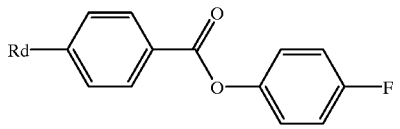

(7-3) 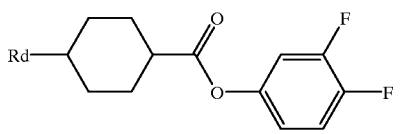

(7-4) 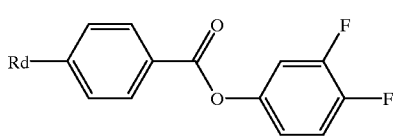

(7-5) 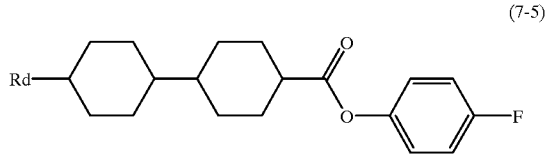

(7-6) 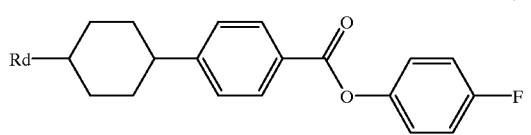

(7-7) 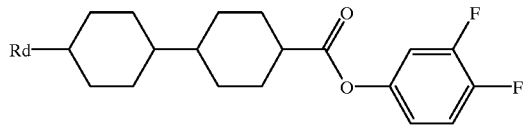

(7-8) 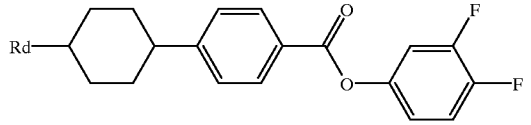

(7-9) 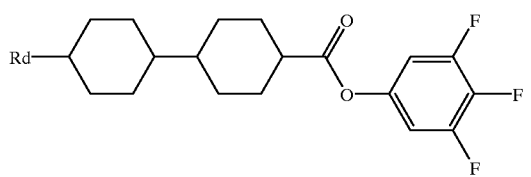

(7-10) 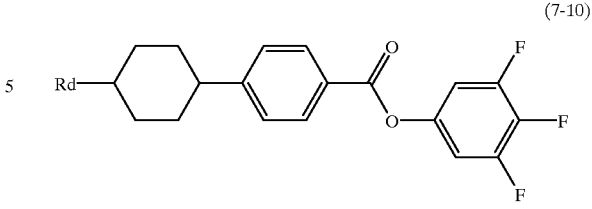

(7-11) 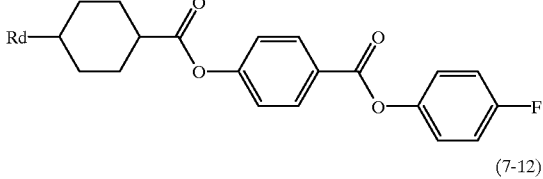

(7-12) 

(7-13) 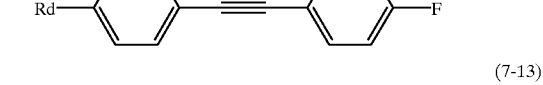

The compounds represented by the general formulae (5) to (7) have large positive anisotropy of dielectric constant and are used particularly for decreasing the threshold voltage. Further, they are used also for widening the nematic range, for example, for the purposes of modifying the viscosity, regulating the anisotropy of refractive index, and increasing the clearing point. It is also possible to use them for improving the steepness of the threshold voltage.

Examples of preferred compounds represented by the general formulae (8) to (9) according to the present invention include the following compounds.

(In the following formulae, $R_e$, $R_f$, $R_g$, and $R_h$ represent an alkyl or alkenyl group.)

(8-1) 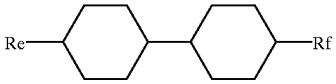

(8-2) 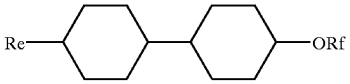

(8-3) 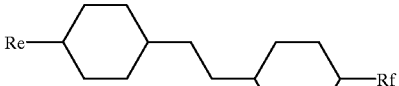

(8-4) 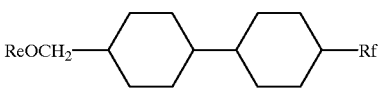

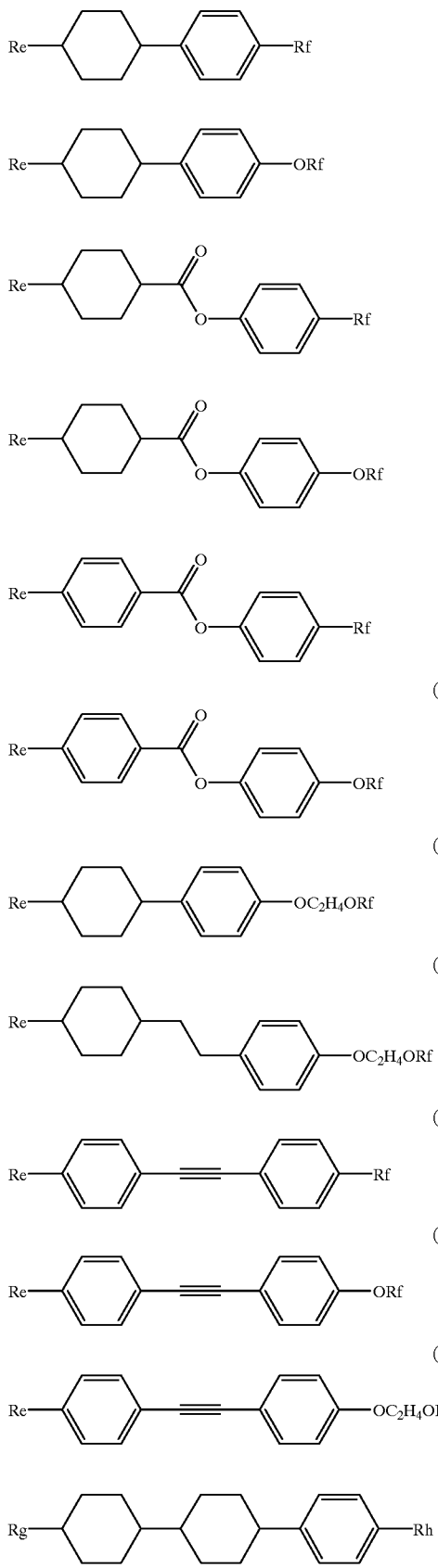
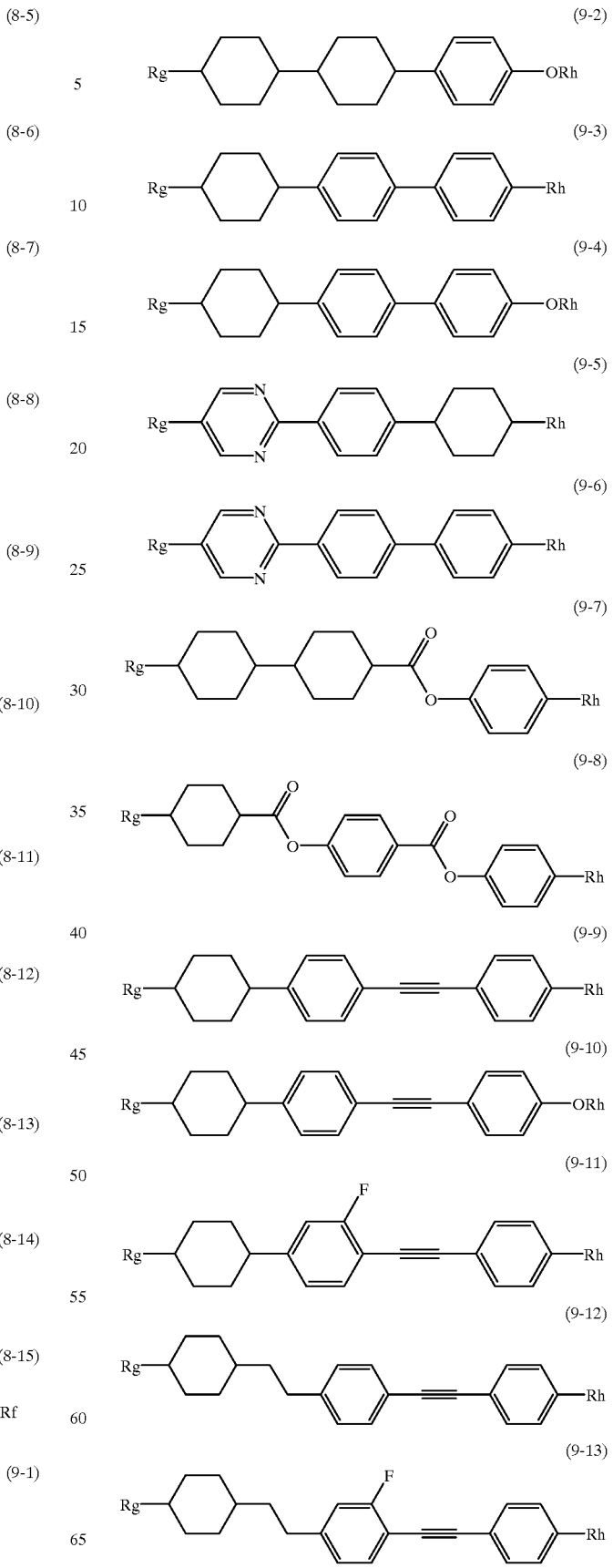

-continued (9-14)

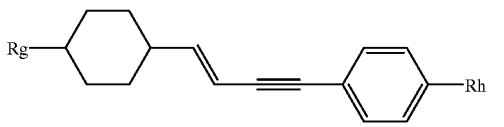

The compounds represented by the following formulae (8) and (9) have negative or somewhat positive anisotropy of dielectric constant. The compounds represented by the general formula (8) are mainly used for lowering the viscosity and/or regulating the anisotropy of refractive index. On the other hand, the compounds represented by the general formula (9) are used for widening the nematic range, for example, for the purposes of increasing the clearing point, and/or for regulating the anisotropy of refractive index.

The compounds represented by the general formulae (5) to (9) are indispensable particularly to the preparation of liquid crystal compositions for STN display system and conventional TN display-system.

The amount of the compounds represented by the general formulae (5) to (9), when used in the preparation of a liquid crystal composition for conventional TN and STN display systems, may be in the range of from 1 to 99% by weight. It is preferably in the range of from 10 to 97% by weight, more preferably in the range of from 40 to 95% by weight. In this case, the compounds represented by the general formulae (2) to (4) may constitute a part of the liquid crystal composition.

The use of the liquid crystal composition according to the present invention for TFT liquid crystal display devices enables an improvement in steepness and angle of visibility. Further, the compounds represented by the formula (1) have a low viscosity and, hence, when used in liquid crystal display devices, can markedly improve the response speed.

The liquid crystal composition used according to the present invention may be prepared by a production process which is per se commonly used in the art. In general, different components are dissolved in each other at a high temperature. Alternatively, it is also possible to use a method wherein the components are dissolved in an organic solvent capable of dissolving liquid crystals used and the solvent is then distilled off.

Further, the liquid crystal material of the present invention may be modified by using suitable additives according to the contemplated applications. Such additives are well known in the art and described in detail in literature or the like. In general, additives such as, chiral dopants, are added in order to induce the helical structure of the liquid crystal to adjust the twist angle as desired, thereby preventing reverse twisting.

Furthermore, when the liquid crystal composition used according to the present invention is contemplated to be used as a liquid crystal composition for guest-host (GH) mode, dichroic dyes, such as merocyanine, styryl, azo, azomethine, azoxy, quinophthalone, anthraquinone, and tetrazine dyes, may be added to the liquid crystal composition. Furthermore, the liquid crystal composition according to the present invention can also be used as a liquid crystal composition for NCAP, which has been prepared by enmicrocapsulating a nematic liquid crystal, or a polymer dispersion type liquid crystal display device (PDLCD) represented by a polymer network liquid crystal display device (PNLCD) with a three-dimensional network polymer prepared in a liquid crystal. Furthermore, it may be used also as a liquid crystal composition for the birefringence control (ECB) mode or dynamic scattering (DS) mode.

Composition examples of nematic liquid crystal compositions, containing the compound of the present invention, thus prepared will be given below. Compound No. given in parentheses corresponds to that described in "Examples" which will be given below.

COMPOSITION EXAMPLE 1
(Compound No. 127) 4'-(4-(3-Ethyl-3-butenyl)cyclohexyl)cyclohexyl)-3,4,5,-trifluorobiphenyl 10%
5-(4-Heptylcyclohexyl)-1,2,3-trifluorobenzene 8%
5-(4-(2-(4-Propylcyclohexyl)ethyl)cyclohexyl)-1,2,3,-trifluorobenzene 7%
5-(4-(2-(4-Pentylcyclohexyl)ethyl)cyclohexyl)-1,2,3,-trifluorobenzene 7%
b 5-(4-(4-Propylcyclohexyl)cyclohexyl)-1,2,3,-trifluorobenzene 10%
5-(4-(4-Butylcyclohexyl)cyclohexyl)-1,2,3,-trifluorobenzene 5%
5-(2-(4-(4-Propylcyclohexyl)cyclohexyl)ethyl)-1,2,3,-trifluorobenzene 8%
5-(2-(4-(4-Penthylcyclohexyl)cyclohexyl)ethyl)-1,2,3,-trifluorobenzene 8%
4'-(4-Propylcyclohexyl)-3,4,5-trifluorobiphenyl 10%
4'-(4-Pentylcyclohexyl)-3,4,5-trifluorobiphenyl 10%
3,4,5-Trifluorophenyl=4-(4-propylcyclohexyl)benzoate 2%
3,4,5-Trifluorophenyl=4-(4-butylcyclohexyl)benzoate 2%
3,4,5-Trifluorophenyl=4-(4-pentylcyclohexyl)benzoate 2%
4'-(2-(4-Propylcyclohexyl)ethyl)-3,4,5-Trifluorobiphenyl 5%
4'-(2-(4-Butylcyclohexyl)ethyl)-3,4,5-Trifluorobiphenyl 6%

COMPOSITION EXAMPLE 2
(Compound No. 46) 4'-(4-(1-Butyl-1-ethenyl)cyclohexyl)-4-trifluoromethoxybiphenyl 7%
(Compound No. 50) 4'-(4-(3-Ethyl-3-butenyl)cyclohexyl)-4-trifluoromethoxybiphenyl 7%
4-(4-Heptylcyclohexyl)-1,2-difluorobenzene 4%
4-(4-Propylcyclohexyl)-1-ethoxybenzene 13%
4-(4-(4-Propylcyclohexyl)cyclohexyl)-1-fluorobenzene 5%
4-(4-(4-Ethylcyclohexyl)cyclohexyl)-1,2-difluorobenzene 12%
4-(4-(4-Propylcyclohexyl)cyclohexyl)-1,2-difluorobenzene 12%
4-(4-(4-Pentylcyclohexyl)cyclohexyl)-1,2-difluorobenzene 12%
4-(4-(2-(4-Ethylcyclohexyl)ethyl)cyclohexyl)-1,2-difluorobenzene 6%
4-(4-(2-(4-Propylcyclohexyl)ethyl)cyclohexyl)-1,2-difluorobenzene 3%
4-(4-(2-(4-Pentylcyclohexyl)ethyl)cyclohexyl)-1,2-difluorobenzene 6%
4'-(4-Ethylcyclohexyl)-3,4-difluorobiphenyl 2%
4'-(4-Propylcyclohexyl)-3,4-difluorobiphenyl 2%
4'-(4-Pentylcyclohexyl)-3,4-difluorobiphenyl 4%
4-(2-(4-Pentylcyclohexyl)ethyl)-1,2-difluorobenzene 5%

COMPOSITION EXAMPLE 3
(Compound No. 1) 4-(4-(3-Ethyl-3-butenyl)cyclohexyl)-1-propylcyclohexane 5%
(Compound No. 2) 4-(4-(2-Propyl-2-propenyl)cyclohexyl)-1-propylcyclohexane 5%
(Compound No. 39) 2-Fluoro-4-(4-(4-(3-ethyl-3-butenyl)cyclohexyl)cyclohexyl)-1-trifluoromethoxybenzene 7%
4-(4-Propylcyclohexyl)-1-ethoxybenzene 6%
4'-(4-Ethylcyclohexyl)-4-fluorobiphenyl 3%
4'-(4-Propylcyclohexyl)-4-fluorobiphenyl 3%
4'-(4-Pentylcyclohexyl)-4-fluorobiphenyl 2%

4-(4-(4-Ethylcyclohexyl)cyclohexyl)-1,2-difluorobenzene 3%
4-(4-(4-Propylcyclohexyl)cyclohexyl)-1,2-difluorobenzene 3%
4-(4-(4-Pentylcyclohexyl)cyclohexyl)-1,2-difluorobenzene 3%
4'-(4-Ethylcyclohexyl)-3,4-difluorobiphenyl 4%
4'-(4-Propylcyclohexyl)-3,4-difluorobiphenyl 4%
4'-(4-Pentylcyclohexyl)-3,4-difluorobiphenyl 8%
4'-(4-Propylcyclohexyl)-3,4,5-trifluorobiphenyl 8%
4'-(4-Pentylcyclohexyl)-3,4,5-trifluorobiphenyl 8%
4'-(2-(4-Propylcyclohexyl)ethyl)-3,4,5-trifluorobiphenyl 4%
4'-(2-(4-Pentylcyclohexyl)ethyl)-3,4,5-trifluorobiphenyl 4%
4-(4-Propylcyclohexyl)-1-methylbenzene 4%
4-(4-(4-Propylcyclohexyl)cyclohexyl)-1-methoxybenzene 4%
4-(4-(4-Propylcyclohexyl)cyclohexyl)-1-fluorobenzene 4%
4-(4-(4-Propylcyclohexyl)cyclohexyl)-1-propylbenzene 3%
4-Fluorophenyl=4-pentylcyclohexanecarboxylate 3%
4'-(2-(4-(4-Pentylcyclohexyl)cyclohexyl)ethyl)-3,4,5-trifluorobiphenyl 2%

COMPOSITION EXAMPLE 4
(Compound No. 4) 4-(4-(1-Butyl-1-ethenyl)cyclohexyl)-1-propylcyclohexane 7%
(Compound No. 39) 2-Fluoro-4-(4-(4-(3-ethyl-3-butenyl)cyclohexyl)cyclohexyl)-1-trifluoromethoxybenzene 5%
(Compound No. 50) 4'-(4-(3-Ethyl-3-butenyl)cyclohexyl)-4-trifluoromethoxybiphenyl 5%
(Compound No. 127) 4'-(4-(4-(3-Ethyl-3-butenyl)cyclohexyl)cyclohexyl)-3,4,5-trifluorobiphenyl 3%
4-(4-Propylcyclohexyl)-1-chlorobenzene 4%
4-(4-Pentylcyclohexyl)-1-chlorobenzene 4%
4-(4-Heptylcyclohexyl)-1-chlorobenzene 4%
4'-(4-Ethylcyclohexyl)-3,4-difluorobiphenyl 5%
4'-(4-Propylcyclohexyl)-3,4-difluorobiphenyl 5%
4'-(4-Pentylcyclohexyl)-3,4-difluorobiphenyl 10%
4-(4-(4-Ethylcyclohexyl)cyclohexyl)-1-chlorobenzene 5%
4-(4-(4-Butylcyclohexyl)cyclohexyl)-1-chlorobenzene 7%
4-(4-(4-Pentylcyclohexyl)cyclohexyl)-1-chlorobenzene 6%
4-(2-(2-Fluoro-4-(4-propylcyclohexyl)phenyl)ethynyl)-1-ethylbenzene 4%
4'-(4-Propylcyclohexyl)-3,4,5-trifluorobiphenyl 10%
4'-(4-Pentylcyclohexyl)-3,4,5-trifluorobiphenyl 10%
4-(4-(2-(4-Propylcyclohexyl)ethyl)cyclohexyl)-1-chloro-2-fluorobenzene 3%
4-(4-(2-(4-Pentylcyclohexyl)ethyl)cyclohexyl)-1-chloro-2-fluorobenzene 3%

COMPOSITION EXAMPLE 5
(Compound No. 1) 4-(4-(3-Ethyl-3-butenyl)cyclohexyl)-1-propylcyclohexane 4%
(Compound No. 2) 4-(4-(2-Propyl-2-propenyl)cyclohexyl)-1-propylcyclohexane 4%
(Compound No. 4) 4-(4-(1-Butyl-1-ethenyl)cyclohexyl)-1-propylcyclohexane 4%
(Compound No. 31) 4-(4-(4-(3-Ethyl-3-butenyl)cyclohexyl)cyclohexyl)benzonitrile 12%
4-(4-Propylcyclohexyl)benzonitrile 10%
4-(4-Pentylcyclohexyl)benzonitrile 8%
4'-Ethyl-4-cyanobiphenyl 7%
4-(2-(4-Ethyphenyl)ethynyl)-1-methoxybenzene 3%
4-(2-(4-Ethylphenyl)ethynyl)-1-methylbenzene 4%
4-(2-(4-Methyphenyl)ethynyl)-1-hexylbenzene 8%
4-(2-(4-Butylphenyl)ethynyl)-1-butylbenzene 4%
4-(4-Propylcyclohexyl)-1-butylcyclohexane 6%
4-(4-(4-Ethylcyclohexyl)cyclohexyl)benzonitrile 4%
4-(4-(4-Propylcyclohexyl)cyclohexyl)benzonitrile 4%
4-(4-(4-Butylcyclohexyl)cyclohexyl)benzonitrile 4%
4-(2-(2-Fluoro-4-(4-propylcyclohexyl)phenyl)ethynyl)-1-ethylbenzene 7%
4-(2-(2-Fluoro-4-(4-propylcyclohexyl)phenyl)ethynyl)-1-propylbenzene 7%

COMPOSITION EXAMPLE 6
(Compound No. 1) 4-(4-(3-Ethyl-3-butenyl)cyclohexyl)-1-propylcyclohexane 7%
(Compound No. 2) 4-(4-(2-Propyl-2-propenyl)cyclohexyl)-1-propylcyclohexane 7%
(Compound No. 4) 4-(4-(1-Butyl-1-ethenyl)cyclohexyl)-1-propylcyclohexane 6%
2-Fluoro-4-(4-ethylcyclohexyl)benzonitrile 4%
2-Fluoro-4-(4-propylcyclohexyl)benzonitrile 5%
2-Fluoro-4-(4-pentylcyclohexyl)benzonitrile 8%
4-(4-Propylcyclohexyl)benzonitrile 4%
4-(2-(4-Ethylphenyl)ethynyl)-1-methoxybenzene 5%
4-(4-Methoxymethylcyclohexyl)-1-propylcyclohexane 3%
4-(4-Propylcyclohexyl)-1-butylcyclohexane 3%
4-(4-(4-Ethylcyclohexyl)cyclohexyl)benzonitrile 6%
4-(4-(4-Propylcyclohexyl)cyclohexyl)benzonitrile 6%
4-(4-(4-Butylcyclohexyl)cyclohexyl)benzonitrile 6%
4-(4-(4-Pentylcyclohexyl)cyclohexyl)benzonitrile 6%
2-Fluoro-4-(4-(4-propylcyclohexyl)cyclohexyl)benzonitrile 6%
4-(2-(2-Fluoro-4-(4-propylcyclohexyl)phenyl)ethynyl)-1-ethylbenzene 4%
4-(2-(2-Fluoro-4-(4-propylcyclohexyl)phenyl)ethynyl)-1-propylbenzene 3%
3-Fluoro-4-cyanophenyl=4-ethoxymethylbenzoate 4%
3-Fluoro-4-cyanophenyl=4-propoxymethylbenzoate 5%
4'-Cyanobiphenylyl=4-(4-propylcyclohexyl)benzoate 2%

COMPOSITION EXAMPLE 7
(Compound No. 1) 4-(4-(3-Ethyl-3-butenyl)cyclohexyl)-1-propylcyclohexane 8%
(Compound No. 31) 4-(4-(4-(3-Ethyl-3-butenyl)cyclohexyl)cyclohexyl)benzonitrile 5%
(Compound No. 46) 4'-(4-(1-Butyl-1-ethenyl)cyclohexyl)-4-trifluoromethoxybiphenyl 5%
2-(3,4-Difluorophenyl)-5-propylpyrimidine 10%
4-(4-Propylcyclohexyl)benzonitrile 10%
4-(4-(3-Butenyl)cyclohexyl)benzonitrile 10%
4-(4-(3-Pentenyl)cyclohexyl)benzonitrile 10%
2-(4'-Fluorobiphenylyl)-5-propylpyrimidine 6%
2-(4'-Fluorobiphenylyl)-5-butylpyrimidine 6%
2-(4'-Fluorobiphenylyl)-5-pentylpyrimidine 6%
4-(2-(4-(2-(4-Propylcyclohexyl)ethyl)phenyl)ethynyl)-1-ethylbenzene 3%
4-(2-(4-(2-(4-Propylcyclohexyl)ethyl)phenyl)ethynyl)-1-propylbenzene 3%
4-(2-(4-(2-(4-Propylcyclohexyl)ethyl)phenyl)ethynyl)-1-butylbenzene 3%
2-(4-(4-Ethylcyclohexyl)phenyl)-5-ethylpyrimidine 3%
2-(4-(4-Ethylcyclohexyl)phenyl)-5-propylpyrimidine 3%
2-(4-(4-Propylcyclohexyl)phenyl)-5-ethylpyrimidine 3%
2-(4-(4-Propylcyclohexyl)phenyl)-5-propylpyrimidine 3%
2-(4-(4-Butylcyclohexyl)phenyl)-5-propylpyrimidine 3%
2-(4'-Ethylbiphenylyl)-5-hexylpyrimidine 3%

COMPOSITION EXAMPLE 8
(Compound No. 31) 4-(4-(4-(3-Ethyl-3-butenyl)cyclohexyl)cyclohexyl)benzonitrile 10%
(Compound No. 39) 2-Fluoro-4-(4-(4-(3-ethyl-3-butenyl)cyclohexyl)cyclohexyl)-1-trifluoromethoxybenzene 10%
4'-Ethyl-4-cyanobiphenyl 10%

4'-Butyl-4-cyanobiphenyl 7%
4'-Pentyl-4-cyanobiphenyl 7%
4-(4-Ethylcyclohexyl)benzoate 6%
2-(4-Fluorophenyl)-5-pentylpyrimidine 6%
2-(4-Ethylphenyl)-5-ethylpyrimidine 3%
2-(4-Ethylphenyl)-5-propylpyrimidine 3%
2-(4-Ethylphenyl)-5-butylpyrimidine 3%
4-(4-(4-Ethylcyclohexyl)cyclohexyl)-1-methylbenzene 4%
4-(4-(4-Propylcyclohexyl)cyclohexyl)-1-methylbenzene 4%
4-(4-(4-Propylcyclohexyl)cyclohexyl)-1-methoxybenzene 3%
4-(4-(4-Propylcyclohexyl)cyclohexyl)-1-propylbenzene 8%
4-(4-(4-Propylcyclohexyl)cyclohexyl)benzonitrile 5%
4-Fluorophenyl=4-(4-propylcyclohexyl)benzoate 5%
4-Fluorophenyl=4-(4-propylcyclohexylcarbonyloxy)benzoate 4%
4-(4-(2-Propoxyethyl)cyclohexyl)benzonitrile 5%

The compounds, of the present invention, represented by the formula (1) can be easily prepared by making the most of conventional chemical techniques for organic synthesis. For example, they can be easily prepared by using a suitable combination of techniques described, for example, in "Organic Synthesis, Organic Reactions: JIKKEN KAGKKU KOZA" etc.

The compounds represented by the following formula (1) can be produced, without any problem, according to representative examples of the production process described below.

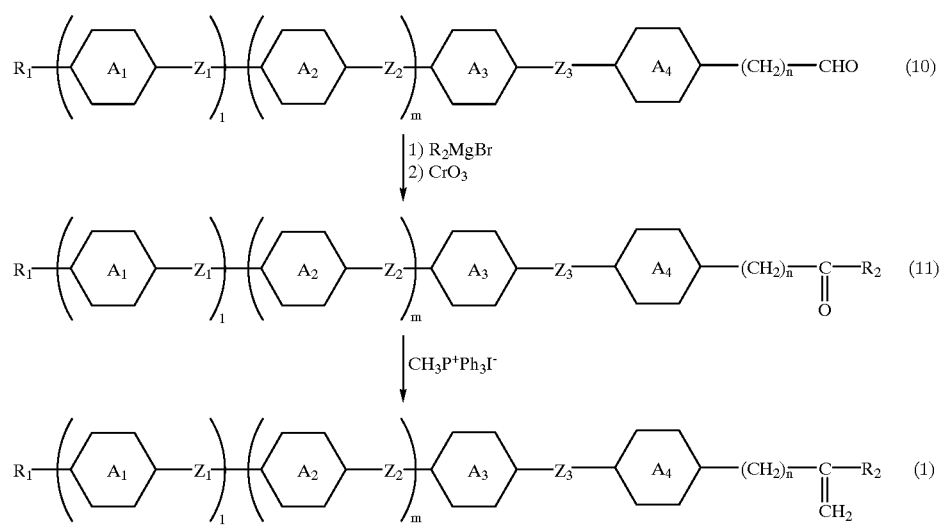

2-(4-Methoxyphenyl)-5-ethylpyrimidine 3%
4-Cyanophenyl=4-ethylbenzoate 3%

COMPOSITION EXAMPLE 9

(Compound No. 2) 4-(4-(2-Propyl-2-propenyl)cyclohexyl)-1-propylcyclohexane 10%
(Compound No. 4) 4-(4-(1-Butyl-1-ethenyl)cyclohexyl)-1-propylcyclohexane 10%
(Compound No. 31) 4-(4-(4-(3-ethyl-3-butenyl)cyclohexyl)cyclohexyl)benzonitrile 5%
(Compound No. 39) 2-fluoro-4-(4-(4-(3-ethyl-3-butenyl)cyclohexyl)cyclohexyl)-1-trifluoromethoxybenzene 5%
3,5-Difluoro-4-cyanophenyl=4-(3-pentenyl)benzoate 3%
2-(4-Cyanophenyl)-5-propyl-1,3-dioxane 10%
2-(4-Cyanophenyl)-5-butyl-1,3-dioxane 5%
4-Hexyloxyphenyl=4-ethylcyclohexanecarboxylate 2%
4-Pentoxyphenyl=4-propylcyclohexanecarboxylate 2%
4-Butoxyphenyl=4-butylcyclohexanecarboxylate 2%
4-Propylphenyl=4-butylcyclohexanecarboxylate 2%
4-Methylphenyl=4-pentylcyclohexanecarboxylate 2%
4-(2-(4-Ethylphenyl)ethynyl)-1-methylbenzene 3%
4-(4-(4-Propylcyclohexyl)cyclohexyl)-1-methylbenzene 5%
4-(4-(4-Propylcyclohexyl)cyclohexyl)-1-propylbenzene 8%
2-(3,4-Difluorophenyl)-5-propylpyrimidine 10%
4'-(4-Propylcyclohexyl)-4-fluorobiphenyl 4%
4-Fluorophenyl=4-(4-propylcyclohexyl)cyclohexanecarboxylate 3%

The exo-methylene site on the side chain may be constructed, for example, by the following method.

An alkyl Grignard reagent is allowed to act on an aldehyde derivative (10) followed by oxidation to give a ketone form (11). The oxidation may be suitably carried out by oxidation using chromic acid, as well as by DMSO oxidation, such as swan oxidation, oxidation using permanganic acid, and oxidation using oxygen in the presence of a catalyst.

A phosphonium salt of methyl iodide may be allowed to act on the ketone form (11) under basic conditions to construct an exo-methylene site. The base is preferably potassium t-butoxide. However, it is also possible to use an alkyllithium, such as sodium hydride, sodium hydroxide, potassium hydroxide, or butyllithium.

In the following description, DMF, DCC, DMAP, TMSI, and DIBAL have the following meanings.

DMF: Dimethylformamide
DCC: Dicyclohexylcarbodiimide
DMAP: 4-Dimethylaminopyridine
TMSI: Trimethylsilane iodide
DIBAL: Diisobutyl aluminum hydride Examples of the production of compounds of direct ring system will be given below. Among the compounds represented by the formula (1), for example, the compounds of direct ring system may be produced via the following synthesis route.

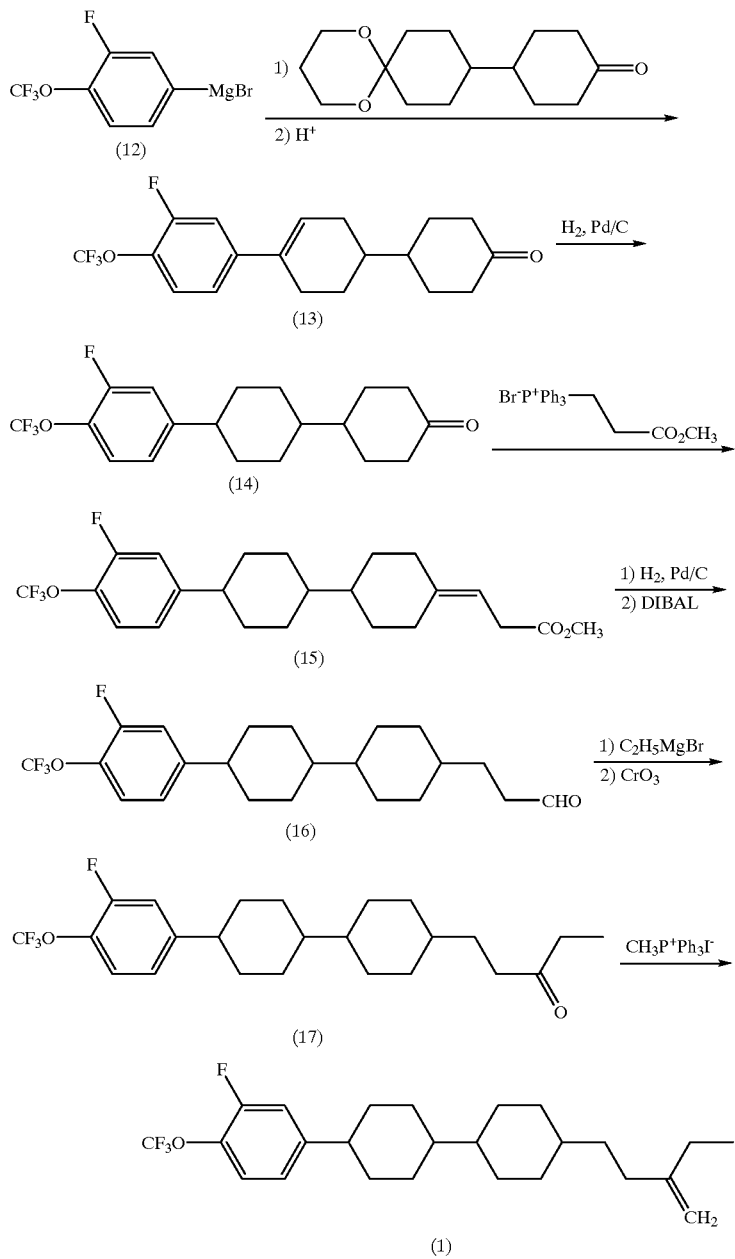

Specifically, a Grignard reagent (12), of 3-fluoro-4-trifluoromethoxybromobenzene, which can be produced by a process known from literature is allowed to act on 4,4'-bicyclohexanedione=monoketal and then treated with an acid to give a cyclohexene derivative (13). Acids usable here include mineral acids, such as sulfuric acid and hydrochloric acid, and sulfonic acids, such as p-toluenesulfonic acid, and acidic ion-exchange resins.

The olefin site of the cyclohexene derivative (13) is reduced in the presence of a catalyst to give a cyclohexanone derivative (14). The catalyst may be suitably selected from general-purpose catalysts, such as paradium-carbon and platinum-carbon.

A phosphonium salt prepared from a 2-bromopropanoic ester is allowed to act on the cyclohexanone derivative (14) under the same basic conditions as described above, and the double bond site of the resultant ester derivative (15) is reduced. Further, the ester site is reduced with DIBAL to give an aldehyde derivative (16). The reduction of the ester site is conveniently carried out using DIBAL. Alternatively, it is also possible to use a method wherein a reducing agent, such as aluminum lithium hydride or sodium boron hydride, is used to once reduce the ester site into an alcohol derivative which is then oxidized under conditions as described above to give an aldehyde form (16).

A Grignard reagent, chromic acid, and a phosphonium salt are successively allowed to act on the aldehyde derivative (16) to give the product (1) of the present invention.

An example of the production of a compound, having a 1,2-ethenylene site at the bonding site, among the compounds represented by the formula (1) will be described.

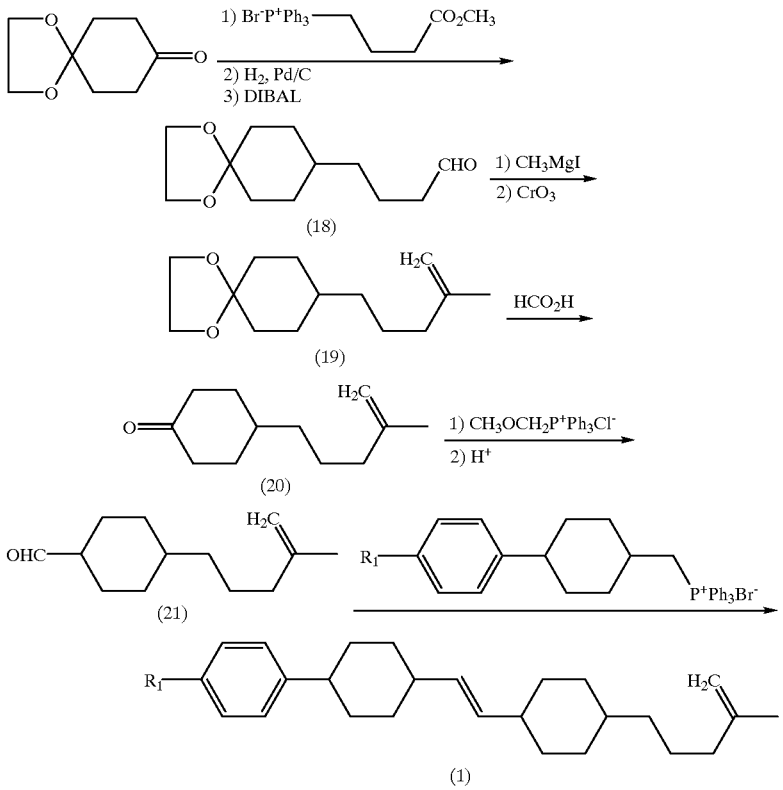

Cyclohexane-1,4-dione=monoketal is subjected to the action of a phosphonium salt of a 3-bromobutanoic acid ester, hydrogenation, and DIBAL reduction under the same conditions as described above to give an aldehyde derivative (18).

The aldehyde derivative (18) is subjected to the action of a Grignard reagent and oxidation under the same conditions as described above, and the ketal site of the resultant compound (19) is removed to give a cyclohexanone derivative (20). The ketal site is removed under acidic conditions, and formic acid, acetic acid, sulfuric acid, hydrochloric acid, and acidic ion-exchange resin are suitable for this purpose.

An enol ether prepared by the action of a phosphonium salt prepared from a methoxymethyl chloride under the same basic conditions as described above is treated under acidic conditions to give cyclohexanecarboaldehyde (21). The conversion of the enol ether form to the aldehyde form can be easily performed under acidic conditions. In this case, the use of formic acid, acetic acid, sulfuric acid, hydrochloric acid, or acidic ion-exchange resin is preferred.

A phosphonium salt prepared from a cyclohexylmethyl-bromide derivative is allowed to act on the cyclohexanecarboaldehyde (21) under the same basic conditions as described above to give the compound (1) of the present invention. When the 1,2-ethenylene site of the resultant compound (1) is in a cis form, the cis form is isomerized into a trans form. The isomerization may be conducted using an acid compound, such as sulfinic acid. Alternatively, it may be conducted by treating the cis form with an oxidizing agent to convert the cis form to an epoxide which is then subjected to bromination and reduction.

Among the compounds, of the present invention, represented by the formula (1), a compound having a triple bond at the bonding site in its molecule may be prepared, for example, by the following process.

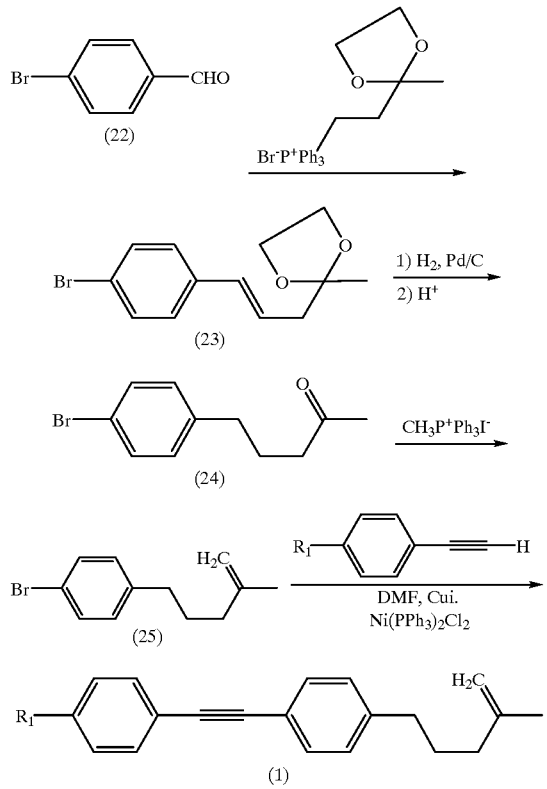

A phosphonium salt prepared from 2-methyl-2-(2-bromoethyl)-1,3-dioxolane is allowed to act on 4-bromobenzaldehyde (22) to give an olefin form (23) which is then hydrogenated and treated with an acid to give a ketone derivative (24).

A phosphonium salt of methyl iodide is allowed to act on the ketone derivative (24) under the same basic conditions as described above to give an exo-methylene derivative (25). A phenylacetylene derivative is allowed to act on the exo-methylene derivative (25) to give the compound (1) of the present invention.

Among the compounds, of the present invention, represented by the formula (1), a compound having an ester bond at the bonding site in its molecule can be prepared, for example, by the following process.

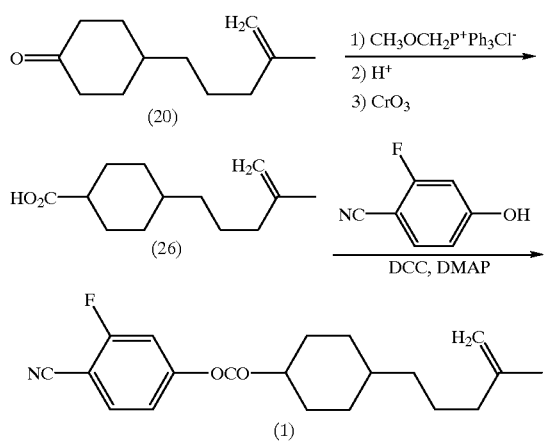

A phosphonium salt of methoxymethyl chloride is allowed to act on the cyclohexanone derivative (20) prepared under the same conditions as described above, and the resultant product is then treated under acidic conditions to give an alcohol form which is then oxidized to give a carboxylic acid derivative (26).

3-Fluoro-4-cyanophenol is allowed to act on the carboxylic acid derivative (26) to conduct dehydrocondensation, thereby giving the compound (1) as an ester of the present invention. The dehydrocondensation may be conveniently performed using a condensing agent, such as DCC. Alternatively, it is also possible to use a method wherein the carboxylic acid compound (26) is once converted to an acid chloride on which phenol is then allowed to act under basic conditions.

Among the compounds, of the present invention, represented by the formula (1), a compound having a methyleneoxy group at the bonding site can be conveniently produced, for example, by the following synthesis route.

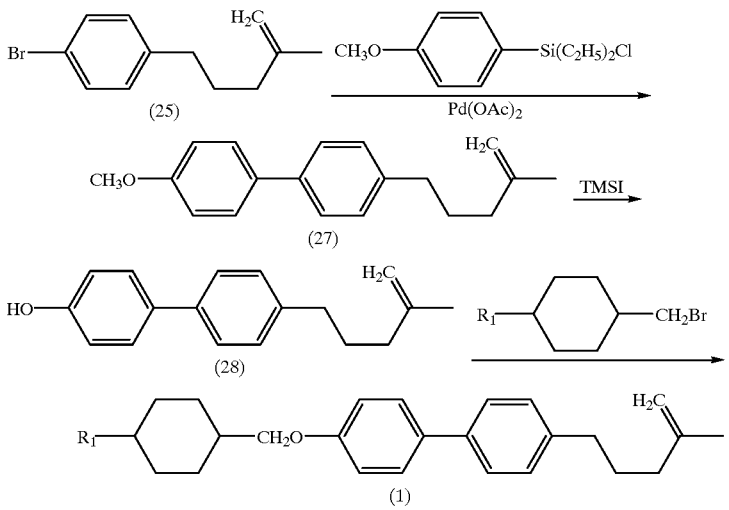

Specifically, a silane reagent is allowed to act on the bromide form (25), as described above, in the presence of a catalyst to effect a cross coupling reaction, thereby giving a methoxy form (27). The methoxy form (27) is demethylated to give a phenol (28) on which a cyclohexanemethyl bromide derivative is then allowed to act to give the compound (1) of the present invention.

The demethylation may be carried out by various methods. For example, it may be conveniently carried out using, for example, hydrobromic acid or trimethylsilyl iodide. The etherification at the final stage may be carried out under basic conditions. In this case, sodium hydroxide, potassium hydroxide, sodium hydride or the like are suitable as the base.

Among the compounds, of the present invention, represented by the formula (1), a compound having a 1,4-butylene site at the bonding site can be conveniently produced, for example, by the following synthesis route.

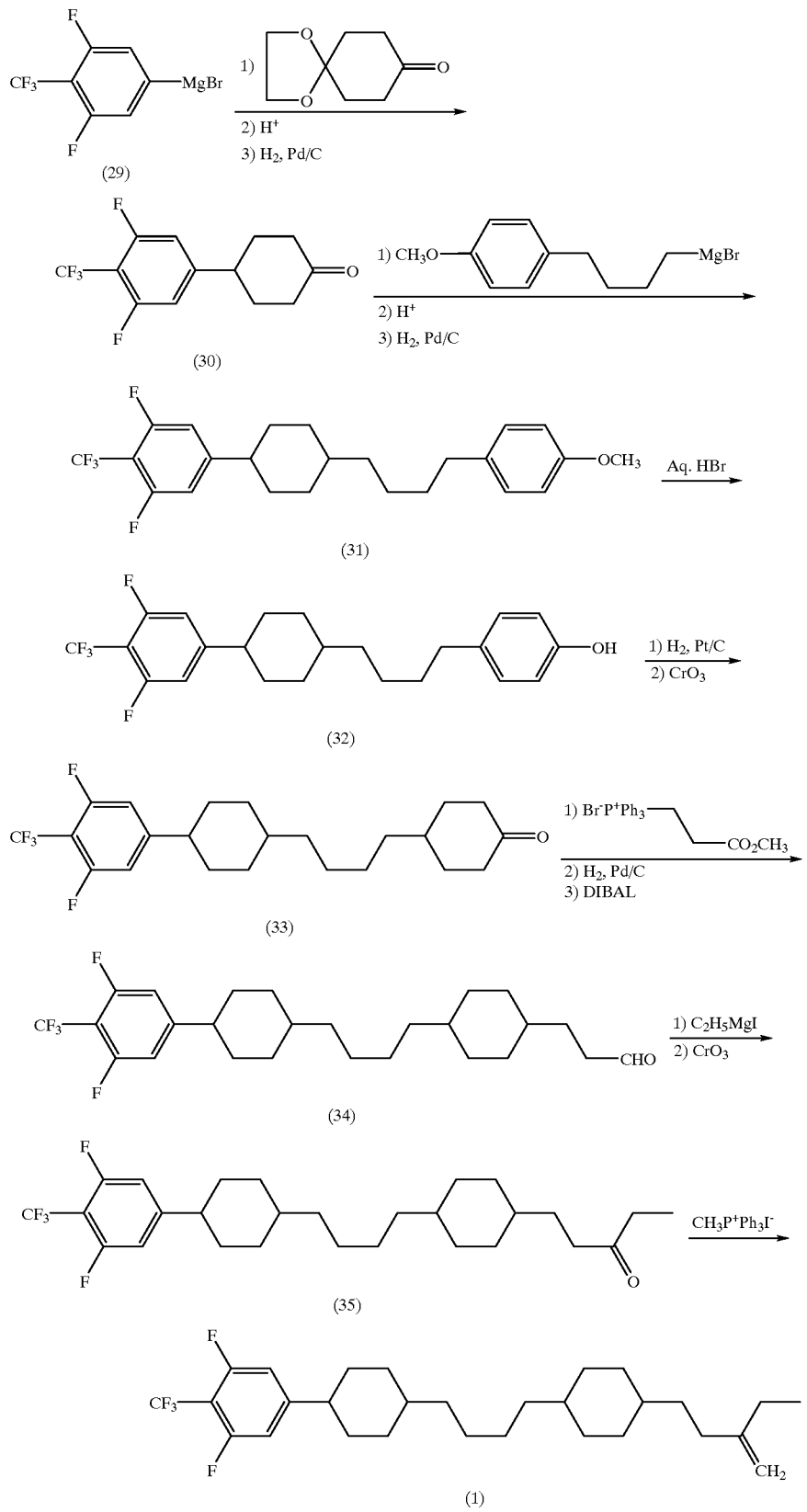

Specifically, cyclohexane-1,4-dione=monoketal is allowed to act on a Grignard reagent (29) of 3,5-difluoro-4-trifluoromethylbromobenzene prepared by a process known from literature, and the resultant product is subjected to dehydration under acidic conditions, removal of ketal, and hydrogenation to give a cyclohexanone derivative (30).

A Grignard reagent of 4-methoxy-(4-bromobutyl)benzene is allowed to act on the cyclohexanone derivative (30) to give an alcohol form which is then dehydrated under acidic conditions and hydrogenated to give an anisole derivative (31). The anisole derivative (31) is demethylated under the same conditions as described above to give a phenol derivative (32). The phenol site is hydrogenated to give cyclohexanol which is then oxidized under the same conditions as described above to give a cyclohexanone derivative (33). The cyclohexanone derivative (33) is subjected to the action of a phosphonium salt of a 2-bromopropanoic ester, hydrogenation, and DIBAL reduction under the same conditions as described above to give an aldehyde derivative (34).

A Grignard reagent is allowed to act on the aldehyde derivative (34) according to the method as described above, and the resultant product is further oxidized to give a ketone derivative (35). A phosphonium salt of methyl iodide is allowed to act on the ketone derivative (35) according to the method as described above to give the compound (1) of the present invention.

Among the compounds, of the present invention, represented by the formula (1), a compound containing 1,2-ethylene at the bonding site can be produced, for example, by the following process as an example.

Butyllithium and zinc chloride are successively allowed to act on a bromide (36) to give an organozinc compound (37). The bromide prepared above is allowed to act on the organozinc compound (37) in the presence of a catalyst to give the compound (1) of the present invention.

Among the compounds; of the present invention, represented by the formula (1), a compound containing a cyclohexene site can be produced, for example, by the following process as an example.

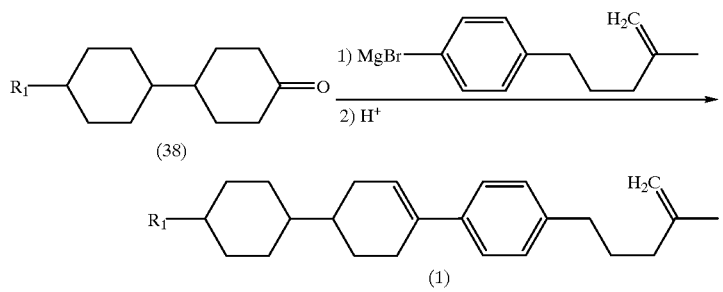

Specifically, a Grignard reagent of a bromide, the production process of which has been described above, may be allowed to act on a cyclohexanone derivative (38) and then dehydrated under the same conditions as described above to give the compound (1) of the present invention.

Among the compounds, of the present invention, represented by the formula (1), a compound containing a 1,3-dioxane skeleton in its molecule can be conveniently produced, for example, by the following process.

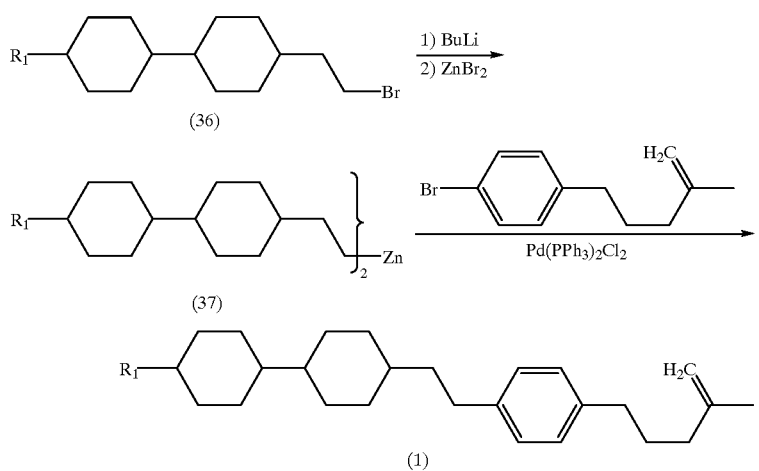

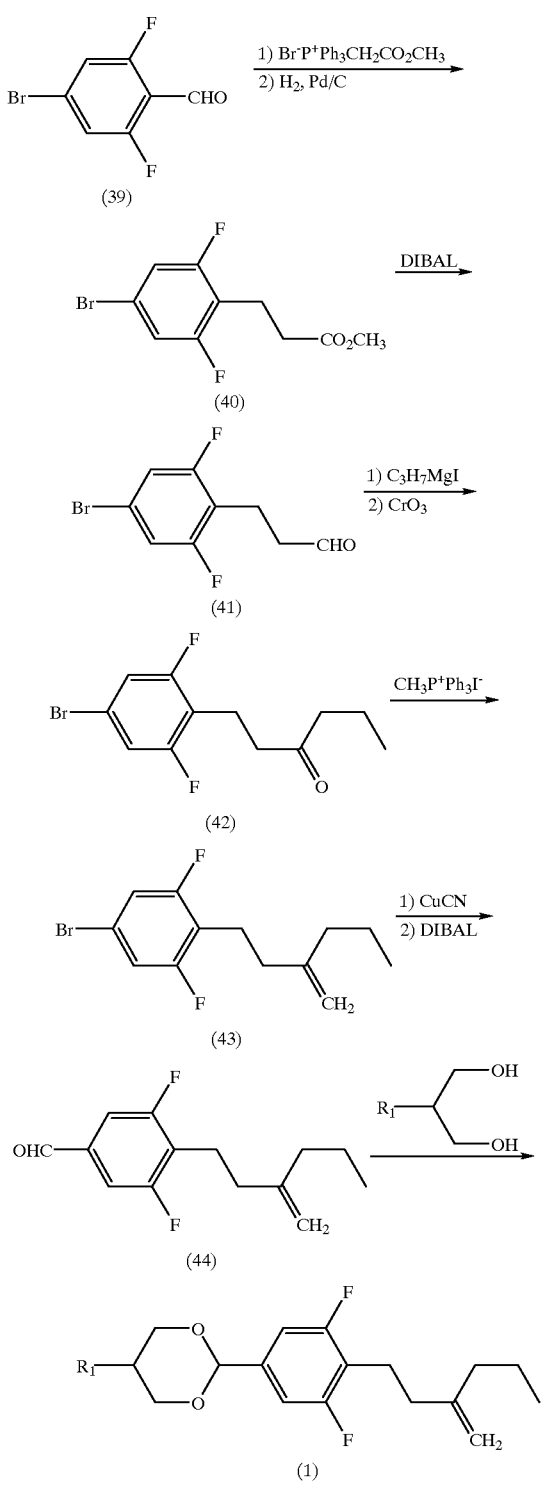

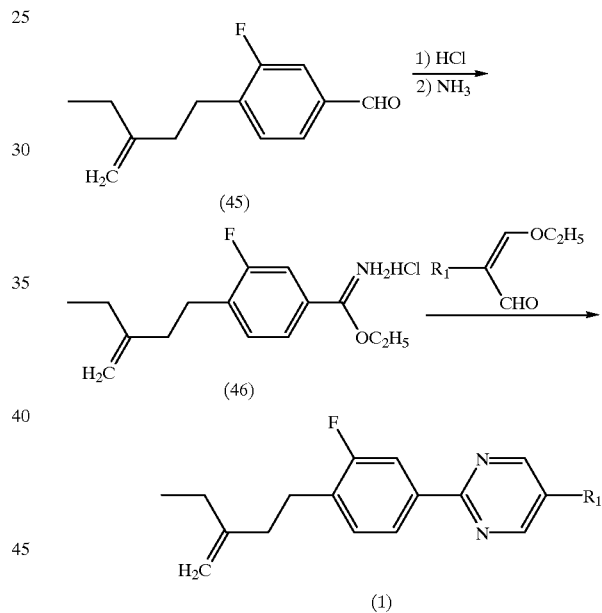

Specifically, a phosphonium salt of a bromoacetic ester is allowed to act on a benzaldehyde derivative (39) according to the method as described above, followed by hydrogenation under the same conditions as described above to give an ester derivative (40).

The ester site is converted to an aldehyde (41) by the method as described above, and a Grignard reagent and an oxidizing agent are successively allowed to act on the aldehyde (41) to give a ketone deribative (42). A phosphonium salt of methyl iodide is allowed to act on the ketone derivative (42) to give an exo-methylene derivative (43).

The exo-methylene derivative (43) is treated with copper cyanide to give a benzonitrile form which is then treated with DIBAL to give a benzaldehyde derivative (44). Various 2-substituted 1,3-propanediols are allowed to act on the aldehyde derivative (44) to give the compound (1) of the present invention.

Among the compounds, of the present invention, represented by the formula (1), a compound containing a pyrimidine ring in its molecule can be produced, for example, by the following process.

Specifically, hydrogen chloride and ammonia are allowed to act on a benzaldehyde derivative (45) by a conventional method to give an amidine (46). Various alkylacroleins are allowed to act on the amidine (46) under basic conditions to give the compound (1) of the present invention.

Among the compounds, of the present invention, represented by the formula (1), a compound containing a pyridine ring in its molecule can be produced, for example, by the following process.

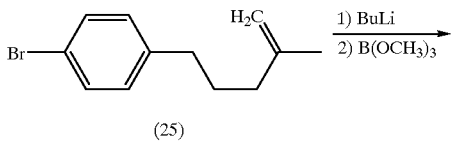

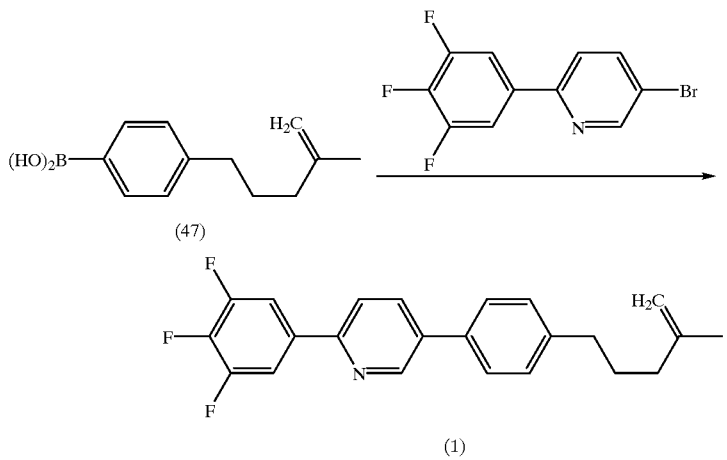

An alkyllithium and a boric ester are allowed to act on a bromide (25), the production process of which has been described above, to give a boric acid derivative (47). A pyridinium bromide derivative is allowed to act on the boric acid derivative (47) to give rise to a cross coupling reaction, thereby giving the compound (1) of the present invention.

EXAMPLES

Production processes and application exmaples regarding the compounds of the present invention will be described in more detail with reference to the following exmaples. In the following exmaples, C represents a crystal, N a nematic phase, S a smectic phase, and I an isotropic liquid, and all the phase transition temperatures are in.

Example 1
Preparation of 4'-propyl-4(3-ethyl-3-butenyl)bicyclohexane (a compound represented by the formula (1) wherein $R_1$ represents a propyl group, rings $A_3$ and $A_4$ represent a 1,4-cyclohexane ring, $Z_3$ represents a covalent bond, l and m are 0, n is 2, and $R_2$ represents an ethyl group; compound No. 4)

A mixture of methyltriphenylphosphonium iodide (50 mmol), potassium-t-butoxide (55 mmol), and tetrahydrofuran (hereinafter abbreviated to "THF") (50 ml) was stirred at room temperature for 2 hr to prepare a reddish yellow solution. A solution of 4'-propyl-4-(3-oxobutyl)bicyclohexane (45 mmol) in 50 ml of THF prepared according to a method described in Japanese Patent Application No. 129304/1994 was dropwise added thereto at 0 or below, and the mixture was stirred at room temperature for 3 hr. 200 ml of water was poured into the reaction mixture, and the mixture was extracted with 100 ml of heptane. The heptane phase was washed until it became neutral while removing precipitated insolubles by filtration. It was then dried over magnesium sulfate anhydride. The solvent was distilled off to give a crude product which was then purified by silica gel column chromatography (eluting solution: heptane) and then recrystallization (twice from a five-fold amount of ethanol in a freezer) to give 31.5 mmol (yield 69%) of the title compound. This compound was smectic at room temperature, and the S-I transition point was 97.5 to 98.5. The structure was well supported by various spectral data on this compound.

$^1$H-NMR: δ (ppm): 4.67 (brs/2H), 2.03–0.81 (m/36H)
GC-MS: 453 (M$^+$)

Example 2
Preparation of 4'-(4-(2-propyl-2-propenyl)cyclohexyl)-4-trifluoromethoxybiphenyl (a compound represented by the formula (1) wherein $R_1$ represents a trifluoromethoxy group, $A_2$ and $A_3$ represent a 1,4-phenylene ring, $A_4$ represents a 1,4-cyclohexylene ring, $Z_2$ and $Z_3$ represent a covalent bond, l is 0, m is 1, n is 1, and $R_2$ represents a propyl group; compound No. 46)

A Grignard reagent (as a solution thereof in 300 ml of THF) prepared from 4-trifluoromethoxybromobenzene (253 mmol) was dropwise added to a mixture of 4-(4-methoxymethylcyclohexyl)-1-iodobenzene (169 mmol), 200 ml of THF, and palladium chloride (5.1 mmol) under reflux over a period of 30 min. After that the starting material existed no longer was confirmed by gas chromatography, the system was allowed to stand for cooling. 6 M HCl and toluene were added thereto, and the mixture was stirred. The precipitated insolubles were filtered off, and the organic phase was washed with water and dried over magnesium sulfate anhydride. The solvent was distilled off under reduced pressure to give a crude product as a yellow solid. The crude product was purified by silica gel column chromatography (eluting solution: toluene)-to give 4'-(4-methoxymethylcyclohexyl)-4-trifluoromethoxybiphenyl (100 mmol) as a pale yellow solid (yield 59%).

A mixture of 4'-(4-methoxymethylcyclohexyl)-4-trifluoromethoxybiphenyl (100 mmol), TMSI (144 mmol), 15 ml of acetonitrile, and 10 ml of methylene chloride was stirred at room temperature for 4 hr. Ice and 6 M HCl were added to the reaction mixture, and the mixture was stirred. The organic phase was washed twice with a saturated aqueous solution of sodium thiosulfate. It was then dried over magnesium sulfate anhydride, and the solvent was distilled off under reduced pressure to give a crude product. The crude product was purified by silica gel column chromatography (eluting solution: toluene—(1:1) mixture of toluene and ethyl acetate) to give 4'-(4-hydroxymethylcyclohexyl)-4-trifluoromethoxybiphenyl (68 mmol, yield 68%).

4'-(4-Hydroxymethylcyclohexyl)-4-trifluoromethoxybiphenyl (68 mmol) was added at 0 or below in the absence of a solvent to a mixture of 78 mmol of pyridinium chlorochromate (PCC), 17 g of silica gel, and 350 ml of methylene chloride, and the mixture was stirred at room temperature for 6 hr to give a black suspension. Toluene was added thereto, and the mixture was stirred. The precipitated insolubles were filtered off through Celite, and the solvent was distilled off from the resultant black solution under reduced pressure to give a dark brown crude product. The crude product was purified by silica gel column chromatography (eluting solution: mixed solution of toluene and ethyl acetate (7:3)) to give 4-(4'-trifluoromethoxybiphenyl) cyclohexanecarboaldehyde (44 mmol, yield 81%).

A mixture of methoxymethyltriphenylphoshonium chloride (57 mmol), potassium-t-butoxide (62 mmol), and 100 ml of THF was stirred at room temperature for 40 min to prepare a red homogeneous solution. A solution of 4-(4'-trifluoromethoxybiphenylyl)cyclohexanecarboaldehyde (44 mmol) in 30 ml of THF was dropwise added at 0 or below, and the mixture was stirred at room temperature for 1 hr. The reaction mixture was extracted with toluene. The toluene phase was washed until it became neutral and dried over magnesium sulfate anhydride. The solvent was distilled off, and the resultant crude product was purified by silica gel column chromatography (eluting solution: mixed solvent of toluene and heptane (1:1)) to give an enol ether (quantitatively) as a colorless crystal.

50 ml of THF and 50 ml of 6 M HCl were added to the enol ether, and the mixture was stirred at room temperature overnight. Toluene was added to the suspension, and the mixture was stirred. The toluene phase was then washed with a saturated aqueous solution of sodium hydrogencarbonate and brine until it became neutral. It was then dried over magnesium sulfate anhydride. The solvent was distilled off under reduced pressure, and the residue was purified by silica gel column chromatography (eluting solution: toluene) to give 4'-(4-(2-oxoethyl)cyclohexyl)-4-trifluoromethoxybiphenyl as a white solid (29.8 mmol, yield 68%).

A solution of 4'-(4-(2-oxoethyl)cyclohexyl)-4-trifluoromethoxybiphenyl (29.8 mmol) in 20 ml of THF was dropwise added at 0 or below to a solution of propyl magnesium bromide (68 mmol) in 60 ml of THF, and the mixture was stirred at room temperature overnight. A saturated aqueous solution of ammonium chloride was added thereto, and the mixture was stirred and then extracted thrice with ethyl acetate, and the extract was dried over magnesium sulfate anhydride.

The solvent was distilled off under reduced pressure, and the resultant crude product was recrystallized from 13 ml of heptane to give 4'-(4-(2-hydroxypentyl)cyclohexyl)-4-trifluoromethoxybiphenyl as a white solid (12.3 mmol, yield 54%).

4'-(4-(2-Hydroxypentyl)cyclohexyl)-4-trifluoromethoxybiphenyl (12.3 mmol) was added at 0 or below in the absence of a solvent to a mixture of PCC (13.5 mmol), 3 g of silica gel, and 70 ml of methylene chloride, and the mixture was stirred at room temperature for 7 hr to give a black suspension. 500 ml of toluene was added thereto, and the mixture was stirred. The precipitated insolubles were filtered off through Celite, and the solvent was distilled off from the resultant black solution under reduced pressure to give a dark brown crude product. The crude product was purified by silica gel column chromatography (eluting solution: toluene) to give 4'-(4-(2-oxopentyl) cyclohexyl)-4-trifluoromethoxybiphenyl (7.4 mmol, yield 66%) as a white crystal.

A mixture of methyltriphenylphosphonium iodide (9.7 mmol), potassium-t-butoxide (10.6 mmol), and 20 ml of THF was stirred at room temperature for 2 hr to prepare a red solution. A solution of 4'-4-(2-oxopentyl)cyclohexyl)-4-trifluoromethoxybiphenyl (7.4 mmol) in 15 ml of THF was dropwise added thereto at 0 or below, and the mixture was stirred at room temperature for 1 hr. 200 ml of water was poured into the reaction mixture, and the mixture was extracted with 100 ml of toluene. The toluene phase was washed until it became neutral while removing precipitated insolubles by filtration. It was then dried over magnesium sulfate anhydride. The solvent was distilled off to give a crude product which was then purified by silica gel column chromatography (eluting solution: heptane) and then recrystallization (twice from a three-fold amount of ethanol) to give the title compound (3.4 mmol, yield 46%). The S-1 transition point was 72.7 to 72.8. The structure was well supported by various spectral data on this compound.

$^{1}$H-NMR: δ (ppm): 7.73–7.22 (m, 8H), 4.73 (brs, 2H), 2.52 (t, 1H), 2.00–0.84 (m, 18H) GC-MS: 402 (M$^{+}$)

Example 3

The procedures of Examples 1 and 2 were repeated to prepare the following compounds. The compounds prepared in Examples 1 and 2 are also listed below.

Compound No. 1
4'-Propyl-4-(1-butyl-1-ethenyl)bicyclohexane S-I point 48.5–49.8° C.

Compound No. 2
4'-Propyl-4-(2-propyl-2-propenyl)bicyclohexane S-I point 41.4–41.7° C.

Compound No. 3
4'-Propyl-4-(3-methyl-3-butenyl)bicyclohexane

Compound No. 4
4'-Propyl-4-(3-ethyl-3-butenyl)bicyclohexane S-I point 97.5–98.5° C.

Compound No. 5
4'-Pentyl-4-(1-butyl-1-ethenyl)bicyclohexane

Compound No. 6
4'-Pentyl-4-(2-propyl-2-propenyl)bicyclohexane

Compound No. 7
4'-Pentyl-4-(3-methyl-3-butenyl)bicyclohexane

Compound No. 8
4'-Pentyl-4-(3-ethyl-3-butenyl)bicyclohexane S-I point 103.5–104.2° C.

Compound No. 9
4-(2-(4-Propylcyclohexyl)ethyl)-1-(3-ethyl-3-butenyl) cyclohexane Compound No. 10
4-(2-(4-Propylcyclohexyl)ethenyl)-1-(3-ethyl-3-butenyl) cyclohexane Compound No. 11
4-(2-(4-Pentylphenyl)ethynyl)-1-(3-ethyl-3-butenyl) benzene Compound No. 12
4-(4-(4-Propylcyclohexyl)butyl)-1-(3-ethyl-3-butenyl) cyclohexane Compound No. 13
4-(2-(3,4-Difluorophenyl)ethyl)-1-(3-ethyl-3-butenyl) cyclohexane Compound No. 14
4-(2-(4-Ethylphenyl)ethyl)-1-(3-ethyl-3-butenyl) cyclohexane Compound No. 15
4-(4-Propylbenzyloxy)-1-(3-methyl-3-butenyl)benzene Compound No. 16
4-(3-Ethyl-3-butenyl)-1-(4-propylcyclohexyl) cyclohexene Compound No. 17
4-(4-(3-Ethyl-3-butenyl)cyclohexyl)-1-propylcyclohexene Compound No. 18
4-(3-Ethyl-3-butenyl)-1-(2-(4-propylcyclohexyl)ethyl) cyclohexene Compound No. 19
2-(4-(3-Methyl-3-butenyl)phenyl)-5-pentyl-1,3-dioxane Compound No. 20
2-(4-(3-Ethyl-3-butenyl)phenyl)-5-pentylpyrimidine
Compound No. 21
2-(4-(3-Ethyl-3-butenyl)phenyl)-5-cyanopyrimidine
Compound No. 22
2-(4-(3-Ethyl-3-butenyl)phenyl)-5-pentylpyridine
Compound No. 23
2-(2-(4-(3-Ethyl-3-butenyl)phenyl)ethynyl)-5-propoxypyridine
Compound No. 24
1"-(3-Ethyl-3-butenyl)-4-propyltercyclohexane S-I point 250° C. or above
Compound No. 25
1"-(3-Ethyl-3-butenyl)-4-(3-butenyl)tercyclohexane S-I point 250° C. or above
Compound No. 26
4'-(4-Propylphenyl)-4-(3-methyl-3-butenyl)bicyclohexane
Compound No. 27
4'-(4-Propylphenyl)-4-(1-butyl-1-ethenyl)bicyclohexane
Compound No. 28
4'-(4-Propylphenyl)-4-(2-propyl-2-propenyl)bicyclohexane
Compound No. 29
4'-(4-Propylphenyl)-4-(3-ethyl-3-butenyl)bicyclohexane
Compound No. 30
4'-(4-Pentylphenyl)-4-(3-ethyl-3-butenyl)bicyclohexane
Compound No. 31
4'-(4-Cyanophenyl)-4-(3-ethyl-3-butenyl)bicyclohexane C-N point 61.0–61.8° C. N-I point 212.2–214.3° C.
Compound No. 32
4'-(4-Chlorophenyl)-4-(3-ethyl-3-butenyl)bicyclohexane
Compound No. 33
4'-(3,4-Difluorophenyl)-4-(3-ethyl-3-butenyl)bicyclohexane
Compound No. 34
4'-(3,4,5-Trifluorophenyl)-4-(3-ethyl-3-butenyl)bicyclohexane
Compound No. 35
4'-(4-Trifluoromethylphenyl)-4-(3-ethyl-3-butenyl)bicyclohexane
Compound No. 36
4'-(4-Trifluoromethoxyphenyl)-4-(3-ethyl-3-butenyl)bicyclohexane C-N point 65.1–66.2° C. N-I point 143.2–147.4° C.
Compound No. 37
4'-(4-Difluoromethoxyphenyl)-4-(3-ethyl-3-butenyl)bicyclohexane
Compound No. 38
4'-(3-Fluoro-4-trifluoromethylphenyl)-4-(3-ethyl-3-butenyl)bicyclohexane
Compound No. 39
4'-(3-Fluoro-4-trifluoromethoxyphenyl)-4-(3-ethyl-3-butenyl)bicyclohexane
Compound No. 40
4'-(3,5-Difluoro-4-trifluoromethylphenyl)-4-(3-ethyl-3-butenyl)bicyclohexane
Compound No. 41
4'-(3,5-Difluoro-4-trifluoromethoxyphenyl)-4-(3-ethyl-3-butenyl)bicyclohexane
Compound No. 42
4-(4'-Propylbicyclohexy-4-yl)-1-(3-ethyl-3-butenyl)benzene
Compound No. 43
4-(4'-Propylbiphenylyl)-1-(3-methyl-3-butenyl)cyclohexane
Compound No. 44
4-(4'-Propylbiphenylyl)-1-(1-butyl-1-ethenyl)cyclohexane
Compound No. 45
4-(4'-Propylbiphenylyl)-1-(2-propyl-2-propenyl)cyclohexane
Compound No. 46
4-(4'-Trifluoromethoxybiphenylyl)-1-(2-propyl-2-propenyl)cyclohexane S-I point 72.7–72.8° C.
Compound No. 47
4-(4'-Propylbiphenylyl)-1-(3-ethyl-3-butenyl)cyclohexane
Compound No. 48
4-(4'-Cyanobiphenylyl)-1-(3-ethyl-3-butenyl)cyclohexane
Compound No. 49
4-(4'-Trifluoromethylbiphenylyl)-1-(3-ethyl-3-butenyl)cyclohexane
Compound No. 50
4-(4'-Trifluoromethoxybiphenylyl)-1-(3-ethyl-3-butenyl)cyclohexane S-I point 126.7–127.6° C.
Compound No. 51
4-(3'-Fluoro-4'-trifluoromethylbiphenylyl)-1-(3-ethyl-3-butenyl)cyclohexane
Compound No. 52
4-(3'-Fluoro-4'-trifluoromethoxybiphenylyl)-1-(3-ethyl-3-butenyl)cyclohexane
Compound No. 53
4-(3',5'-Difluoro-4'-trifluoromethylbiphenylyl)-1-(3-ethyl-3-butenyl)cyclohexane
Compound No. 54
4-(3',5'-Difluoro-4'-trifluoromethoxybiphenylyl)-1-(3-ethyl-3-butenyl)cyclohexane
Compound No. 55
4-(3',4'-Difluorobiphenylyl)-1-(3-ethyl-3-butenyl)cyclohexane C-N point 53.8–56.1° C. N-I point 103.1–104.5° C.
Compound No. 56
4-(3',4',5'-Trifluorobiphenylyl)-1-(3-ethyl-3-butenyl)cyclohexane C-N point 23.1–24.9° C. N-I point 51.3–54.7° C.
Compound No. 57
2-(4-(4-Propylcyclohexyl)phenyl)-5-(3-ethyl-3-butenyl)pyrimidine
Compound No. 58
2-(4-(4-Propylcyclohexyl)phenyl)-5-(3-ethyl-3-butenyl)pyridine
Compound No. 59
2-(4-(3-Ethyl-3-butenyl)phenyl)-5-(4-pentylcyclohexyl)pyrimidine
Compound No. 60
5-(4-(3-Ethyl-3-butenyl)phenyl)-2-(4-pentylcyclohexyl)pyrimidine
Compound No. 61
5-(4-(3-Ethyl-3-butenyl)phenyl)-2-(4-pentylphenyl)pyridine
Compound No. 62
2-(4-(4-(3-Methyl-3-butenyl)cyclohexyl)cyclohexyl)-5-propyl-1,3-dioxane
Compound No. 63
4-(4-(3-Ethyl-3-butenyl)cyclohexyl)-1-(3,5-difluoro-4-trifluoromethoxyphenyl)cyclohexene
Compound No. 64
4-(4-Propylcyclohexyl)-1-(4-(3-ethyl-3-butenyl)phenyl)cyclohexene
Compound No. 65
4-(3-Ethyl-3-butenyl)-1-(3'-fluoro-4'-trifluoromethoxybiphenylyl)cyclohexene Compound No. 66
  4-Propyl-1-(4'-(3-Ethyl-3-butenyl)biphenylyl)cyclohexene
Compound No. 67
  4-(4-Cyanophenyl)-1-(4-(3-ethyl-3-butenyl)cyclohexyl)cyclohexene
Compound No. 68
  4-(3-ethyl-3-butenyl)-1-(4-(4-trifluoromethylphenyl)cyclohexyl)cyclohexene
Compound No. 69
  4-(4-(2-(4-Propylcyclohexyl)ethyl)cyclohexyl)-1-(3-ethyl-3-butenyl)benzene
Compound No. 70
  4-(2-(4-Propylcyclohexyl)ethyl)-1-(4-(3-ethyl-3-butenyl)phenyl)cyclohexene
Compound No. 71
  1-(2-(4-Propylcyclohexyl)ethyl)-4-(4-(3-ethyl-3-butenyl)phenyl)cyclohexene
Compound No. 72
  4'-(2-(4-Propylcyclohexyl)ethyl)-4-(3-methyl-3-butenyl)biphenyl
Compound No. 73
  4-(2-(4-(4-Pentylcyclohexyl)cyclohexyl)ethyl)-1-(3-ethyl-3-butenyl)benzene
Compound No. 74
  4-(4-Pentylcyclohexyl)-1-(2-(4-(3-ethyl-3-butenyl)phenyl)ethyl)cyclohexene
Compound No. 75
  4-(2-(4-(4-Cyanophenyl)cyclohexyl)ethyl)-1-(3-ethyl-3-butenyl)cyclohexane
Compound No. 76
  4-(2-(4-(3-Fluoro-4-cyanophenyl)cyclohexyl)ethyl)-1-(3-ethyl-3-butenyl)cyclohexane
Compound No. 77
  4-(2-(4-(4-Fluorophenyl)cyclohexyl)ethyl)-1-(3-ethyl-3-butenyl)cyclohexane
Compound No. 78
  4-(2-(4-(3,4-Difluorophenyl)cyclohexyl)ethyl)-1-(3-ethyl-3-butenyl)cyclohexane
Compound No. 79
  4-(2-(4-(3,4,5-Trifluorophenyl)cyclohexyl)ethyl)-1-(3-ethyl-3-butenyl)cyclohexane
Compound No. 80
  4-(2-(4-(4-Trifluoromethylphenyl)cyclohexyl)ethyl)-1-(3-ethyl-3-butenyl)cyclohexane
Compound No. 81
  4-(2-(4-(3-Fluoro-4-trifluoromethylphenyl)cyclohexyl)ethyl)-1-(3-ethyl-3-butenyl)cyclohexane
Compound No. 82
  4-(2-(4-(4-Trifluoromethoxyphenyl)cyclohexyl)ethyl)-1-(3-ethyl-3-butenyl)cyclohexane C-N point 63.1–64.8° C. N-I point 125.1–128.3° C.
Compound No. 83
  4-(2-(4-(3-Fluoro-4-trifluoromethoxyphenyl)cyclohexyl)ethyl)-1-(3-ethyl-3-butenyl)cyclohexane
Compound No. 84
  2-(4-(2-(4-(3-Ethyl-3-butenyl)cyclohexyl)ethyl)phenyl)-5-propylpyrimidine
Compound No. 85
  2-(4-(2-(4-(3-Ethyl-3-butenyl)cyclohexyl)ethyl)phenyl)-5-propylpyridine
Compound No. 86
  4-(2-(4-(3-Ethyl-3-butenyl)cyclohexyl)ethyl)-1-(4-trifluoromethoxyphenyl)cyclohexene
Compound No. 87
  4-(4-(2-(4-Propylcyclohexyl)ethenyl)cyclohexyl)-1-(3-ethyl-3-butenyl)benzene
Compound No. 88
  4-(2-(4-(3,4-Difluorophenyl)cyclohexyl)ethenyl)-1-(3-ethyl-3-butenyl)cyclohexane
Compound No. 89
  4-(2-(4-(3,4,5-Trifluorophenyl)cyclohexyl)ethenyl)-1-(3-ethyl-3-butenyl)cyclohexane
Compound No. 90
  4-(2-(4-(3-Fluoro-4-trifluoromethoxyphenyl)cyclohexyl)ethenyl)-1-(3-ethyl-3-butenyl)cyclohexane
Compound No. 91
  4-(4-(2-(4-Cyanophenyl)ethynyl)phenyl)-1-(3-methyl-3-butenyl)cyclohexane
Compound No. 92
  4-(2-(4-(4-Propylcyclohexyl)phenyl)ethynyl)-1-(3-ethyl-3-butenyl)benzene
Compound No. 93
  4-(4-(4-(4-Propylcyclohexyl)butyl)cyclohexyl)-1-(3-ethyl-3-butenyl)benzene
Compound No. 94
  4-(4-(4-(4-Propylphenyl)cyclohexyl)butyl)-1-(3-ethyl-3-butenyl)cyclohexane
Compound No. 95
  4-(4-(4-(4-Cyanophenyl)cyclohexyl)butyl)-1-(3-ethyl-3-butenyl)cyclohexane
Compound No. 96
  4-(4-(4-(3,4-Difluorophenyl)cyclohexyl)butyl)-1(3-ethyl-3-butenyl)cyclohexane
Compound No. 97
  4-(4-(4-(3,4,5-Trifluorophenyl)cyclohexyl)butyl)-1-(3-ethyl-3-butenyl)cyclohexane
Compound No. 98
  4-(4-(4-(3-Fluoro-4-trifluoromethoxyphenyl)cyclohexyl)butyl)-1-(3-ethyl-3-butenyl)cyclohexane
Compound No. 99
  4-(4-(4-(3-Fluoro-4-trifluoromethylphenyl)cyclohexyl)butyl)-1-(3-ethyl-3-butenyl)cyclohexane
Compound No. 100
  4-(4-(4-(3,5-Difluoro-4-trifluoromethoxyphenyl)cyclohexyl)butyl)-1-(3-ethyl-3-butenyl)cyclohexane
Compound No. 101
  4-(4-(3-Ethyl-3-butenyl)cyclohexyl)phenyl=4-pentylbenzoate
Compound No. 102
  4-Cyanophenyl=4'-(3-ethyl-3-butenyl)bicyclohexanecarboxylate
Compound No. 103
  4-Fluorophenyl=4'-(3-ethyl-3-butenyl)bicyclohexanecarboxylate
Compound No. 104
  3-Fluoro-4-cyanophenyl=4'-(3-ethyl-3-butenyl)bicyclohexanecarboxylate
Compound No. 105
  3,5-Difluoro-4-cyanophenyl=4'-(3-ethyl-3-butenyl)bicyclohexancarboxylate
Compound No. 106
  3,4,5-Trifluorophenyl=4'-(3-ethyl-3-butenyl)bicyclohexancarboxylate
Compound No. 107
  4-Trifluoromethoxyphenyl=4'-(3-ethyl-3-butenyl)bicyclohexanecarboxylate
Compound No. 108
  3-Fluoro-4-trifluoromethoxyphenyl=4'-(3-ethyl-3-butenyl)bicyclohexancarboxylate
Compound No. 109
  4-Cyanophenyl=4-(4-(3-ethyl-3-butenyl)cyclohexyl)benzoate Compound No. 110
4-Fluorophenyl=4-(4-(3-ethyl-3-butenyl)cyclohexyl)benzoate
Compound No. 111
3-Fluoro-4-cyanophenyl=4-(4-(3-ethyl-3-butenyl)cyclohexyl)benzoate
Compound No. 112
3,5-Difluoro-4-cyanophenyl=4-(4-(3-ethyl-3-butenyl)cyclohexyl)benzoate
Compound No. 113
3,4,5-Trifluorophenyl=4-(4-(3-ethyl-3-butenyl)cyclohexyl)benzoate
Compound No. 114
4-Trifluoromethoxyphenyl=4-(4-(3-ethyl-3-butenyl)cyclohexyl)benzoate
Compound No. 115
3-Fluoro-4-trifluoromethoxyphenyl=4-(4-(3-ethyl-3-butenyl)cyclohexyl)benzoate
Compound No. 116
4'-Cyanobiphenylyl=4-(3-ethyl-3-butenyl)cyclohexanecarboxylate
Compound No. 117
3',4'-Difluorobiphenylyl=4-(3-ethyl-3-butenyl)cyclohexanecarboxylate
Compound No. 118
4'-Cyanobiphenylyl=4-(3-ethyl-3-butenyl)benzoate
Compound No. 119
4-(4-(4-Propylbenzyloxy)phenyl)-1-(3-ethyl-3-butenyl)cyclohexane
Compound No. 120
4-(3-Ethyl-3-butenyl)cyclohexyl=4-(2-(4-propylcyclohexyl)ethyl)benzoate
Compound No. 121
4-(3-Ethyl-3-butenyl)cyclohexyl=2-fluoro-4-(2-(4-propylcyclohexyl)ethyl)benzoate
Compound No. 122
4-(3-Ethyl-3-butenyl)cyclohexyl=2,6-difluoro-4-(2-(4-propylcyclohexyl)ethyl)benzoate
Compound No. 123
4-(3-Ethyl-3-butenyl)cyclohexyl=4-(2-(4-propylcyclophenyl)ethyl)benzoate
Compound No. 124
4-(3-Ethyl-3-butenyl)cyclohexyl=2-fluoro-4-(2-(4-propylphenyl)ethyl)benzoate
Compound No. 125
4'-(4'-Trifluoromethoxybiphenylyl)-4-(3-ethyl-3-butenyl)bicyclohexane
Compound No. 126
4'-(3',4'-Difluorobiphenylyl)-4-(3-ethyl-3-butenyl)bicyclohexane
Compound No. 127
4'-(3',4',5'-Trifluorobiphenylyl)-4-(3-ethyl-3-butenyl)bicyclohexane S-I point 250° C. or above
Compound No. 128
4'-(4-Propylcyclohexyl)-4-(4-(3-ethyl-3-butenyl)cyclohexyl)biphenyl
Compound No. 129
4'-(4-Pentylcyclohexyl)-4-(4-(3-ethyl-3-butenyl)cyclohexyl)biphenyl
Compound No. 130
2'-Fluoro-4'-(4-propylcyclohexyl)-4-(4-(3-ethyl-3-butenyl)cyclohexyl)biphenyl
Compound No. 131
4'-(4-Propylcyclohexyl)-2-fluoro-4-(4-(3-ethyl-3-butenyl)cyclohexyl)biphenyl
Compound No. 132
4'-(2-(3',4'-Difluorobiphenylyl)ethyl)-4-(3-ethyl-3-butenyl)bicyclohexane
Compound No. 133
4'-(2-(3',4',5'-Trifluorobiphenylyl)ethyl)-4-(3-ethyl-3-butenyl)bicyclohexane S-I point 250° C. or above
Compound No. 134
4'-(4-(3',4',5'-Trifluorobiphenylyl)butyl)-4-(3-ethyl-3-butenyl)bicyclohexane
Compound No. 135
4'-(2-(3',4',5'-Trifluorobiphenylyl)ethenyl)-4-(3-ethyl-3-butenyl)bicyclohexane Example 4 (Application Example 1)

A liquid crystal composition $B_1$ comprising

24% of 4-(4-propylcyclohexyl)benzonitrile,

36% of 4-(4-pentylcyclohexyl)benzonitrile,

25% of 4-(4-heptylcyclohexyl)benzonitrile, and

15% of 4-(4-pentylphenyl)benzonitrile was prepared. This nematic liquid crystal had a clearing point of 72.4, a threshold voltage of 1.78 V in a cell thickness 9 μm, an anisotropy of dielectric constant of 11.0, an anisotropy of refractive index of 0.137, and a viscosity of 27.0 mPaS at 20. 85% of the liquid crystal composition was mixed with 15% of the compound of the present invention prepared in Example 1, 4'-propyl-4-(3-ethyl-3-butenyl)bicyclohexane (compound No. 4), to prepare a liquid crystal composition $A_1$. The liquid crystal composition $A_1$ had a clearing point of 66.7, a threshold voltage of 1.73 V in a cell thickness 8.7 μm, an anisotropy of dielectric constant of 9.3, an anisotropy of refractive index of 0.120, a viscosity of 22.9 mPaS at 20, and an elastic constant ratio K33/K11 of 2.34. This composition was allowed to stand in a freezer of −20 for 60 days. As a result, no crystal was precipitated. Further, the voltage retention of the composition $A_1$ was measured and found to be 99.2% at 100.

Example 5 (Application Example 2)

A liquid crystal composition $B_2$ comprising

30% of 4-(4-propylcyclohexyl)benzonitrile,

40% of 4-(4-pentylcyclohexyl)benzonitrile, and

30% of 4-(4-heptylcyclohexyl)benzonitrile was prepared. This nematic liquid crystal had a clearing point of 52.3, a threshold voltage of 1.60 V in a cell thickness 9 μm, an anisotropy of dielectric constant of 10.7, an anisotropy of refractive index of 0.119, and a viscosity of 21.7 mPaS at 20. 85% of the liquid crystal composition $B_2$ was mixed with 15% of the compound of the present invention prepared in Example 2, 4'-(4-(2-propyl-2-propenyl)cyclohexyl)-4-trifluoromethoxybiphenyl (compound No. 46), to prepare a liquid crystal composition $A_2$. The liquid crystal composition $A_2$ had a clearing point of 43.5, a threshold voltage of 1.33 V in a cell thickness 8.8 μm, an anisotropy of dielectric constant of 9.0, an anisotropy of refractive index of 0.018, and a viscosity of 25.6 mPaS at 20. This composition was allowed to stand in a freezer of −20 for 60 days. As a result, no crystal was precipitated. Further, the voltage retention of the composition $A_2$ was measured and found to be 99.8% at 100.

Example 6 (Application Example 3)

The following compound prepared according to a method described in M. Schadt et al., Mol. Cryst. Liq. Cryst., 122 (1985) and Japanese Patent Laid-Open No. 83136/1986:

$C_3H_7$—⟨cyclohexyl⟩—⟨cyclohexyl⟩—CH₂—CH=CH₂, the following compound prepared according to a method described in Japanese Patent Application No. 92740/1994:

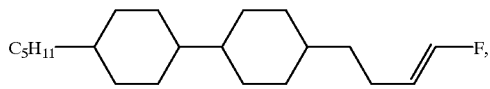

and the compound prepared in Example 1, compound No. 4, were each mixed in an amount of 15% with 85% of the liquid crystal composition $B_1$ to prepare liquid crystal compositions $A_3$, $A_4$, and $A_1$ (A1: prepared in Example 4). The elastic constant ratios (K33/K11) of the liquid crystal compositions $A_3$, $A_4$, and $A_1$ were 1.78, 1.90, and 2.34, respectively.

Example 7 (Application Example 4)

A liquid crystal composition was prepared according to the following formulation. The compounds used in the following exmaples were represented according to the notation given in Table 1.

TABLE 1

| Composition: | |
|---|---|
| 2Ve2-HH-3 | 11.0% |
| 1V2-BEB(F,F)-C | 5.0% |
| 3-HB-C | 25.0% |
| 1-BTB-3 | 5.0% |
| 2-BTB-1 | 5.0% |
| 3-HH-4 | 5.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

The above composition had the following property values. In this connection, $T_{NI}$ represents the nematic-isotropic liquid phase transition temperature, $\eta$ the viscosity, $\Delta n$ the anisotropy of refractive index, $\Delta\epsilon$ the anisotropy of dielectric constant, and $V_{th}$ the threshold voltage.

Property values:

$T_{NI} = 90.9$ (° C.)
$\eta = 15.4$ (mPa.s)
$\Delta n = 0.151$
$\Delta\epsilon = 6.8$
$V_{th} = 2.15$ (V)

Example 8 (Application Example 5)

| Composition: | |
|---|---|
| 2Ve2-HHB-C | 3.0% |
| V2-HB-C | 12.0% |
| 1V2-HB-C | 12.0% |
| 3-HB-C | 24.0% |
| 3-HB(F)-C | 5.0% |
| 2-BTB-1 | 2.0% |
| 3-HH-4 | 8.0% |
| 3-HH-VFF | 6.0% |
| 2-HHB-C | 3.0% |
| 3-HHB-C | 3.0% |
| 3-HB(F)TB-2 | 8.0% |
| 3-H2BTB-2 | 5.0% |
| 3-H2BTB-3 | 5.0% |
| 3-H2BTB-4 | 4.0% |

Property values:

$T_{NI} = 87.4$ (° C.)
$\eta = 17.6$ (mPa.s)
$\Delta n = 0.155$
$\Delta\epsilon = 8.8$
$V_{th} = 1.98$ (V)

Example 9 (Application Example 6)

| Composition: | |
|---|---|
| 3Ve1-HBB-OCF3 | 4.0% |
| 2O1-BEB(F)-C | 5.0% |
| 3O1-BEB(F)-C | 15.0% |
| 4O1-BEB(F)-C | 13.0% |
| 5O1-BEB(F)-C | 13.0% |
| 2-HHB(F)-C | 15.0% |
| 3-HHB(F)-C | 15.0% |
| 3-HB(F)TB-2 | 4.0% |
| 3-HB(F)TB-3 | 4.0% |
| 3-HB(F)TB-4 | 4.0% |
| 3-HHB-1 | 4.0% |
| 3-HHB-O1 | 4.0% |

Property values:

$T_{NI} = 86.2$ (° C.)
$\eta = 86.6$ (mPa.s)
$\Delta n = 0.146$
$\Delta\epsilon = 30.9$
$V_{th} = 0.86$ (V)

Example 10 (Application Example 7)

| Composition: | |
|---|---|
| 4Ve-HH-3 | 3.0% |
| 3Ve1-HH-3 | 3.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |

-continued

| Composition: | |
|---|---|
| 3-H2BTB-2 | 5.0% |
| 3-H2BTB-3 | 5.0% |
| 3-H2BTB-4 | 5.0% |

Property values:

$T_{NI} = 89.6$ (° C.)
$\eta = 32.0$ (mPa.s)
$\Delta n = 0.195$
$\Delta \epsilon = 6.5$
$V_{th} = 2.26$ (V)

Example 11 (Application Example 8)

| Composition: | |
|---|---|
| 3Ve1-HH-3 | 6.0% |
| 2Ve2-HHB-C | 4.0% |
| 3-DB-C | 10.0% |
| 4-DB-C | 10.0% |
| 2-BEB-C | 12.0% |
| 3-PyB(F)-F | 6.0% |
| 3-HEB-O4 | 8.0% |
| 4-HEB-O2 | 6.0% |
| 3-HEB-O2 | 5.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 6.0% |
| 3-HHEBB-C | 3.0% |
| 3-HBEBB-C | 3.0% |
| 5-HBEBB-C | 3.0% |

Property values:

$T_{NI} = 69.1$ (° C.)
$\eta = 39.1$ (mPa.s)
$\Delta n = 0.117$
$\Delta \epsilon = 10.5$
$V_{th} = 1.36$ (V)

Example 12 (Application Example 9)

| Composition: | |
|---|---|
| 2Ve2-HH-3 | 3.0% |
| 2Ve2-HH-5 | 3.0% |
| 3-HB-C | 18.0% |
| 5-HB-C | 3.0% |
| 1O1-HB-C | 10.0% |
| 3-HB(F)-C | 10.0% |
| 2-PyB-2 | 2.0% |
| 3-PyB-2 | 2.0% |
| 1O1-HH-3 | 3.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 8.0% |

-continued

| Composition: | |
|---|---|
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

Property values:

$T_{NI} = 79.9$ (° C.)
$\eta = 17.8$ (mPa.s)
$\Delta n = 0.139$
$\Delta \epsilon = 8.2$
$V_{th} = 1.74$ (V)

Example 13 (Application Example 10)

| Composition: | |
|---|---|
| 2Ve2-HH-5 | 5.0% |
| 2O1-BEB(F)-C | 5.0% |
| 3O1-BEB(F)-C | 12.0% |
| 5O1-BEB(F)-C | 4.0% |
| 1V2-BEB(F,F)-C | 10.0% |
| 3-HH-EMe | 5.0% |
| 3-HB-O2 | 18.0% |
| 3-HHEB-F | 3.0% |
| 5-HHEB-F | 3.0% |
| 3-HBEB-F | 4.0% |
| 2O1-HBEB(F)-C | 2.0% |
| 3-HB(F)EB(F)-C | 2.0% |
| 3-HBEB(F,F)-C | 2.0% |
| 3-HHB-F | 4.0% |
| 3-HHB-O1 | 4.0% |
| 3-HHB-3 | 13.0% |
| 3-HEBEB-F | 2.0% |
| 3-HEBEB-1 | 2.0% |

Property values:

$T_{NI} = 73.8$ (° C.)
$\eta = 34.5$ (mPa.s)
$\Delta n = 0.117$
$\Delta \epsilon = 23.6$
$V_{th} = 0.99$ (V)

Example 14 (Application Example 11)

| Composition: | |
|---|---|
| 2Ve2-HHB-OCF3 | 4.0% |
| 2O1-BEB(F)-C | 5.0% |
| 3O1-BEB(F)-C | 12.0% |
| 5O1-BEB(F)-C | 4.0% |
| 1V2-BEB(F,F)-C | 16.0% |
| 3-HB-O2 | 10.0% |
| 3-HH-4 | 3.0% |
| 3-HHB-F | 3.0% |
| 3-HHB-1 | 8.0% |
| 3-HHB-O1 | 4.0% |
| 3-HBEB-F | 4.0% |

-continued

| Composition: | |
|---|---|
| 3-HHEB-F | 3.0% |
| 5-HHEB-F | 7.0% |
| 3-H2BTB-2 | 4.0% |
| 3-H2BTB-3 | 4.0% |
| 3-H2BTB-4 | 4.0% |
| 3-HB(F)TB-2 | 5.0% |

Property values:

$T_{NI} = 86.9$ (° C.)
$\eta = 40.8$ (mPa.s)
$\Delta n = 0.145$
$\Delta \epsilon = 28.3$
$V_{th} = 1.00$ (V)

Example 15 (Application Example 12)

| Composition: | |
|---|---|
| 2Ve2-HH-3 | 5.0% |
| 2-BEB-C | 12.0% |
| 3-BEB-C | 4.0% |
| 4-BEB-C | 6.0% |
| 3-HB-C | 28.0% |
| 3-HEB-O4 | 7.0% |
| 4-HEB-O2 | 8.0% |
| 5-HEB-O1 | 8.0% |
| 3-HEB-O2 | 6.0% |
| 5-HEB-O2 | 5.0% |
| 3-HHB-1 | 7.0% |
| 3-HHB-O1 | 4.0% |

Property values:

$T_{NI} = 61.8$ (° C.)
$\eta = 24.6$ (mPa.s)
$\Delta n = 0.108$
$\Delta \epsilon = 9.9$
$V_{th} = 1.36$ (V)

Example 16 (Application Example 13)

| Composition: | |
|---|---|
| 2Ve2-HH-3 | 5.0% |
| 4Ve-HH-3 | 5.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |
| 3-HHB-3 | 13.0% |

Property values:

$T_{NI} = 64.6$ (° C.)
$\eta = 16.9$ (mPa.s)
$\Delta n = 0.149$
$\Delta \epsilon = 5.3$
$V_{th} = 1.97$ (V)

Example 17 (Application Example 14)

| Composition: | |
|---|---|
| 2Ve2-HBB(F)-F | 9.0% |
| 2-HHB(F)-F | 17.0% |
| 3-HHB(F)-F | 17.0% |
| 5-HHB(F)-F | 16.0% |
| 2-H2HB(F)-F | 10.0% |
| 3-H2HB(F)-F | 5.0% |
| 5-H2HB(F)-F | 10.0% |
| 2-HBB(F)-F | 4.0% |
| 3-HBB(F)-F | 4.0% |
| 5-HBB(F)-F | 8.0% |

Property values:

$T_{NI} = 97.8$ (° C.)
$\eta = 26.9$ (mPa.s)
$\Delta n = 0.097$
$\Delta \epsilon = 5.0$
$V_{th} = 2.22$ (V)

Example 18 (Application Example 15)

| Composition: | |
|---|---|
| 4Ve-HH-3 | 5.0% |
| 7-HB(F)-F | 5.0% |
| 5-H2B(F)-F | 5.0% |
| 3-HH-4 | 3.0% |
| 3-HB-O2 | 7.0% |
| 2-HHB(F)-F | 10.0% |
| 3-HHB(F)-F | 10.0% |
| 5-HHB(F)-F | 10.0% |
| 3-H2HB(F)-F | 5.0% |
| 2-HBB(F)-F | 3.0% |
| 3-HBB(F)-F | 3.0% |
| 5-HBB(F)-F | 6.0% |
| 2-H2BB(F)-F | 5.0% |
| 3-H2BB(F)-F | 6.0% |
| 3-HHB-1 | 8.0% |
| 3-HHB-O1 | 5.0% |
| 3-HHB-3 | 4.0% |

Property values:

$T_{NI} = 85.7$ (° C.)
$\eta = 18.4$ (mPa.s)
$\Delta n = 0.094$
$\Delta \epsilon = 3.1$
$V_{th} = 2.73$ (V)

Example 19 (Application Example 16)

| Composition: | |
|---|---|
| 2Ve2-HH-3 | 4.0% |
| 2Ve2-HBB(F)-F | 6.0% |
| 2Ve2-HBB(F,F)-F | 5.0% |
| 7-HB(F,F)-F | 3.0% |
| 3-HB-O2 | 3.0% |
| 2-HHB(F)-F | 10.0% |
| 3-HHB(F)-F | 10.0% |
| 5-HHB(F)-F | 10.0% |
| 2-HHB(F)-F | 7.0% |
| 3-HBB(F)-F | 7.0% |
| 5-HBB(F)-F | 14.0% |
| 2-HBB-F | 4.0% |
| 3-HBB-F | 4.0% |
| 5-HBB-F | 3.0% |
| 3-HBB(F,F)-F | 5.0% |
| 5-HBB(F,F)-F | 5.0% |

Property values:

$T_{NI} = 82.9$ (° C.)
$\eta = 27.1$ (mPa.s)
$\Delta n = 0.119$
$\Delta \epsilon = 5.4$
$V_{th} = 2.06$ (V)

Example 20 (Application Example 17)

| Composition: | | |
|---|---|---|
| | 2Ve2-HBB-(F,F)-F | 10.0% |
| | 7-HB(F,F)-F | 4.0% |
| | 3-H2HB(F,F)-F | 12.0% |
| | 4-H2HB(F,F)-F | 10.0% |
| | 5-H2HB(F,F)-F | 10.0% |
| | 3-HHB(F,F)-F | 10.0% |
| | 4-HHB(F,F)-F | 5.0% |
| | 3-HH2B(F,F)-F | 15.0% |
| | 5-HH2B(F,F)-F | 10.0% |
| | 3-HBB(F,F)-F | 6.0% |
| | 5-HBB(F,F)-F | 8.0% |

Property values:

$T_{NI} = 70.0$ (° C.)
$\eta = 29.6$ (mPa.s)
$\Delta n = 0.088$
$\Delta \epsilon = 8.7$
$V_{th} = 1.57$ (V)

Example 21 (Application Example 18)

| Composition: | | |
|---|---|---|
| | 3Ve1-HBB-OCF3 | 4.0% |
| | 2Ve2-HBB(F,F)-F | 4.0% |
| | 3-HB-CL | 10.0% |
| | 5-HB-CL | 4.0% |
| | 7-HB-CL | 4.0% |
| | 101-HH-5 | 5.0% |
| | 2-HBB-(F)-F | 8.0% |
| | 3-HBB(F)-F | 8.0% |
| | 5-HBB(F)-F | 14.0% |
| | 4-HHB-CL | 4.0% |

-continued

| | |
|---|---|
| 5-HHB-CL | 8.0% |
| 3-H2HB(F)-CL | 4.0% |
| 3-HBB(F,F)-F | 10.0% |
| 5-H2BB(F,F)-F | 5.0% |
| 3-HB(F)VB-2 | 4.0% |
| 3-HB(F)VB-3 | 4.0% |

Property values:

$T_{NI} = 83.1$ (° C.)
$\eta = 21.8$ (mPa.s)
$\Delta n = 0.129$
$\Delta \epsilon = 4.9$
$V_{th} = 2.32$ (V)

Example 22 (Application Example 19)

| Composition: | 2Ve2-HBB(F,F)-F | 10.0% |
|---|---|---|
| | 3-HHB(F,F)-F | 9.0% |
| | 3-H2HB(F,F)-F | 8.0% |
| | 4-H2HB(F,F)-F | 8.0% |
| | 5-H2HB(F,F)-F | 8.0% |
| | 3-HBB(F,F)-F | 21.0% |
| | 5-HBB(F,F)-F | 10.0% |
| | 3-H2BB(F,F)-F | 10.0% |
| | 5-HHBB(F,F)-F | 3.0% |
| | 3-HH2BB(F,F)-F | 3.0% |
| | 5-HHEBB-F | 2.0% |
| | 101-HBBH-4 | 4.0% |
| | 101-HBBH-5 | 4.0% |

Property values:

$T_{NI} = 94.0$ (° C.)
$\eta = 36.5$ (mPa.s)
$\Delta n = 0.119$
$\Delta \epsilon = 9.1$
$V_{th} = 1.75$ (V)

Example 23 (Application Example 20)

| Composition: | 2Ve2-HHB-OCF3 | 5.0% |
|---|---|---|
| | 2Ve2-HBB-OCF3 | 2.0% |
| | 2Ve2-HBB(F)-F | 8.0% |
| | 5-HB-F | 12.0% |
| | 6-HB-F | 9.0% |
| | 7-HB-F | 7.0% |
| | 2-HHB-OCF3 | 5.0% |
| | 3-HHB-OCF3 | 8.0% |
| | 4-HHB-OCF3 | 7.0% |
| | 5-HHB-OCF3 | 5.0% |
| | 3-HH2B-OCF3 | 4.0% |
| | 5-HH2B-OCF3 | 4.0% |
| | 3-HHB(F,F)-OCF3 | 5.0% |
| | 3-HBB(F)-F | 10.0% |
| | 3-HH2B(F)-F | 3.0% |
| | 3-HB(F)BH-3 | 3.0% |
| | 5-HBBH-3 | 3.0% |

Property values:

$T_{NI}$ = 78.1 (° C.)

$\eta$ = 17.2 (mPa.s)

$\Delta n$ = 0.097

$\Delta\epsilon$ = 4.4

$V_{th}$ = 2.43 (V)

Example 24 (Application Example 21)

| Composition: | | |
|---|---|---|
| | 2Ve2-HHB-OCF3 | 5.0% |
| | 5-H4HB(F,F)-F | 7.0% |
| | 5-H4HB-OCF3 | 10.0% |
| | 3-H4HB(F,F)-CF3 | 8.0% |
| | 5-H4HB(F,F)-CF3 | 10.0% |
| | 3-HB-CL | 6.0% |
| | 5-HB-CL | 4.0% |
| | 2-H2BB(F)-F | 5.0% |
| | 3-H2BB(F)-F | 10.0% |
| | 5-HVHB(F,F)-F | 5.0% |
| | 3-HHB-OCF3 | 5.0% |
| | 3-H2HB-OCF3 | 5.0% |
| | V-HHB(F)-F | 5.0% |
| | 3-HChB(F)-F | 5.0% |
| | 5-HHEB-OCF3 | 2.0% |
| | 3-HBEB(F,F)-F | 5.0% |
| | 5-HH-V2F | 3.0% |

Property values:

$T_{NI}$ = 69.2 (° C.)

$\eta$ = 26.2 (mPa.s)

$\Delta n$ = 0.091

$\Delta\epsilon$ = 8.3

$V_{th}$ = 1.74 (V)

Example 25 (Application Example 22)

| Composition: | | |
|---|---|---|
| | 2Ve2-HBB(F)-F | 6.0% |
| | 2Ve2-HBB(F,F)-F | 9.0% |
| | 2-HHB(F)-F | 2.0% |
| | 3-HHB(F)-F | 2.0% |
| | 5-HHB(F)-F | 2.0% |
| | 2-HBB(F)-F | 4.0% |
| | 3-HBB(F)-F | 4.0% |
| | 5-HBB(F)-F | 8.0% |
| | 2-H2BB(F)-F | 9.0% |
| | 3-H2BB(F)-F | 9.0% |
| | 3-HBB(F,F)-F | 25.0% |
| | 5-HBB(F,F)-F | 10.0% |
| | 101-HBBH-4 | 5.0% |
| | 101-HBBH-5 | 5.0% |

Property values:

$T_{NI}$ = 91.6 (° C.)

$\eta$ = 37.7 (mPa.s)

$\Delta n$ = 0.141

$\Delta\epsilon$ = 7.3

$V_{th}$ = 1.91 (V)

Industrial Applicability

As described above, the liquid crystalline compounds, of the present invention, represented by the formula (1) have the following properties.

1) Very large elastic constant ratio K33/K11
2) Very high chemical stability
3) Compatibility with other liquid crystalline compound particularly at a low temperature
4) High positive anisotropy of dielectric constant
5) Very high specific resistance (high voltage retention) and good UV stability The liquid crystalline compounds of the present invention, represented by the formula (1), having the above excellent properties can be used to prepare liquid crystalline compositions, having excellent properties, which are suitable for applications in electro-optical display materials (liquid crystal display devices) used in watches and clocks, electronic calculators, various types of measuring equipment, panels for automobiles, word processors, electronic message pads, printers, computers, televisions, etc.

TABLE 1

| Symbolizing Metod of compounds R$-(A_1)-Z_1- \ldots Z_n-(A_n)-$X | |
|---|---|
| 1) Left Terminal R— | Symbol |
| $C_nH_{2n+1}$— | n— |
| $C_nH_{2n+1}O$— | nO— |
| $C_nH_{2n+1}OC_mH_{2m}$— | nOm— |
| $CH_2$=CH— | V— |
| $CH_2$=CHC$_n$H$_{2n}$— | Vn— |
| $C_nH_{2n+1}$CH=CHC$_m$H$_{2m}$— | nVm— |
| $C_nH_{2n+1}$CH=CHC$_m$H$_{2m}$CH=CHC$_k$H$_{2k}$— | nVmVk— |
| $C_nH_{2n+1}CC_mH_{2m}$— <br> ‖ <br> $CH_2$ | nVem— |
| 2) Ring Structure $-(A_1)-$, $-(A_n)-$ | Symbol |

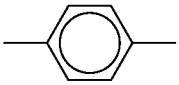

B

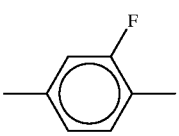

B(F)

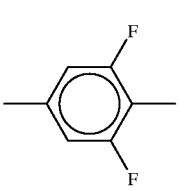

B(F,F)

H

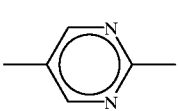

Py

TABLE 1-continued

Symbolizing Metod of compounds
R—(A₁)—Z₁— . . . Zₙ—(Aₙ)—X

| | |
|---|---|
| 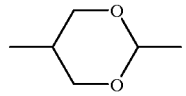 | D |
| 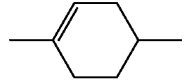 | Ch |

| 3) Linkage —$Z_1$—, —$Z_2$— | Symbol |
|---|---|
| —$C_2H_4$— | 2 |
| —$C_4H_8$— | 4 |
| —COO— | E |
| —C≡C— | T |
| —CH=CH— | V |
| —$CF_2O$— | CF2O |
| —$OCF_2$— | OCF2 |

| 4) Right Terminal —X | Symbol |
|---|---|
| —F | —F |
| —Cl | —CL |
| —CN | —C |
| —CF3 | —CF3 |
| —OCF3 | —OCF3 |
| —$OCF_2H$ | —OCF2H |
| —$C_nH_{2n+1}$ | —n |
| —$OC_nH_{2n+1}$ | —On |
| —$COOCH_3$ | —EMe |
| —$C_nH_{2n}CH=CH_2$ | —nV |
| —$C_mH_{2m}CH=CHC_nH_{2n+1}$ | —mVn |
| —$C_mH_{2m}CH=CHC_nH_{2n}F$ | —mVnF |
| —CH=$CF_2$ | —VFF |

5) Symbolizing Examples ex. 1   3-H2B(F,F)B(F)—F

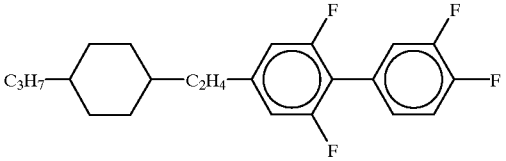

ex. 2   3-HB(F)TB-2

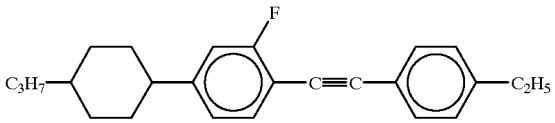

ex. 3   IV2-BEB(F,F)—C

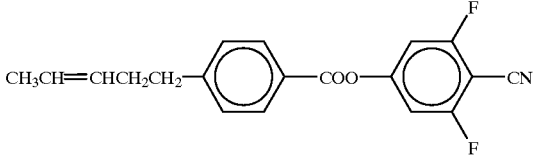

What is claimed is:

1. A liquid crystalline compound represented by the general formula (1):

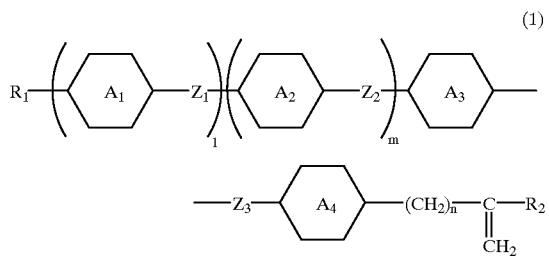

(1)

wherein $R_1$ represents an alkyl or alkoxy group having 1 to 10 carbon atoms, a cyano group, a halogen atom, or an alkyl or alkoxy halide group having 1 to 4 carbon atoms;

$R_2$ represents an alkyl group having 2 to 10 carbon atoms;

rings $A_1$, $A_2$, $A_3$, and $A_4$ each independently represent a 1,4-phenylene, 1,4-cyclohexylene, 1,4-cyclohexenylene, 1,3-dioxane-2,5-diyl, Dyrimidine-2,5-diyl, pyridine-2,5-diyl, or bicyclo[1,1,1]pentanediyl group, provided that the rings may be substituted with one or more halogen atoms;

$Z_1$, $Z_2$, and $Z_3$ each independently represent a covalent bond, —$CH_2CH_2$—, —CH=CH—, —C≡C—, —COO—, —OCO—, —$CH_2O$—, —$OCH_2$— or —$(CH_2)_4$—;

l and m are 0 or 1; and n is 0 to 10;

provided that $R_2$ is an alkyl group having 2 to 10 carbon atoms when $R_1$ is a halogen atom, a halogenated alkyl group or a halogenated alkoxy group, the ring to which $R_1$ is directly connected is a 1,4-phenylene group which may be substituted by a halogen atom, and ring $A_4$ is a 1,4-cyclohexylene group.

2. A liquid crystal display device comprising a liquid crystal composition, the liquid crystal composition comprising at least one liquid crystalline compound according to claim 1.

3. A liquid crystal composition comprising more than one compound, at least one of which is a liquid crystalline compound according to claim 1.

4. A liquid crystal display device comprising a liquid crystal composition according to claim 3.

5. A liquid crystalline compound represented by the general formula (1-1):

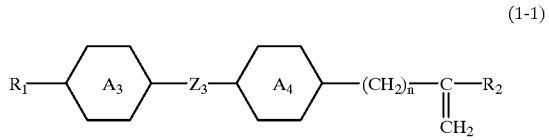

(1-1)

wherein $R_1$ represents an alkyl or alkoxy group having 1 to 10 carbon atoms, a cyano group, a halogen atom, or an alkyl or alkoxy halide group having 1 to 4 carbon atoms;

$R_2$ represents an alkyl group having 2 to 10 carbon atoms;

rings $A_3$ and $A_4$ each independently represent a 1,4-phenylene or 1,4-cyclohexylene, provided that the rings may be substituted with one or more halogen atoms;

$Z_3$ represents a covalent bond, —$CH_2CH_2$—, —CH=CH—, —C≡C—, —COO—, —OCO—, —$CH_2O$—, —$OCH_2$— or —$(CH_2)_4$—; and n is 0 to 10;

provided that $R_2$ is an alkyl group having 2 to 10 carbon atoms when $R_1$ is a halogen atom, a halogenated alkyl group or a halogenated alkoxy group, ring $A_3$ is a 1,4-phenylene group which may be substituted by a halogen atom, and ring $A_4$ is a 1,4-cyclohexylene group.

6. The liquid crystalline compound according to claim 5, wherein $Z_3$ represents a covalent bond, —$CH_2CH_2$—, —CH=CH— or —C≡C—.

7. The liquid crystalline compound according to claim 5, wherein $R_1$ represents an alkyl group having 1 to 10 carbon atoms, rings $A_3$ and $A_4$ represent a 1,4-cyclohexylene group, $Z_3$ represents a covalent bond, —$CH_2CH_2$— or —CH=CH— and n is 0 to 10.

8. A liquid crystalline compound represented by the general formula (1-2):

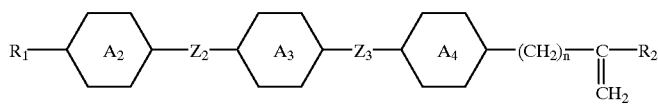

(1-2)

wherein $R_1$ represents an alkyl or alkoxy group having 1 to 10 carbon atoms, a cyano group, a halogen atom, or an alkyl or alkoxy halide group having 1 to 4 carbon atoms;

$R_2$ represents an alkyl group having 1 to 10 carbon atoms;

rings $A_2$, $A_3$ and $A_4$ each independently represent a 1,4-phenylene or 1,4-cyclohexylene, provided that the rings may be substituted with one or more halogen atoms;

$Z_2$ and $Z_3$ each independently represent a covalent bond, —$CH_2CH$—, —CH=CH—, —C≡C—, —COO—, —OCO—, —$CH_2O$—, —$OCH_2$— or —$(CH_2)_4$—; and n is 0 to 10;

provided that $R_2$ is an alkyl group having 2 to 10 carbon atoms when $R_1$ is a halogen atom, a halogenated alkyl group or a halogenated alkoxy group, ring $A_2$ is a 1,4-phenylene group which may be substituted by a halogen atom, and ring $A_4$ is a 1,4-cyclohexylene group.

9. The liquid crystalline compound according to claim 8, wherein $Z_2$ and $Z_3$ each independently represent a covalent bond, —$CH_2CH_2$—, —CH=CH—, —C≡C— or —$(CH_2)_4$—.

10. The liquid crystalline compound according to claim 9, wherein $R_1$ represents a cyano group, a halogen atom, or an alkyl halide or alkoxy halide group having 1 to 4 carbon atoms and ring $A_2$ represents a 1,4-phenylene group, provided that the ring may be substituted with one or more halogen atoms.

11. The liquid crystalline compound according to claim 9, wherein $R_1$ represents an alkyl group having 1 to 10 carbon atoms, and ring $A_2$ represents a 1,4-cyclohexylene group, provided that the ring may be substituted with one or more halogen atoms.

12. The liquid crystalline compound according to claim 8, which is represented by the general formula (1-3):

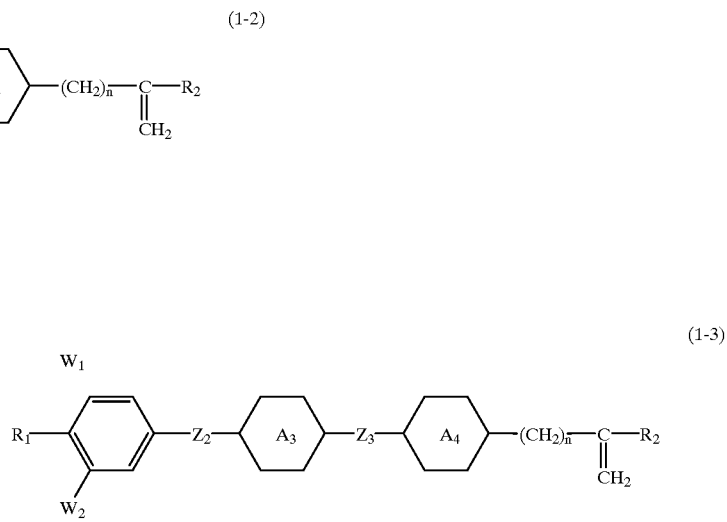

(1-3)

wherein $R_1$ represents a cyano group, a halogen atom, or an alkyl or alkoxy group having 1 to 4 carbon atoms;

$W_1$ and $W_2$ represent a fluorine or chlorine atom;

$Z_2$ and $Z_3$ each independently represent —$CH_2CH_2$— or —$(CH_2)_4$—; and n is 0 to 10;

provided that $R_2$ is an alkyl group having 2 to 10 carbon atoms when $R_1$ is a halogen atom, a halogenated alkyl group or a halogenated alkoxy group, and ring $A_4$ is a 1,4-cyclohexylene group.

13. The liquid crystalline compound according to claim 12, wherein $R_1$ represents a cyano group, a fluorine or chlorine atom, a trifluoromethyl, trifluoromethoxy, difluoromethoxy, 1,1,2,2-tetrafluoroethoxy, 1,1,2,3,3,3-hexafluoropropoxy, 2,2-difluoroethoxy, or 2,2,2-trifluoroethoxy group and $Z_2$ and $Z_3$ each independently represent a covalent bond, —$CH_2CH_2$— or —$(CH_2)_4$—.

14. A liquid crystal composition comprising: a first component of at least one compound according to any one of claims 1, 5–12 and 13; and a second component of at least one member selected from the group consisting of compounds represented by the general formulae (2), (3), and (4):

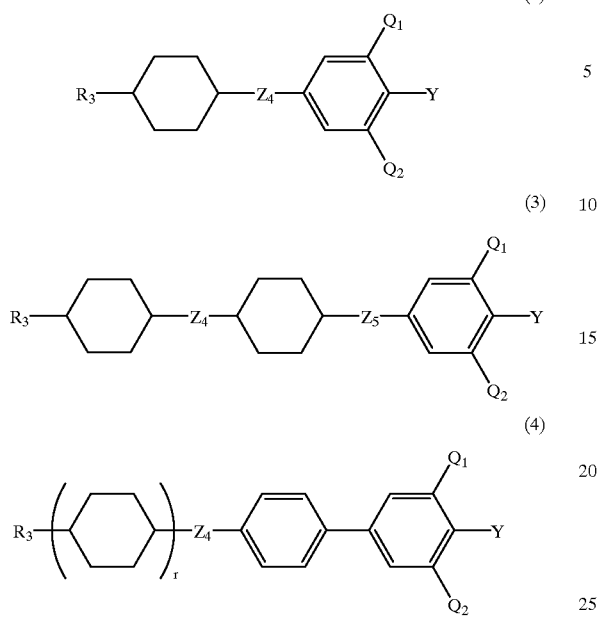

(2)

(3)

(4)

wherein $R_3$ represents an alkyl group having 1 to 10 carbon atoms, Y represents a fluorine or chlorine atom, $Q_1$ and $Q_2$ each independently represent a hydrogen or fluorine atom, r is 1 or 2, and $Z_4$ and $Z_5$ each independently represent —$CH_2CH_2$— or a covalent bond.

15. A liquid crystal composition comprising: a first component of at least one compound according to any one of claims 1, 5–12 and 13; and a second component of at least one member selected from the group consisting of compounds represented by the general formulae (5), (6), (7), (8), and (9):

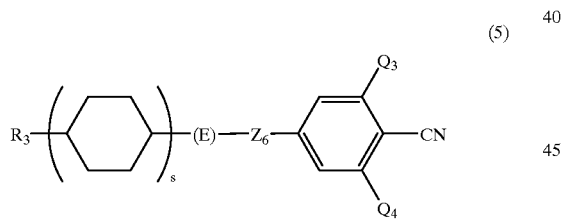

(5)

wherein $R_4$ represents an alkyl group having 1 to 10 carbon atoms or an alkenyl group having 2 to 10 carbon atoms, provided that although any methylene group (—$CH_2$—) may be replaced by an oxygen atom (—O—), two or more consecutive methylene groups are not simultaneously replaced by an oxygen atom, $Z_6$ represents —$CH_2CH_2$—, —COO— or a covalent bond, $Q_3$ and $Q_4$ represent a hydrogen or fluorine atom, E represents a cyclohexane, benzene, or 1,3-dioxane ring, and s is 0 or 1;

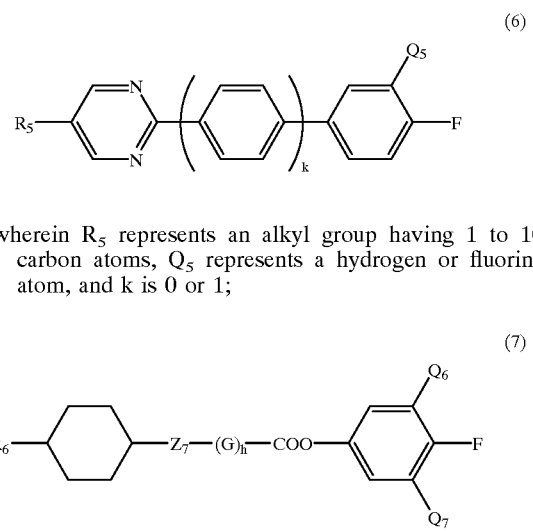

(6)

wherein $R_5$ represents an alkyl group having 1 to 10 carbon atoms, $Q_5$ represents a hydrogen or fluorine atom, and k is 0 or 1;

(7)

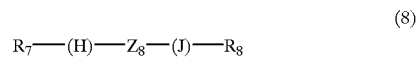

wherein $R_6$ represents an alkyl group having 1 to 10 carbon atoms, G represents a cyclohexane or benzene ring, $Q_6$ and $Q_7$ each independently represent a hydrogen or fluorine atom, $Z_7$ represents —COO— or a covalent bond, and h is 0 or 1;

(8)

$$R_7\text{---(H)---}Z_8\text{---(J)---}R_8$$

wherein $R_7$ and $R_8$ each independently represent an alkyl, alkyloxy or alkyloxymethyl group having 1 to 10 carbon atoms, H represents a cyclohexane, pyrimidine or benzene ring, J represents a cyclohexane or benzene ring, and $Z_8$ represents —C≡C—, —COO—, —$CH_2CH_2$— or a covalent bond; and (9)

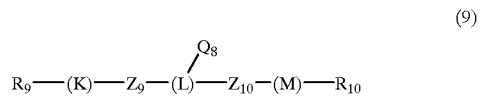

wherein $R_9$ represents an alkyl or alkoxyl group having 1 to 10 carbon atoms, $R_{10}$ represents an alkyl, alkyloxy or alkoxymethyl group having 1 to 10 carbon atoms, K represents a cyclohexane or pyrimidine ring, L and M each independently represent a cyclohexane or benzene ring, $Z_9$ represents —COO—, —$CH_2CH_2$— or a covalent bond, $Z_{10}$ represents —C≡C—, —COO—, or a covalent bond, and $Q_8$ represents hydrogen or florine atom.

16. A liquid crystal display device comprising a liquid crystal composition according to claim 14.

17. A liquid crystal display device comprising a liquid crystal composition according to claim 15.

* * * * *